(12) United States Patent
Kaji et al.

(10) Patent No.: US 9,818,955 B2
(45) Date of Patent: Nov. 14, 2017

(54) COMPOUND, LIGHT EMITTING MATERIAL, AND ORGANIC LIGHT EMITTING DEVICE

(71) Applicant: KYUSHU UNIVERSITY NATIONAL UNIVERSITY CORPORATION, Fukuoka-shi, Fukuoka (JP)

(72) Inventors: Hironori Kaji, Kyoto (JP); Hajime Suzuki, Kyoto (JP); Katsuaki Suzuki, Kyoto (JP); Hajime Oiwa, Kyoto (JP); Atsushi Wakamiya, Kyoto (JP); Tatsuya Fukushima, Kyoto (JP); Furitsu Suzuki, Kyoto (JP); Yasujiro Murata, Kyoto (JP); Katsuyuki Shizu, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 79 days.

(21) Appl. No.: 14/771,520

(22) PCT Filed: Feb. 28, 2014

(86) PCT No.: PCT/JP2014/055005
§ 371 (c)(1),
(2) Date: Aug. 31, 2015

(87) PCT Pub. No.: WO2014/133121
PCT Pub. Date: Sep. 4, 2014

(65) Prior Publication Data
US 2016/0020402 A1    Jan. 21, 2016

(30) Foreign Application Priority Data
Mar. 1, 2013    (JP) .................................. 2013-041106

(51) Int. Cl.
*H01L 51/00* (2006.01)
*C09K 11/06* (2006.01)
(Continued)

(52) U.S. Cl.
CPC ........ *H01L 51/0061* (2013.01); *C07D 209/86* (2013.01); *C07D 223/22* (2013.01);
(Continued)

(58) Field of Classification Search
None
See application file for complete search history.

(56) References Cited

U.S. PATENT DOCUMENTS

2007/0257600 A1    11/2007    Matsuura et al.
2011/0210318 A1    9/2011    Bae et al.
(Continued)

FOREIGN PATENT DOCUMENTS

CN    102197027 A    9/2011
JP    2002193952 A    7/2002
(Continued)

OTHER PUBLICATIONS

Kundu P et al, "Advanced Functional Materials" Advanced Functional Materials 13(6) 445-452 (2003).
(Continued)

*Primary Examiner* — J. L. Yang
(74) *Attorney, Agent, or Firm* — Browdy and Neimark, PLLC

(57) ABSTRACT

The compound represented by the following general formula is useful as a light emitting material. $Ar^1$ represents an arylene group, $Ar^2$ and $Ar^3$ represent an aryl group, and $R^1$ to $R^8$ represent a hydrogen atom or a substituent, provided that at least one of $R^1$ to $R^8$ represents a diarylamino group.
(Continued)

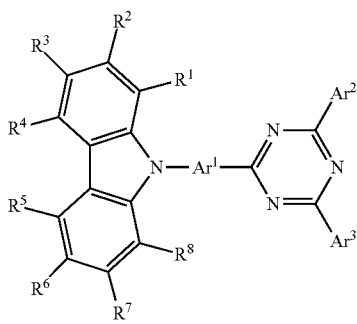

General Formula (1)

8 Claims, 9 Drawing Sheets

(51) Int. Cl.
C07D 403/10 (2006.01)
C07D 401/14 (2006.01)
C07D 223/22 (2006.01)
C07D 235/06 (2006.01)
C07D 239/26 (2006.01)
C07D 251/24 (2006.01)
C07D 471/04 (2006.01)
C07D 487/04 (2006.01)
C07D 271/107 (2006.01)
C07D 209/86 (2006.01)
C07F 9/50 (2006.01)
C07F 9/53 (2006.01)
C07F 9/6553 (2006.01)
C07F 1/00 (2006.01)
C07F 3/00 (2006.01)
C07F 5/02 (2006.01)
C07F 5/06 (2006.01)
C07F 7/08 (2006.01)
C07F 7/12 (2006.01)
C07F 7/18 (2006.01)
C07F 7/22 (2006.01)
H01L 51/50 (2006.01)

(52) U.S. Cl.
CPC ......... C07D 235/06 (2013.01); C07D 239/26 (2013.01); C07D 251/24 (2013.01); C07D 271/107 (2013.01); C07D 401/14 (2013.01); C07D 403/10 (2013.01); C07D 471/04 (2013.01); C07D 487/04 (2013.01); C07F 1/005 (2013.01); C07F 3/003 (2013.01); C07F 5/022 (2013.01); C07F 5/069 (2013.01); C07F 7/0807 (2013.01); C07F 7/0809 (2013.01); C07F 7/0818 (2013.01); C07F 7/12 (2013.01); C07F 7/1836 (2013.01); C07F 7/2212 (2013.01); C07F 9/5022 (2013.01); C07F 9/5325 (2013.01); C07F 9/655354 (2013.01); C09K 11/06 (2013.01); H01L 51/0067 (2013.01); H01L 51/0072 (2013.01); C09K 2211/1007 (2013.01); C09K 2211/1029 (2013.01); C09K 2211/1059 (2013.01); H01L 51/5012 (2013.01)

(56) References Cited

U.S. PATENT DOCUMENTS

2014/0054564 A1 2/2014 Kim et al.
2014/0158992 A1* 6/2014 Xia ............... H01L 51/0072
257/40

FOREIGN PATENT DOCUMENTS

JP 200921336 A 1/2009
KR 20100131939 A 12/2010
KR 10-2012-0013173 A 2/2012
KR 20120072787 A 7/2012
TW 201132627 A1 10/2011
WO 2005076669 A1 8/2005
WO 2010021524 A2 2/2010
WO 2011049325 A2 4/2011
WO 2012015274 A2 2/2012
WO 2012077902 A2 6/2012
WO 2015125986 A1 8/2015

OTHER PUBLICATIONS

International Search Report, dated Mar. 18, 2014, in corresponding application No. JP2014055005.
International Preliminary report, dated Feb. 28, 2014, in corresponding application No. JP2014055005.
Chen et al "Conjugated polymers containing trifluoren-2-ylamine, trifluoren-2-ylbenzene and trifluroren-2-ylrriazine for electroluminescence" Polymer 54 : 162-173 (2013).
Chinese Office Action dated Jun. 27, 2016, in corresponding application No. 201480010316.
Extended European Search Report, dated Aug. 31, 2016. In corresponding application No. 14757587.2.
Office Action for corresponding Taiwanese Patent Application No. 103106934, dated May 4, 2017, with English translation.
Office Action for corresponding Chinese Patent Application No. 201480010316.7, dated May 24, 2017, with partial (excerpt) English translation.
Office Action in corresponding Japanese Patent Application No. 22015-503044, dated Sep. 20, 2017, with English translation.

* cited by examiner

COMPOUND, LIGHT EMITTING MATERIAL, AND ORGANIC LIGHT EMITTING DEVICE

TECHNICAL FIELD

The present invention relates to a compound that is useful as a light emitting material, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitting material and the like constituting an organic electroluminescent device. There are studies relating to an organic electroluminescent device utilizing a compound containing a triazine ring and a carbazole ring, which are found among them, and some proposals have been made hitherto.

For example, Patent Document 1 describes the compound represented by the following general formula as a compound emitting blue fluorescent light, and describes that the compound is capable of being used in a light emitting device having a light emitting layer and the like between a pair of electrodes. In the following general formula, $R^{11}$ and $R^{12}$ each represent a hydrogen atom, an aliphatic hydrocarbon group, an aryl group or a heterocyclic group, $R^1$ and $R^2$ each represent a hydrogen atom or a substituent that does not contain an amino group, and L represent a linking group. PLT 1 describes that $R^{11}$ and $R^{12}$ may be bonded to each other to forma carbazole ring, and a light emitting device using the following compound A emits blue light. However, there is no description or suggestion of a compound that has a carbazole ring having a diarylamino group substituted thereon.

[chem 1]

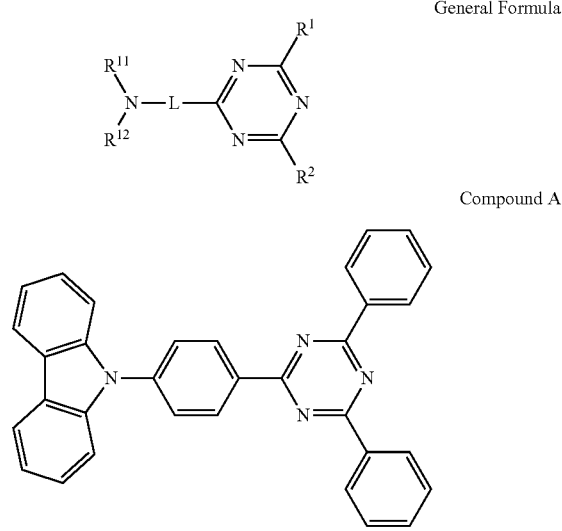

General Formula

Compound A

Patent Document 2 describes the usefulness of the compound A and the analogous compounds thereof, as an electron transporting material. Patent Document 3 describes the usefulness of the compound containing a triazine ring and a carbazole ring that are bonded to each other through an arylene group, as an electron transporting material. Patent Document 4 describes the usefulness of the compound A and the analogous compounds thereof, as a host material of a light emitting layer. In Patent Documents 2 to 4, however, there is no description or suggestion of a compound that has a carbazole ring having a diarylamino group substituted thereon.

CITATION LIST

Patent Literatures

Patent Document 1: JP-A-2002-193952
Patent Document 2: WO 2005/076669
Patent Document 3: JP-A-2009-21336
Patent Document 4: WO 2012/015274

SUMMARY OF INVENTION

Technical Problem

As described above, there have been proposal of the use of a compound having a triazine ring and a carbazole ring in a light emitting device. However, the general formulae described in Patent Documents 1 to 4 encompass an extremely wide range of compounds, and the example compounds shown therein have a wide variety of structures. Meanwhile, only Patent Document 1 describes the usefulness as a light emitting material, and in the examples therein, only several compounds are specifically confirmed for the usefulness as a light emitting material. Furthermore, as a result of studies by the present inventors, the compound A, which has been specifically confirmed in Patent Document for the effect as a light emitting material, still has room for improvement in light emission efficiency.

Patent Documents 1 to 4 do not specifically describe about a measure for further improving the light emission efficiency. Accordingly, it may not be said that the relationship between the light emission efficiency as a light emitting material and the structure of the analogous compounds is clarified. Therefore, it is difficult to estimate accurately the light emission characteristics of the analogous compounds of the compounds described in Patent Documents 1 to 4.

The present inventors have considered the problems of the related art and have made investigations for providing a compound having high light emission efficiency. The inventors also have made investigations for providing a general formula of compounds that are useful as a light emitting material and generalizing the structure of an organic light emitting device having a high light emission efficiency.

Solution to Problem

As a result of earnest investigations for achieving the objects, the inventors have succeeded in the synthesis of a group of compounds having a particular structure, and have found excellent properties of the group of compounds as a light emitting material. The inventors have also found compounds that are useful as a delayed fluorescent emitter in the group of compounds, and have clarified that an organic light emitting device having a high light emission efficiency may be provided inexpensively. Based on the knowledge, the inventors have provided the following inventions as measures for solving the problems.

(1) A compound represented by the following general formula (1):

[chem 2]

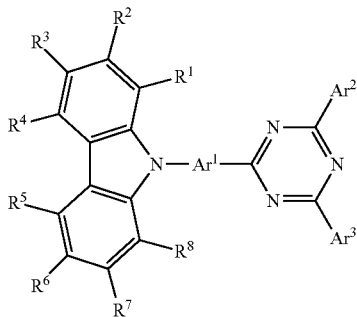

General Formula (1)

wherein in the general formula (1), $Ar^1$ represents a substituted or unsubstituted arylene group; $Ar^2$ and $Ar^3$ each independently represent a substituted or unsubstituted aryl group; and $R^1$ to $R^8$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form acyclic structure.

(2) The compound according to the item (1), wherein in the general formula (1), at least one of $R^1$ to $R^4$ represents a substituted or unsubstituted diarylamino group, and at least one of $R^5$ to $R^8$ represents a substituted or unsubstituted diarylamino group.

(3) The compound according to the item (2), wherein $R^3$ and $R^6$ in the general formula (1) each represent a substituted or unsubstituted diarylamino group.

(4) The compound according to any one of the items (1) to (3), wherein at least one of $R^1$ to $R^8$ in the general formula (1) represents a substituted or unsubstituted diphenylamino group.

(5) The compound according to any one of the items (1) to (4), wherein $Ar^2$ and $Ar^3$ in the general formula (1) each independently represent a substituted or unsubstituted phenyl group.

(6) The compound according to any one of the items (1) to (5), wherein $Ar^1$ in the general formula (1) represents a substituted or unsubstituted phenylene group, a substituted or unsubstituted naphthylene group or a substituted or unsubstituted anthracenyl group.

(7) The compound according to the item (1), wherein the compound is represented by the following general formula (2):

[chem 3]

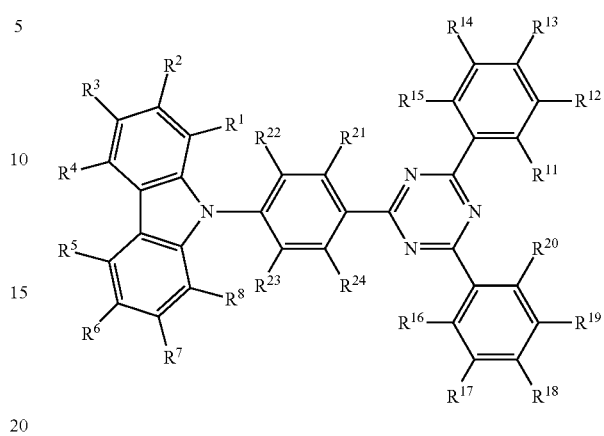

General Formula (2)

wherein in the general formula (2), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$, and $R^{19}$, $R^{19}$ and $R^{20}$, $R^{21}$ and $R^{22}$, and $R^{23}$ and $R^{24}$ each may be bonded to each other to form a cyclic structure.

(8) The compound according to the item (7), wherein in the general formula (2), at least one of $R^1$ to $R^4$ represents a substituted or unsubstituted diarylamino group, and at least one of $R^5$ to $R^8$ represents a substituted or unsubstituted diarylamino group.

(9) The compound according to the item (8), wherein $R^3$ and $R^6$ in the general formula (2) each represent a substituted or unsubstituted diarylamino group.

(10) Alight emitting material containing the compound according to any one of the items (1) to (9).

(11) A delayed fluorescent emitter having a structure represented by the general formula (1).

(12) An organic light emitting device containing a substrate having thereon alight emitting layer containing the light emitting material according to the item (10).

(13) The organic light emitting device according to the item (12), wherein the organic light emitting device emits delayed fluorescent light.

(14) The organic light emitting device according to the item (12) or (13), wherein the organic light emitting device is an organic electroluminescent device.

Advantageous Effects of Invention

The compound of the invention is useful as a light emitting material. The compound of the invention includes a compound that emits delayed fluorescent light. An organic light emitting device using the compound of the invention as a light emitting material is capable of achieving a high light emission efficiency.

DESCRIPTION OF EMBODIMENTS

Figure 1:
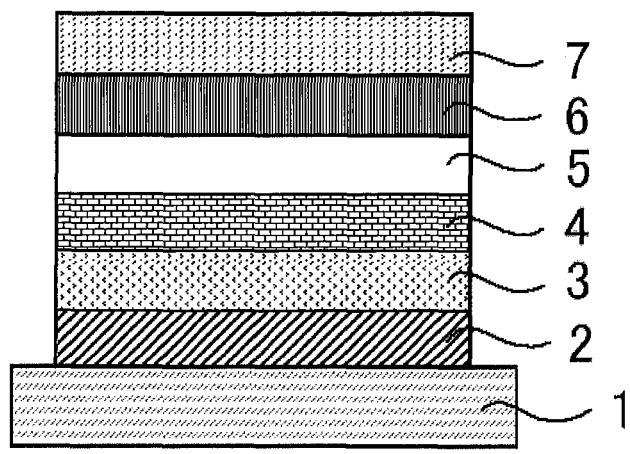
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D)).

Compound Represented by General Formula (1)

The compound of the invention has a structure represented by the following general formula (1).

[chem 4]

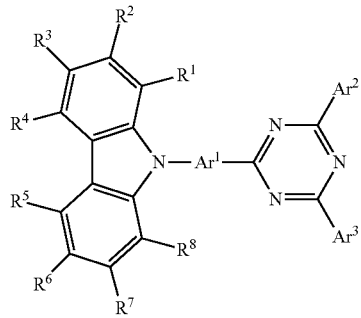

General Formula (1)

In the general formula (1), $Ar^1$ represents a substituted or unsubstituted arylene group. The aromatic ring constituting the arylene group may be a monocyclic ring or a fused ring, and specific examples thereof include a benzene ring, a naphthalene ring, an anthracene ring and a phenanthrene ring. The arylene group preferably has from 6 to 40 carbon atoms, more preferably from 6 to 20 carbon atoms, and further preferably from 6 to 14 carbon atoms. Specific examples of the arylene group include a 1,4-phenylene group, a 1,3-phenylene group, a 1,2-phenylene group, a 1,8-naphthylene group, a 2,7-naphthylene group, a 2,6-naphthylene group, a 1,4-naphthylene group, a 1,3-naphthylene group, a 9,10-anthracenylene group, a 1,8-anthracenylene group, a 2,7-anthracenylene group, a 2,6-anthracenylene group, a 1,4-anthracenylene group and a 1,3-anthracenylene group, and a 1,4-phenylene group, a 1,3-phenylene group, a 1,8-naphthylene group, a 2,7-naphthylene group, a 1,4-naphthylene group, a 1,3-naphthylene group and a 9,10-anthracenylene group are preferred. The hydrogen atoms present in the structures of the specific examples may be substituted.

In the general formula (1), $Ar^2$ and $Ar^3$ each independently represent a substituted or unsubstituted aryl group. The aromatic ring constituting the aryl group may be a monocyclic ring or a fused ring, and specific examples thereof include a benzene ring, a naphthalene ring, an anthracene ring and a phenanthrene ring. The aryl group preferably has from 6 to 40 carbon atoms, more preferably from 6 to 20 carbon atoms, and further preferably from 6 to 14 carbon atoms. Specific examples of the aryl group include a phenyl group, a 1-naphthyl group, a 2-naphthyl group, a 1-anthracenyl group, a 2-anthracenyl group and a 9-anthracenyl group, and a phenyl group, a 1-naphthyl group and a 2-naphthyl group are preferred. The hydrogen atoms present in the structures of the specific examples may be substituted. In the general formula (1), $Ar^2$ and $Ar^3$ may be the same as or different from each other, and the compound having $Ar^2$ and $Ar^3$ that are the same as each other may be advantageously synthesized relatively easily.

The arylene group represented by $Ar^1$ and the aryl groups represented by $Ar^2$ and $Ar^3$ each may have a substituent or may be unsubstituted. In the case where the group has two or more substituents, the plural substituents may be the same as or different from each other. Examples of the substituent include a hydroxyl group, a halogen atom, an alkyl group having from 1 to 20 carbon atoms, an alkoxy group having from 1 to 20 carbon atoms, an alkylthio group having from 1 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, a haloalkyl group having from 1 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms and a trialkylsilylalkynyl group having from 5 to 20 carbon atoms. In these specific examples, the substituent that is capable of being further substituted with a substituent may be substituted. More preferred examples of the substituent include a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms and a substituted or unsubstituted heteroaryl group having from 3 to 40 carbon atoms. Further preferred examples of the substituent include a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms and a substituted or unsubstituted heteroaryl group having from 3 to 12 carbon atoms.

The alkyl group may be linear, branched or cyclic, and more preferably has from 1 to 6 carbon atoms, and specific examples thereof include a methyl group, an ethyl group, a propyl group, a butyl group, a tert-butyl group, a pentyl group, a hexyl group and an isopropyl group. The alkoxy group may be linear, branched or cyclic, and more preferably has from 1 to 6 carbon atoms, and specific examples thereof include a methoxy group, an ethoxy group, a propoxy group, a butoxy group, a tert-butoxy group, a pentyloxy group, a hexyloxy group and an isopropoxy group. Examples of the aryl group that is capable of being used as the substituent may be a monocyclic ring or a condensed ring, and specific examples thereof include a phenyl group and a naphthyl group. The heteroaryl group may be a monocyclic ring or a condensed ring, and specific examples thereof include a pyridyl group, a pyridazyl group, a pyrimidyl group, a triazyl group, a triazolyl group and a benzotriazolyl group. The heteroaryl group may be a group that is bonded through the hetero atom or a group that is bonded through the carbon atom constituting the heteroaryl ring.

In the general formula (1), $R^1$ to $R^8$ each independently represent a hydrogen atom or a substituent, provided that at least one of $R^1$ to $R^8$ represents a substituted or unsubstituted diarylamino group. The two aryl groups of the diarylamino group herein may be the same as or different from each other, and are preferably the same as each other. For the definition and the preferred ranges of the aryl groups, reference may be made to the description for the aryl groups represented by $Ar^2$ and $Ar^3$. The two aryl groups of the diarylamino group may be bonded to each other to form, for example, a carbazole ring. Specific examples of the diarylamino group include a diphenylamino group, a di(1-naphthyl)amino group, a di(2-naphthyl)amino group, a di(4-methylphenyl)amino group, a di(3-methylphenyl)amino group, a di(3,5-dimethylphenyl)amino group, a di(4-biphenyl)amino group and a 9-carbazolyl group.

In the general formula (1), at least one of $R^1$ to $R^8$ necessarily represents a substituted or unsubstituted diarylamino group. The case where from 1 to 4 of $R^1$ to $R^8$ each represent a substituted or unsubstituted diarylamino group is preferred, and the case where from 2 to 4 of $R^1$ to $R^8$ each represent a substituted or unsubstituted diarylamino group is more preferred. In the case where 2 or more of them each represent a substituted or unsubstituted diarylamino group, the plural substituted or unsubstituted diarylamino groups may be the same as or different from each other. In the compound represented by the general formula (1), it is preferred that at least one of $R^1$ to $R^4$ represents a substituted or unsubstituted diarylamino group, and at least one of $R^5$ to $R^8$ represents a substituted or unsubstituted diarylamino group. In particular, it is preferred that at least $R^3$ and $R^6$ each represent a substituted or unsubstituted diarylamino group.

Examples of the substituent on the diarylamino group include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an aryl-substituted amino group having from 12 to 40 carbon atoms, an acyl group having from 2 to 20 carbon atoms, an aryl group having from 6 to 40 carbon atoms, a heteroaryl group having from 3 to 40 carbon atoms, a substituted or unsubstituted carbazolyl group having from 12 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms, a substituted or unsubstituted dialkylamino group having from 1 to 10 carbon atoms, a substituted or unsubstituted diarylamino group having from 12 to 40 carbon atoms and a substituted or unsubstituted carbazolyl group having from 12 to 40 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted dialkylamino group having from 1 to 10 carbon atoms, a substituted or unsubstituted diarylamino group having from 12 to 40 carbon atoms, a substituted or unsubstituted aryl group having from 6 to 15 carbon atoms and a substituted or unsubstituted heteroaryl group having from 3 to 12 carbon atoms.

All $R^1$ to $R^8$ other than a substituted or unsubstituted diarylamino group each may be a hydrogen atom, and at least one of them may be a substituent. Two or more of them each are a substituent, the plural substituents may be the same as or different from each other. Examples of the substituent include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms and a substituted or unsubstituted heteroaryl group having from 3 to 12 carbon atoms.

In the general formula (1), $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure. The cyclic structure may be an aromatic ring or an aliphatic ring, and may contain a hetero atom. The cyclic structure may be a condensed ring containing two or more rings. The hetero atom herein is preferably one selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring and a cycloheptene ring.

The compound represented by the general formula (1) preferably has a structure represented by the following general formula (2).

In the general formula (2), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group. For the substituted or unsubstituted diarylamino group, the substituent capable of being represented by $R^1$ to $R^8$, and the substituent capable of being represented by $R^{11}$ to $R^{24}$, reference may be made to the substituted or unsubstituted diarylamino group, the substituent capable of being represented by $R^1$ to $R^8$, and the substituent capable of being represented by $Ar^1$ to $Ar^3$, in the general formula (1).

In the general formula (2), $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, and $R^{23}$ and $R^{24}$ each may be bonded to each other to form a cyclic structure. For the description and the preferred ranges of the cyclic structure, reference may be made to the corresponding descriptions in the general formula (1).

Examples of the preferred group of compounds represented by the general formula (2) include a group of compounds, in which at least one of $R^1$ to $R^4$ represents a substituted or unsubstituted diarylamino group, and at least one of $R^5$ to $R^8$ represents a substituted or unsubstituted diarylamino group, and a group of compounds, in which $R^3$ and $R^6$ each represent a substituted or unsubstituted diarylamino group.

Specific examples of the compound represented by the general formula (1) are shown below, but the compound represented by the general formula (1) capable of being used in the invention is not construed as being limited to the specific examples. In the following example compounds, Ph represents a phenyl group.

[chem 6]

Compound 1

[chem 5]

General Formula (2)

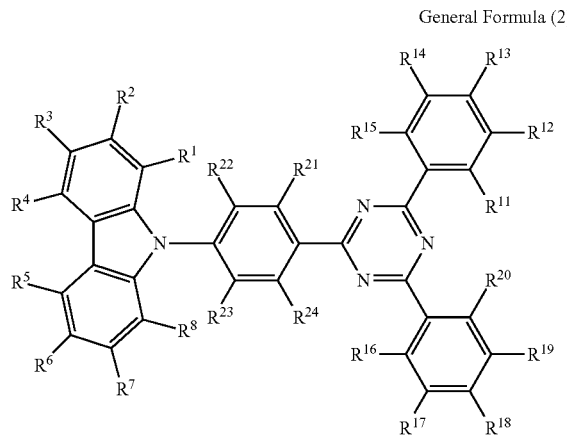

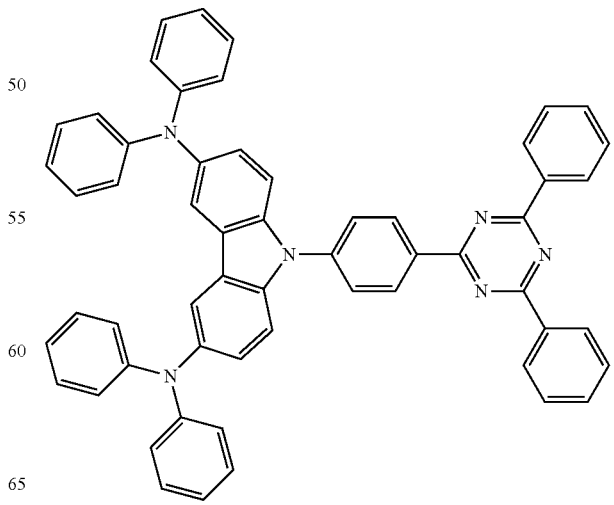

Compound 2
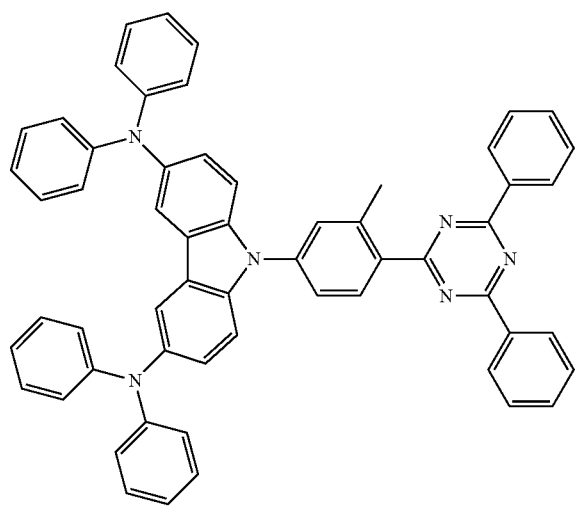
Compound 3
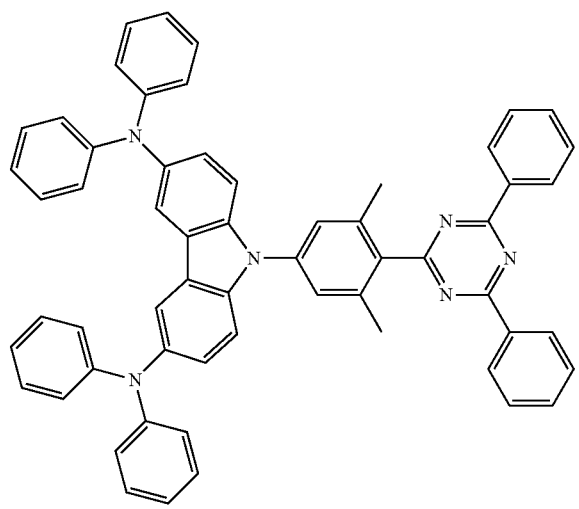
[chem 7]
Compound 4
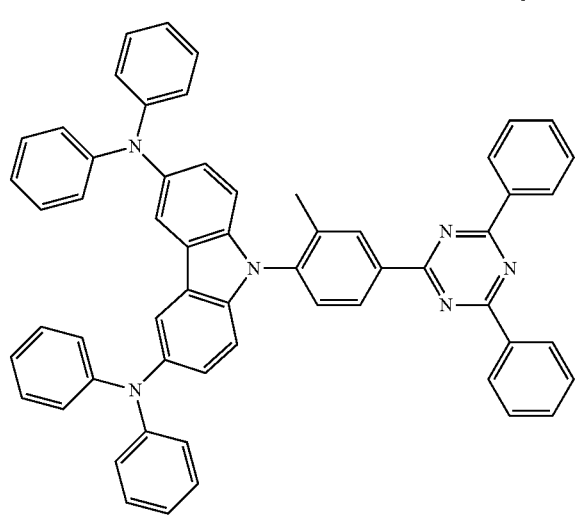
Compound 5
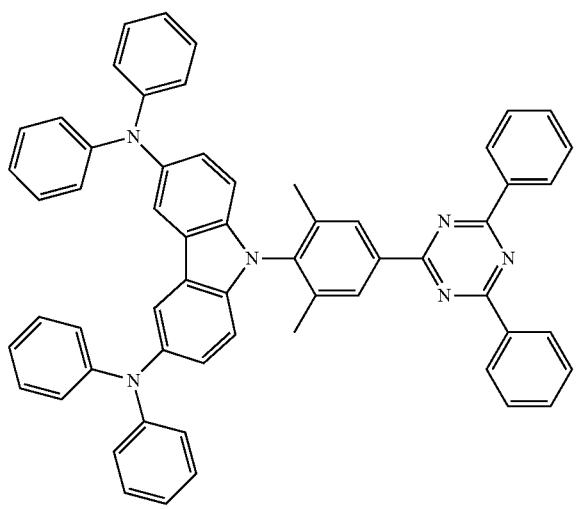
Compound 6
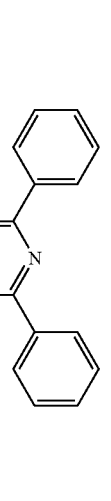
[chem 8]
Compound 7
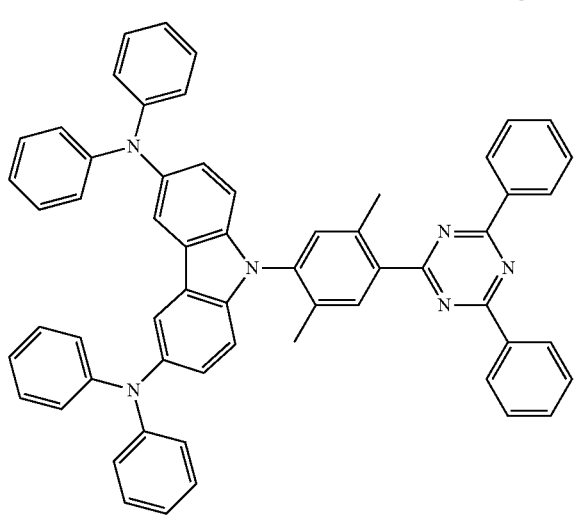

-continued

Compound 8

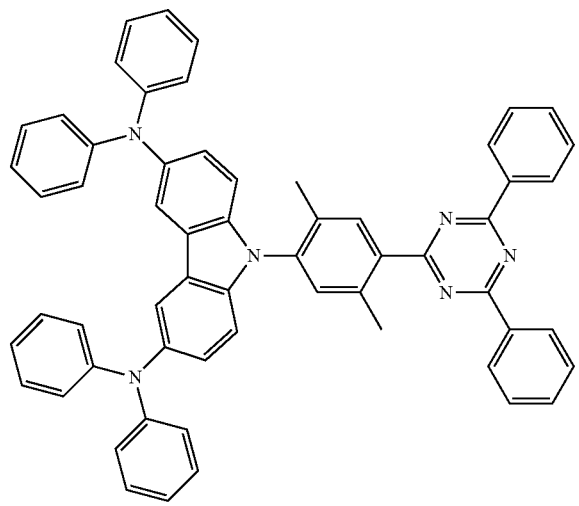

Compound 9

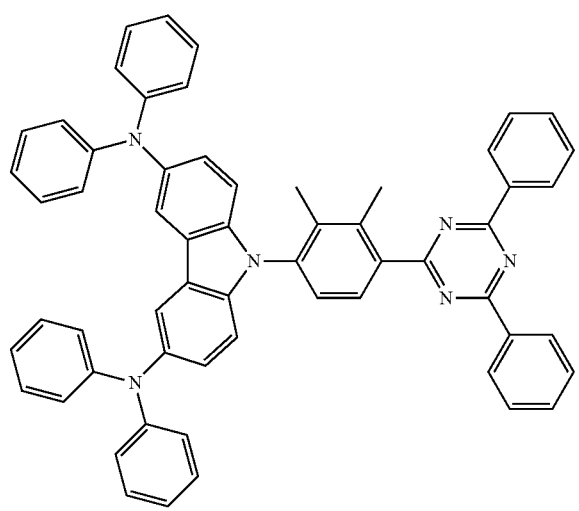

[chem 9]

Compound 10

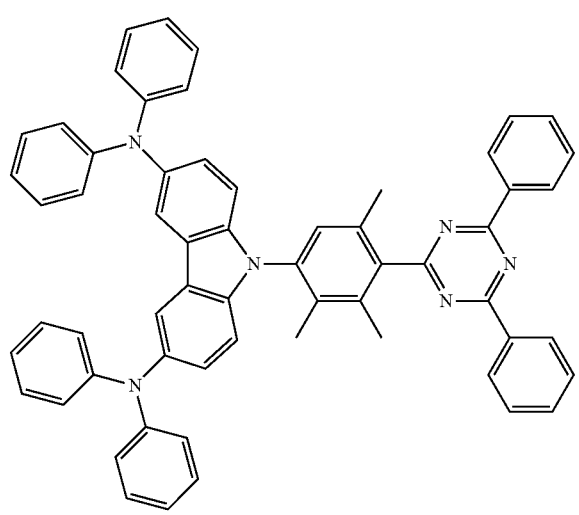

-continued

Compound 11

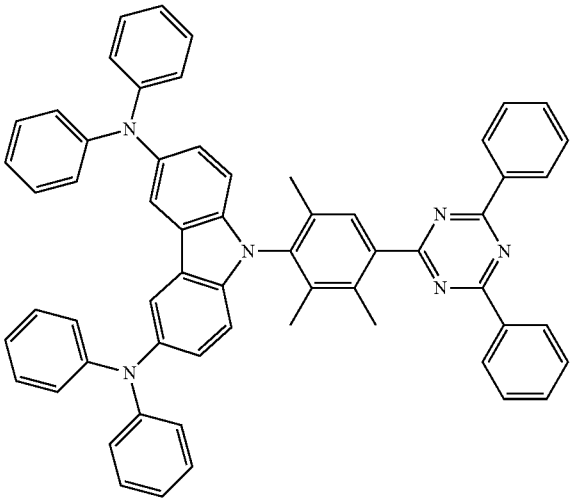

Compound 12

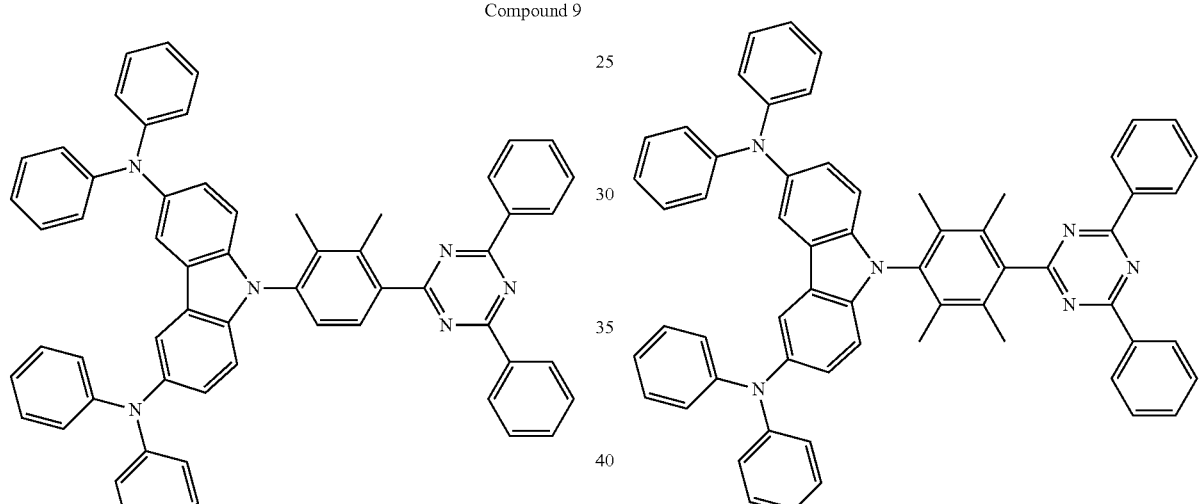

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of $Ar^1$ to $Ar^3$ and $R^1$ to $R^8$ in the general formula (1) is prepared, and is homopolymerized or copolymerized with another monomer to prepare a polymer containing repeating units, and the polymer is used as a light emitting material. In alternative, it may be considered that the compounds represented by the general formula (1) are coupled to form a dimer or a trimer, and the dimer or the trimer is used as a light emitting material.

Examples of the polymer having the repeating unit containing the structure represented by the general formula (1) include a polymer containing a structure represented by the following general formula (3) or (4).

[chem 10]

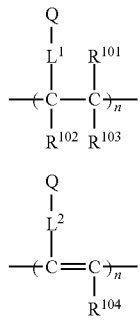

General Formula (3)

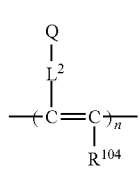

General Formula (4)

In the general formulae (3) and (4), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (3) and (4), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $Ar^1$ to $Ar^3$ and $R^1$ to $R^8$ in the structure represented by the general formula (1) constituting Q or any of $R^1$ to $R^8$ and $R^{11}$ to $R^{24}$ in the structure represented by the general formula (2). Two or more of the linking groups may be boded to one group represented by Q to form a cross-linked structure or a network structure.

Specific examples of the structure of the repeating unit include structures represented by the following formulae (5) to (8).

[chem 11]

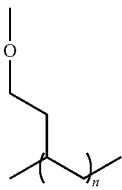

Formula (5)

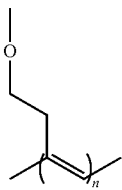

Formula (6)

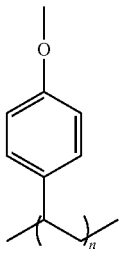

Formula (7)

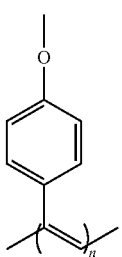

Formula (8)

The polymer having the repeating unit containing the structure represented by any of the formulae (5) to (8) may be synthesized in such a manner that a hydroxyl group is introduced to any of $Ar^1$ to $Ar^3$ and $R^1$ to $R^8$ in the structure represented by the general formula (1), and the hydroxyl group as a linker is reacted with the following compound to introduce a polymerizable group thereto, followed by polymerizing the polymerizable group.

[chem 12]

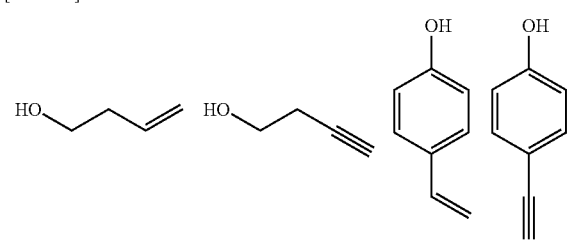

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Synthesis Method of Compound Represented by General Formula (1)

The compound represented by the general formula (1) may be synthesized by combining the known reactions. For example, the compound may be synthesized through the following scheme.

[chem 13]

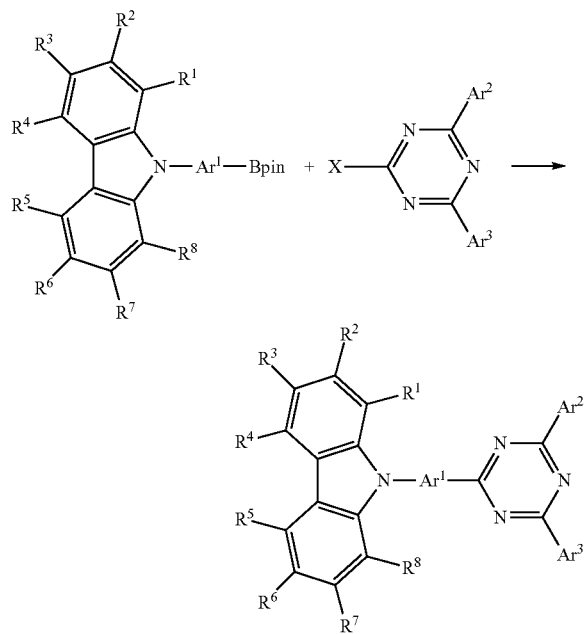

In the aforementioned reaction scheme, for the descriptions of $Ar^1$ to $Ar^3$ and $R^1$ to $R^8$, reference may be made to the corresponding descriptions in the general formula (1). In the reaction scheme, pin represents a pinacolato group, and X represents a halogen atom, examples of which include a fluorine atom, a chlorine atom, a bromine atom and an iodine atom, with a chlorine atom and a bromine atom being preferred.

The reaction shown by the reaction scheme is an application of the known coupling reaction, and the known reaction conditions may be appropriately selected and used. The carbazole derivative as the starting material may be synthesized by utilizing the known synthesis method, in which a corresponding bromide is reacted with bis(pinacolato)diboron. For the details of the reaction and the synthesis route, reference may be made to the synthesis examples described later. The compound represented by the general formula (1) may also be synthesized by combining the other known synthesis reactions.

Organic Light Emitting Device

The compound represented by the general formula (1) of the invention is useful as a light emitting material of an organic light emitting device. Accordingly, the compound represented by the general formula (1) of the invention may be effectively used as a light emitting material in a light emitting layer of an organic light emitting device. The compound represented by the general formula (1) includes a delayed fluorescent material emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light emitting device that uses the compound as a light emitting material has features that the device emits delayed fluorescent light and has high light emission efficiency. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent emitter emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent emitter emitting light through absorption of thermal energy is particularly useful for an organic electroluminescent device. In the case where a delayed fluorescent emitter is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited single state has the same wavelength as fluorescent light since it is light emission from the excited single state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited single state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light emitting material of a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy level that is between the lowest excited singlet energy level of the host material contained in the light emitting layer and the lowest excited singlet energy level of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitting material may be solely used as the light emitting layer, but the light emitting layer preferably contains a light emitting material and a host material. The light emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light emitting material are confined in the light emitting material. Accordingly, a host material is preferably used in addition to the light emitting material in the light emitting layer. The host material used may be an organic compound that has excited singlet energy and excited triplet energy, at least one of which is higher than those of the light emitting material of the invention. As a result, the singlet excitons and the triplet excitons generated in the light emitting material of the invention are capable of being confined in the molecules of the light emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitting material of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light emitting layer but also in the other layers than the light emitting layer. In this case, the compound represented by the general formula (1) used in the light emitting layer and the compound represented by the general formula (1) used in the other layers than the light emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_1$ to $R_{10}$ each independently represent a hydrogen atom or a substituent, and n represents an integer of from 3 to 5.

Preferred examples of a compound that may also be used as the host material of the light emitting layer are shown below.

[chem. 14]

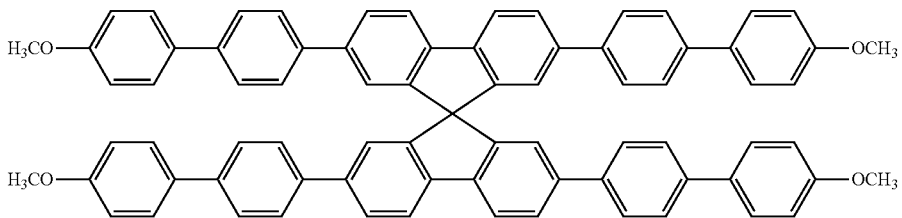

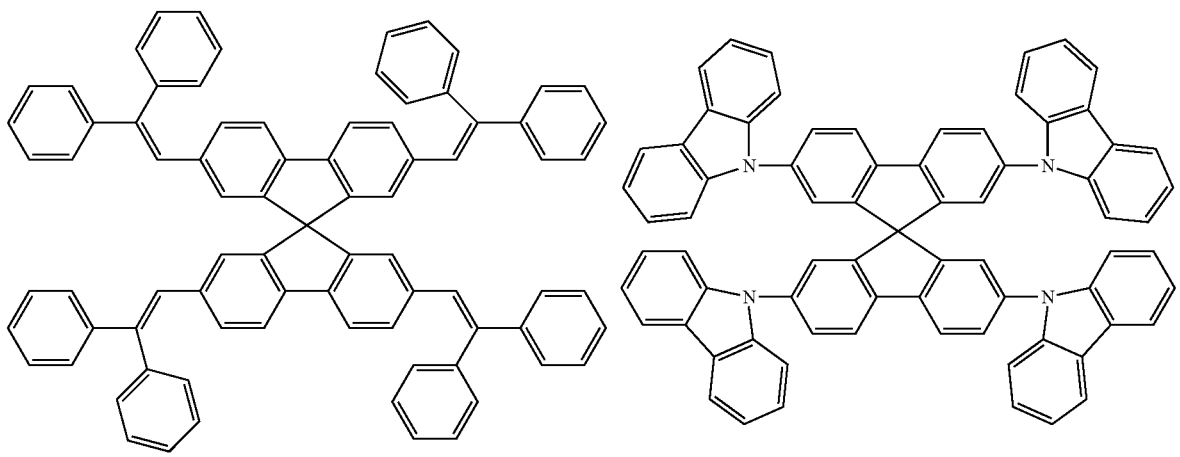

-continued
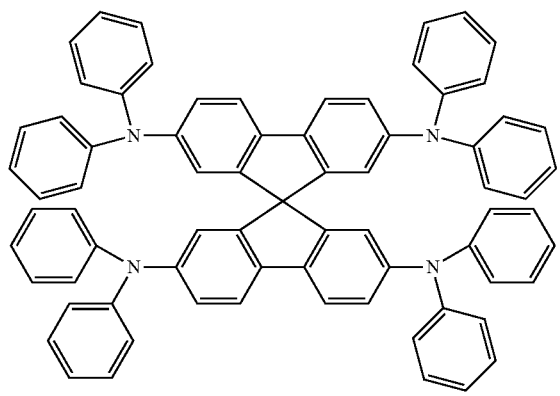
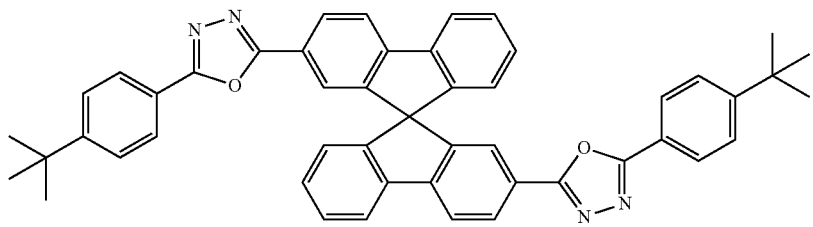
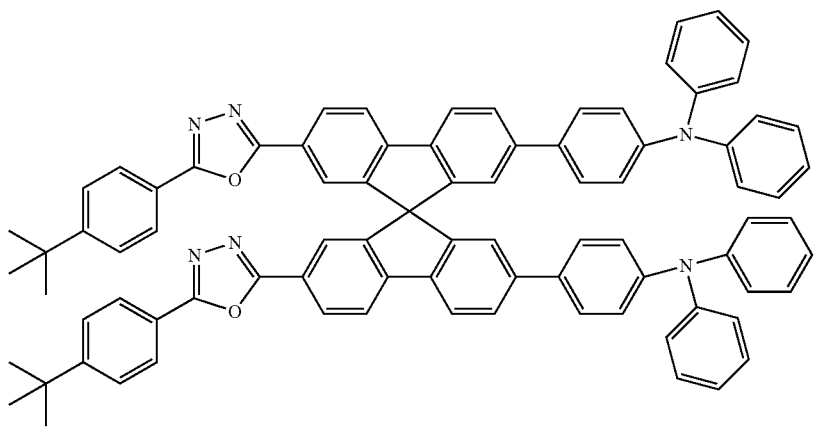
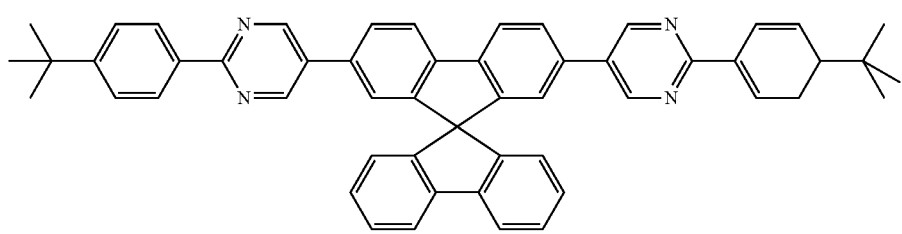
[chem 15]
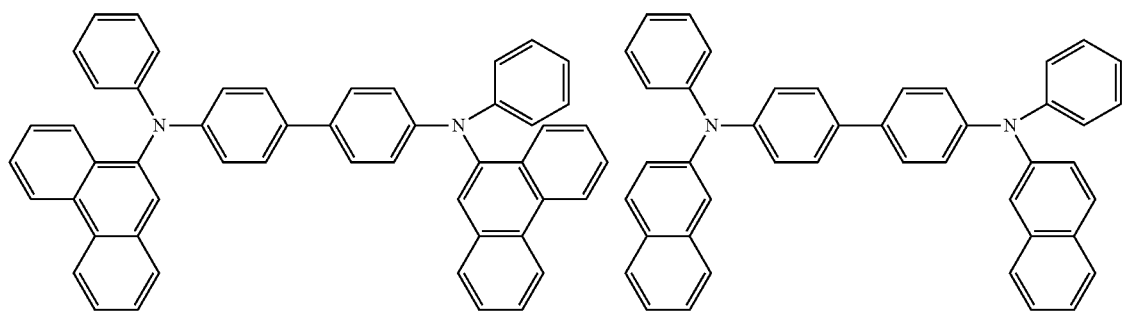

-continued
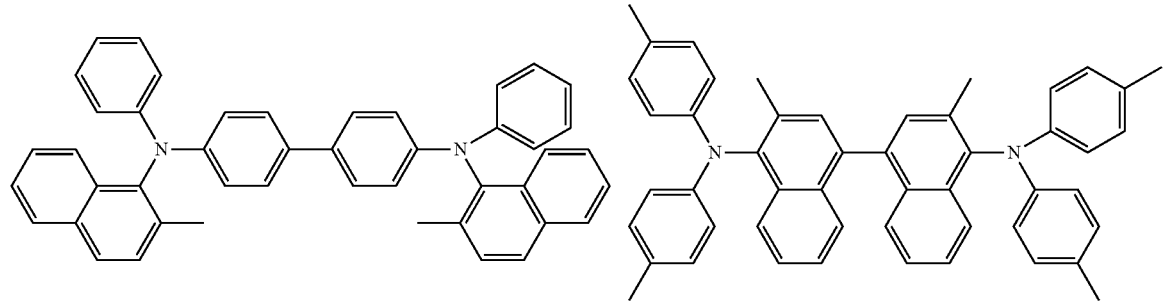
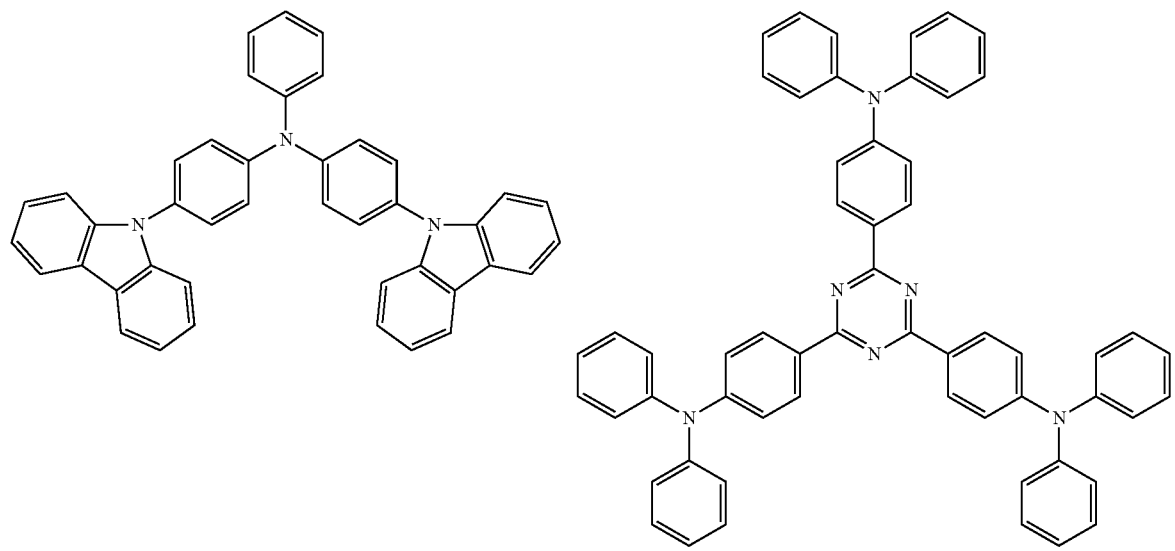
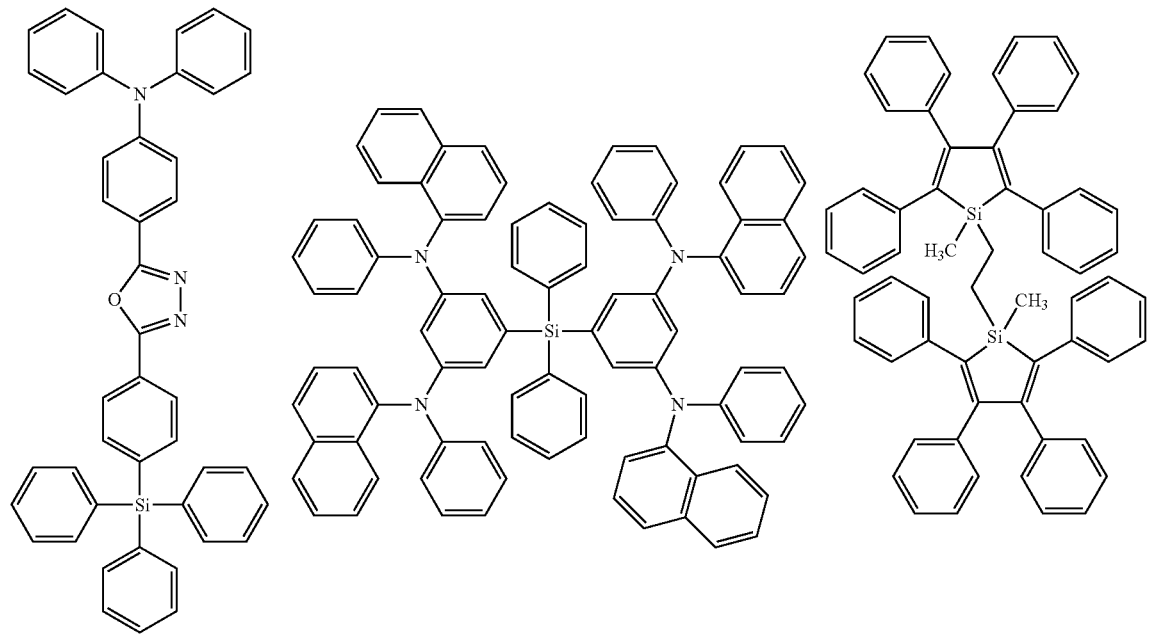

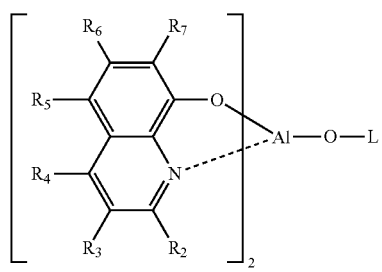 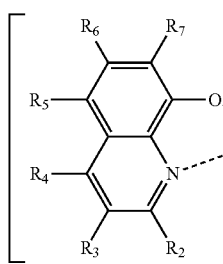 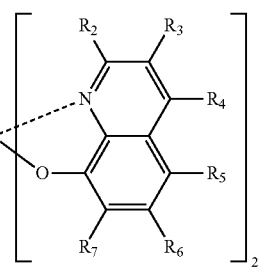
[chem 16]
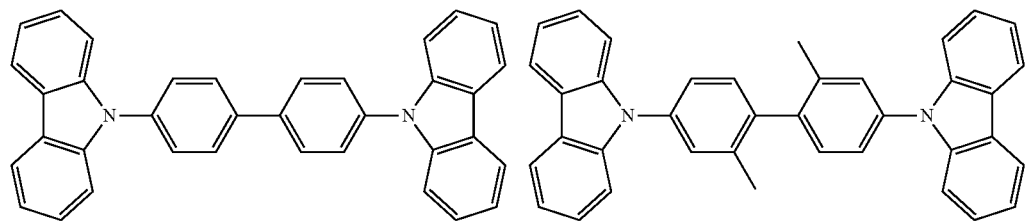
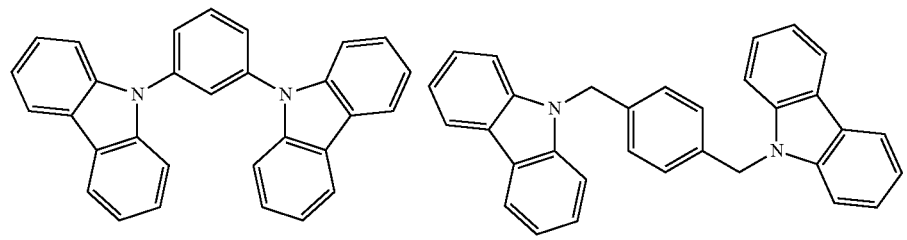
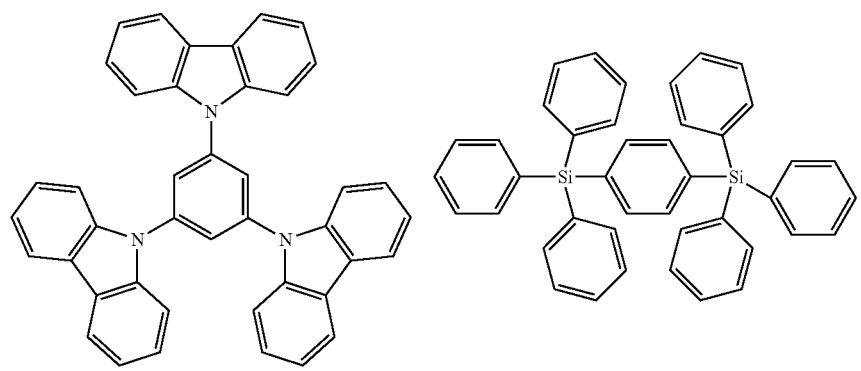
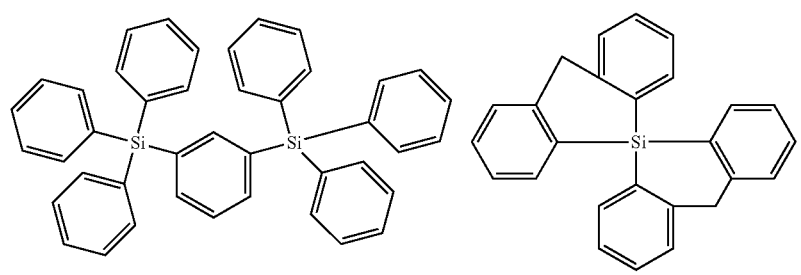

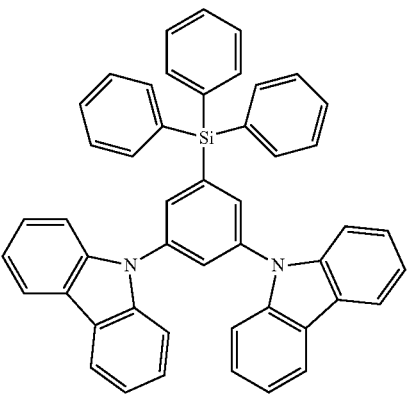
[chem 17]
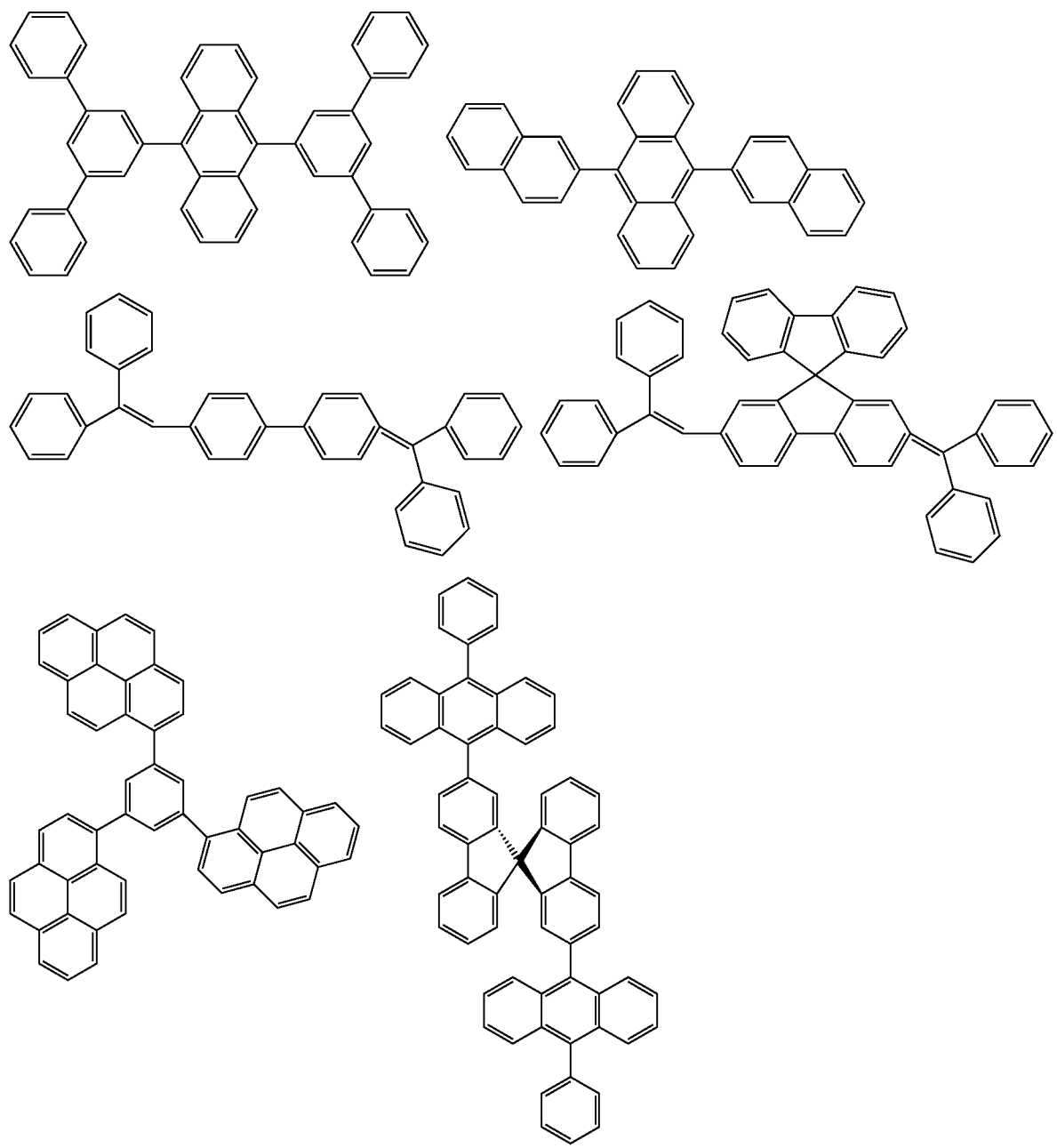

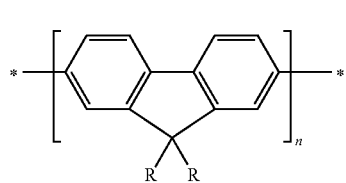 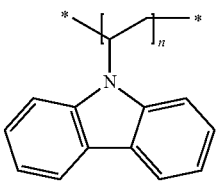 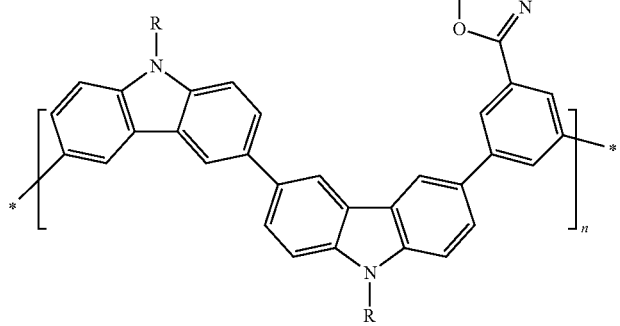
[chem 18]
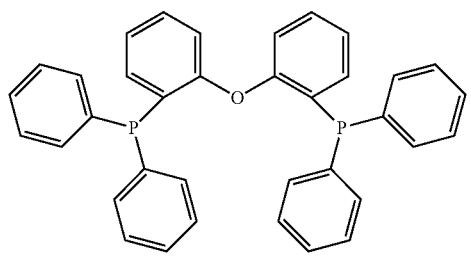
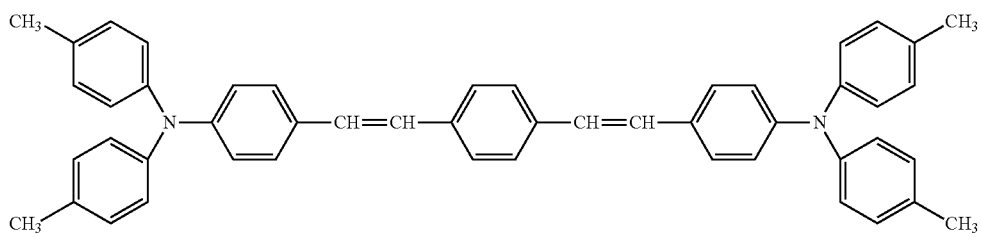
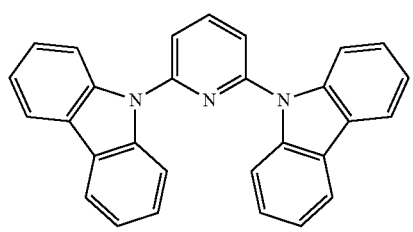 [SMILES: c1cc(-n2c3ccccc3c3ccccc32)nc(-n2c3ccccc3c3ccccc32)c1]
Preferred examples of a compound that may be used as the hole injection material are shown below.

[chem 19]
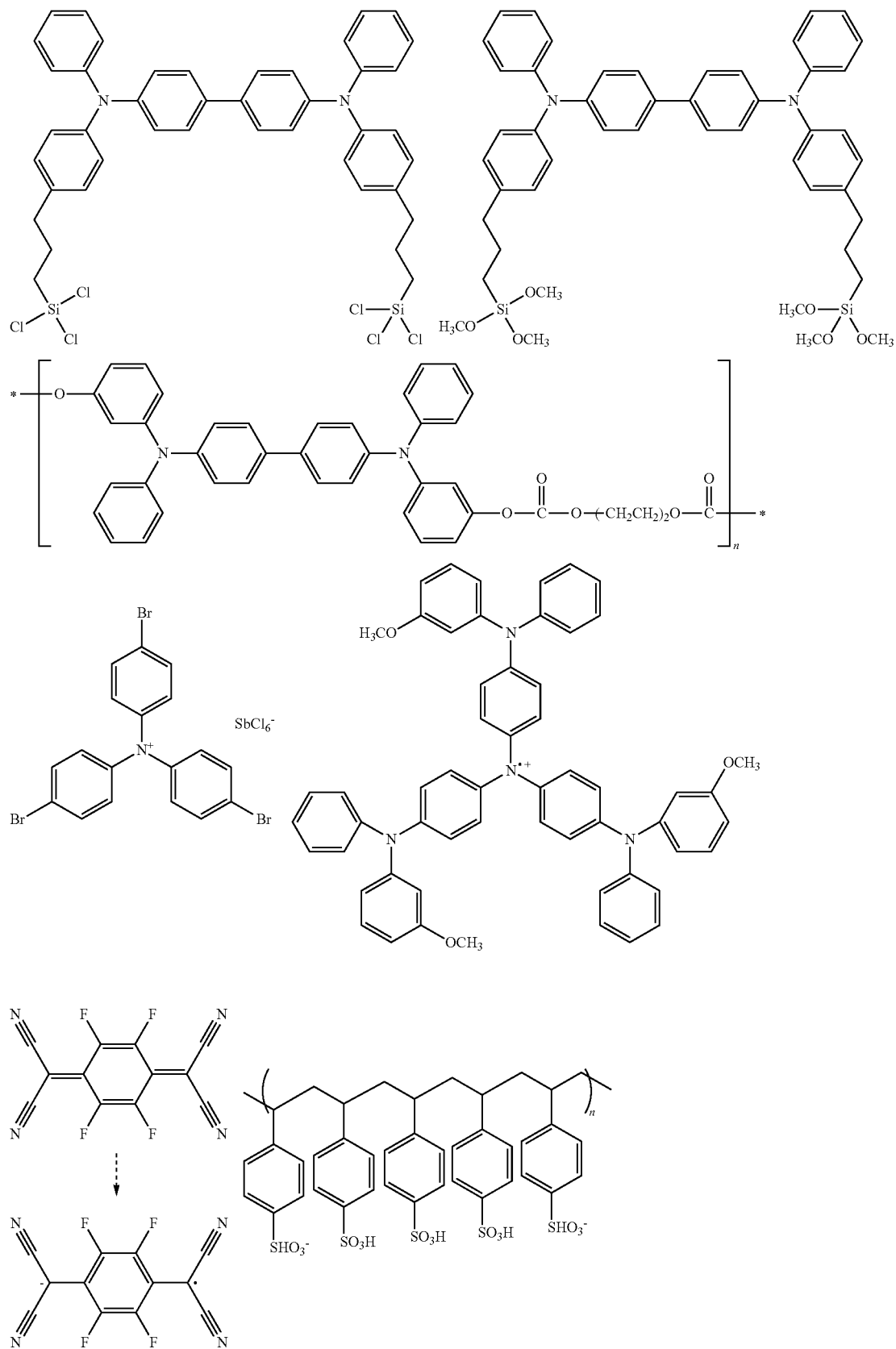

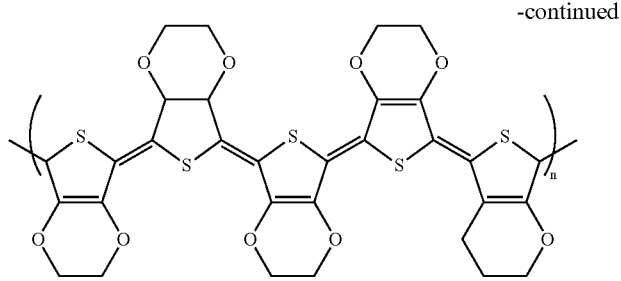
Preferred examples of a compound that may be used as the hole transporting material are shown below.
[chem 20]
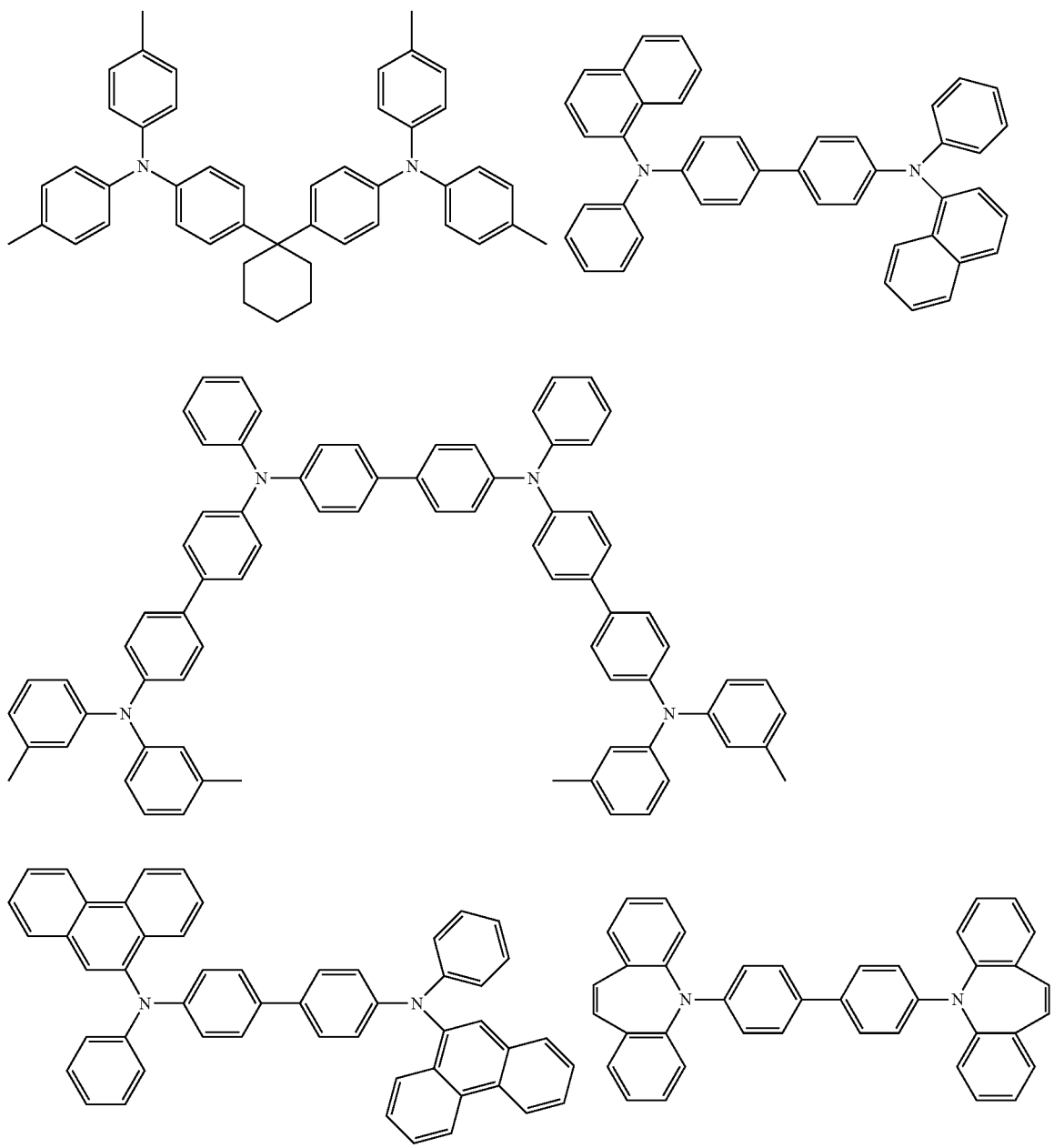

[chem 21]
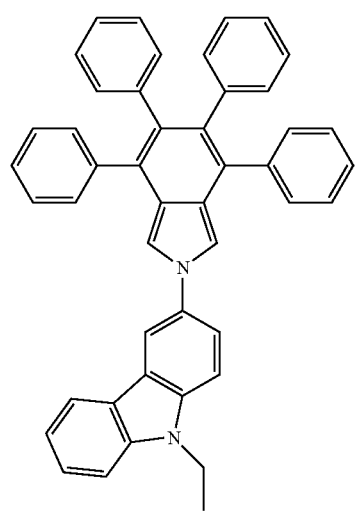
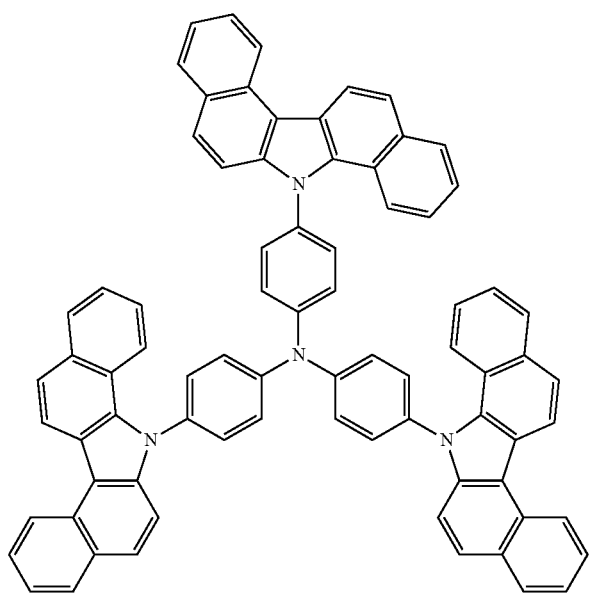
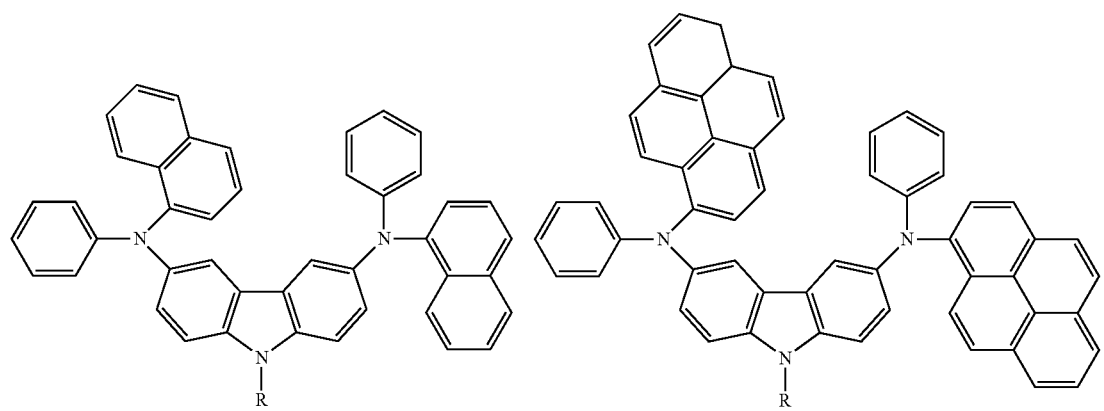
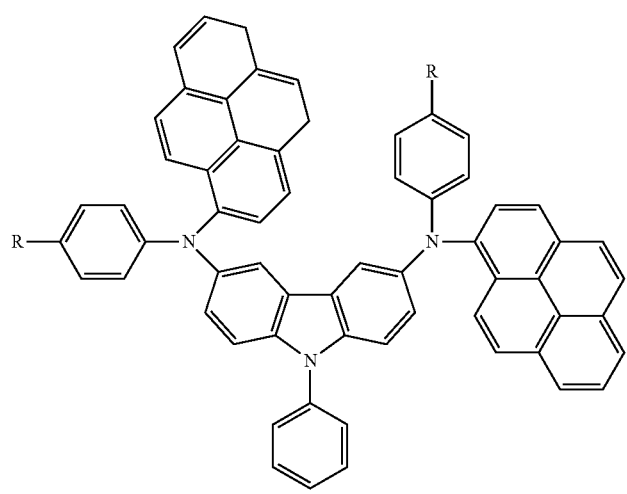

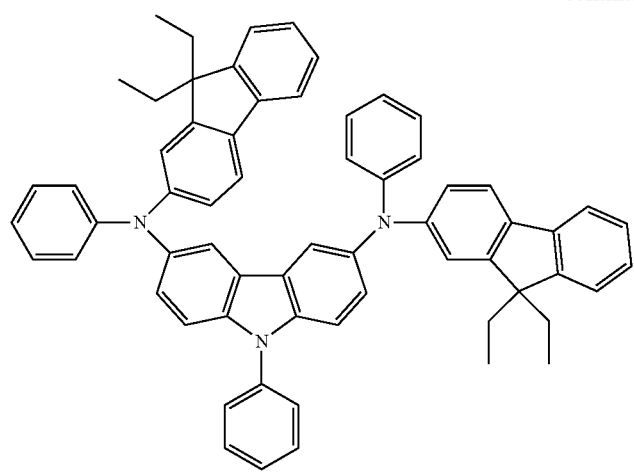
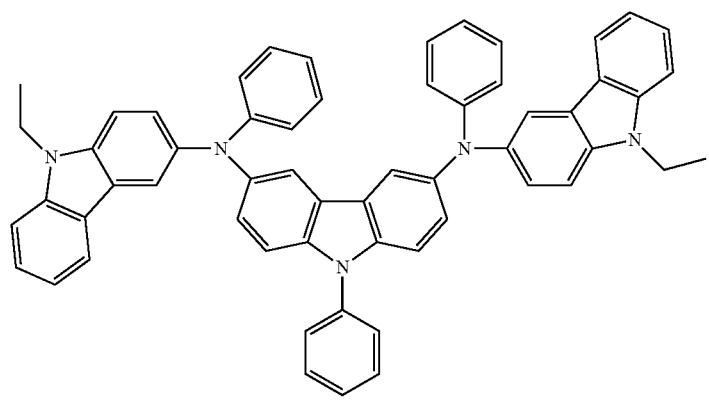
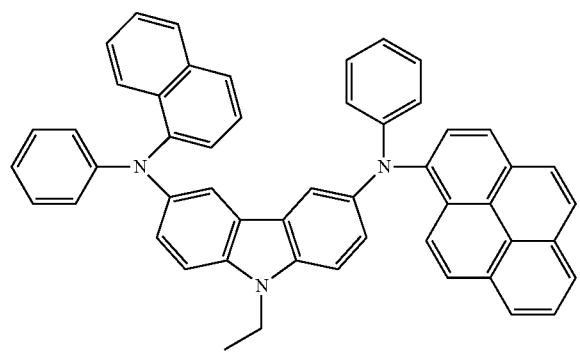

[chem 22]
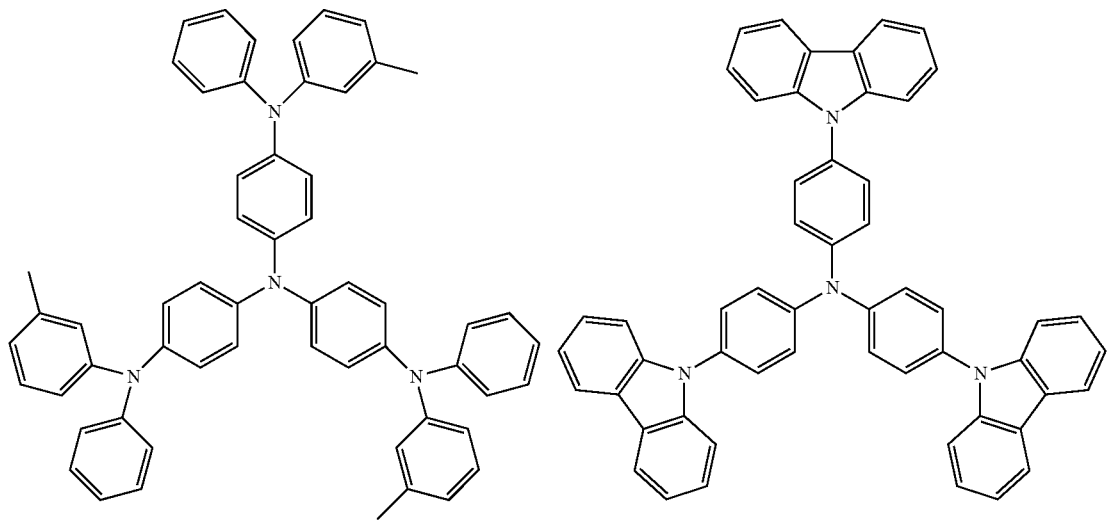
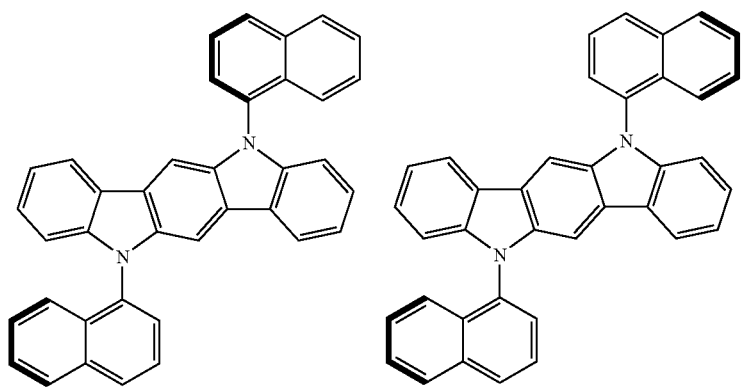
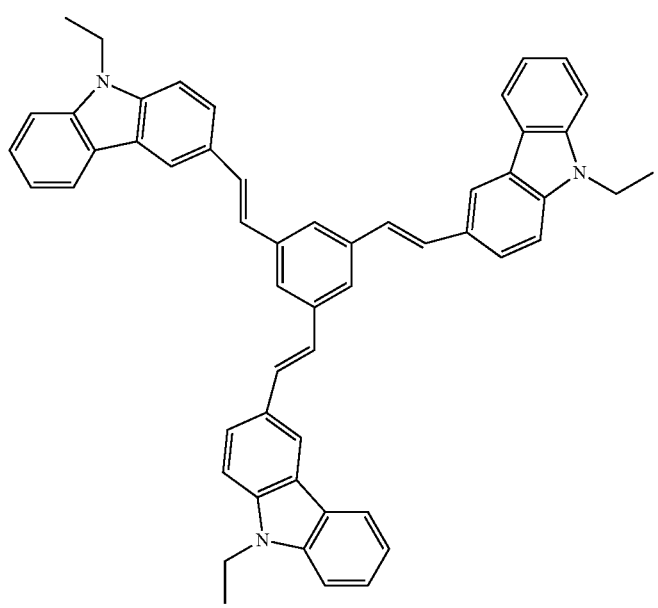

-continued
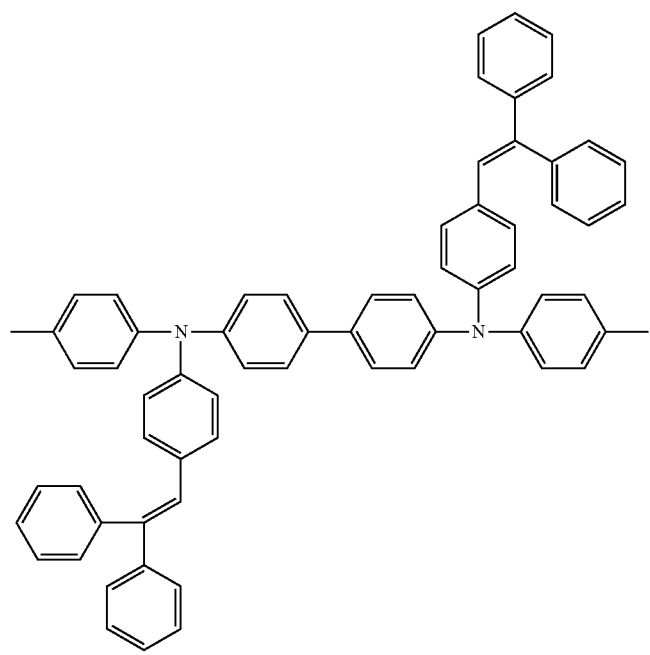
[chem 23]
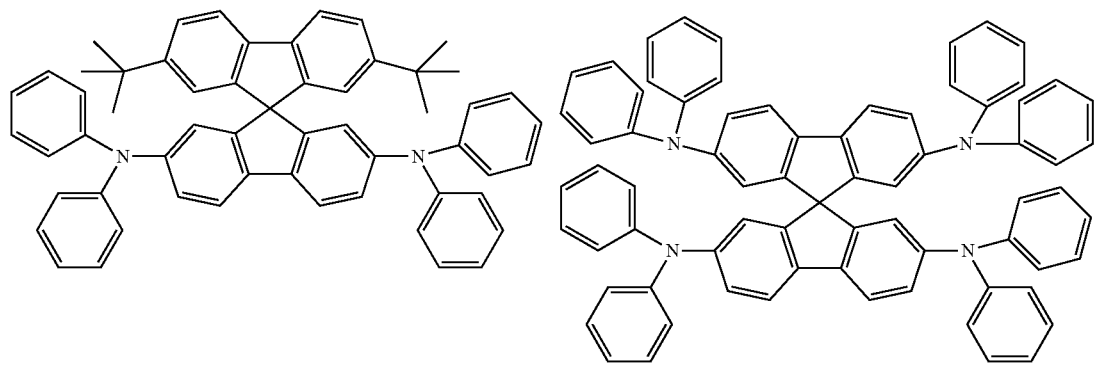
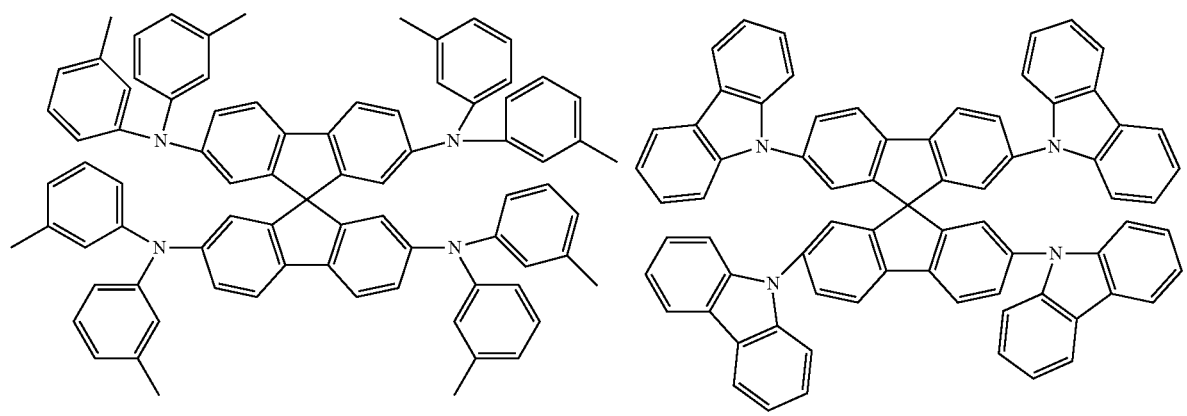
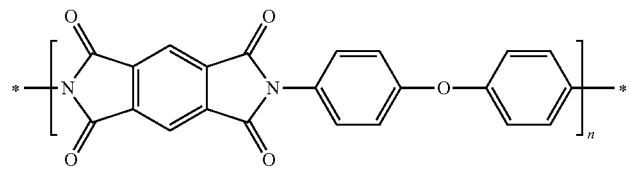

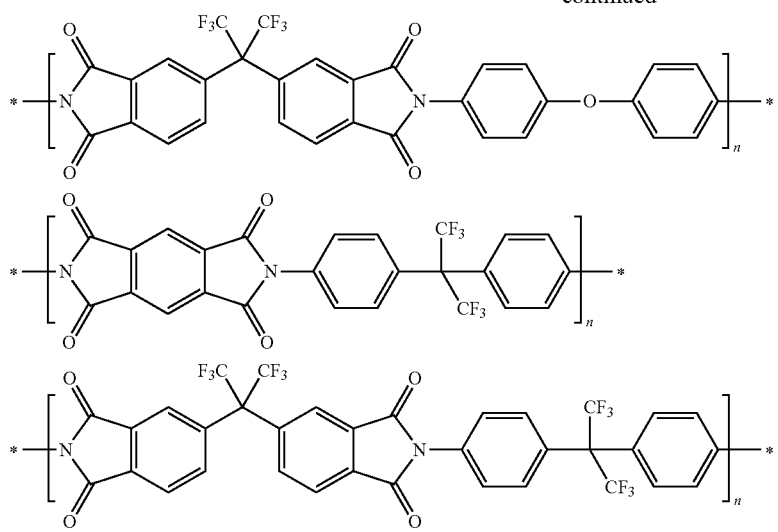
[chem 24]
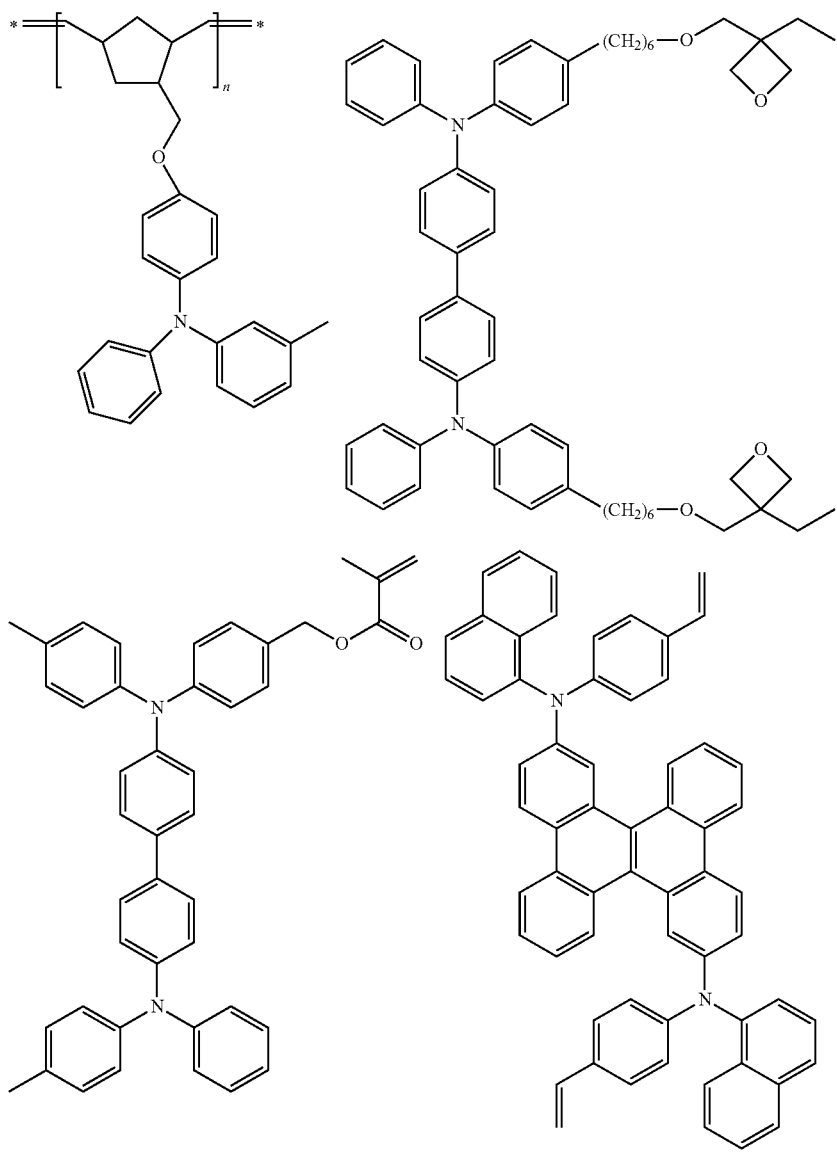

R =
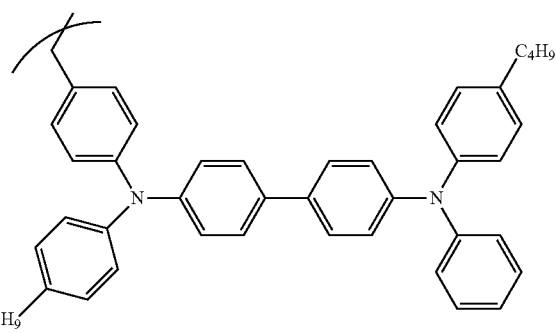
[chem 25]
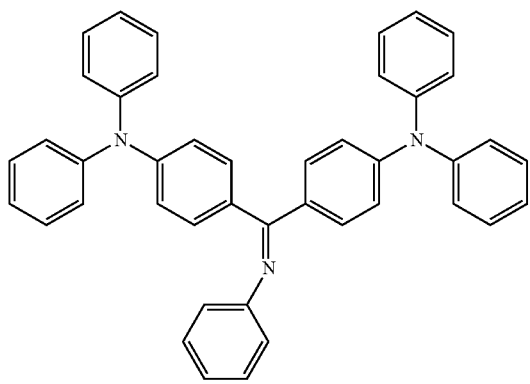
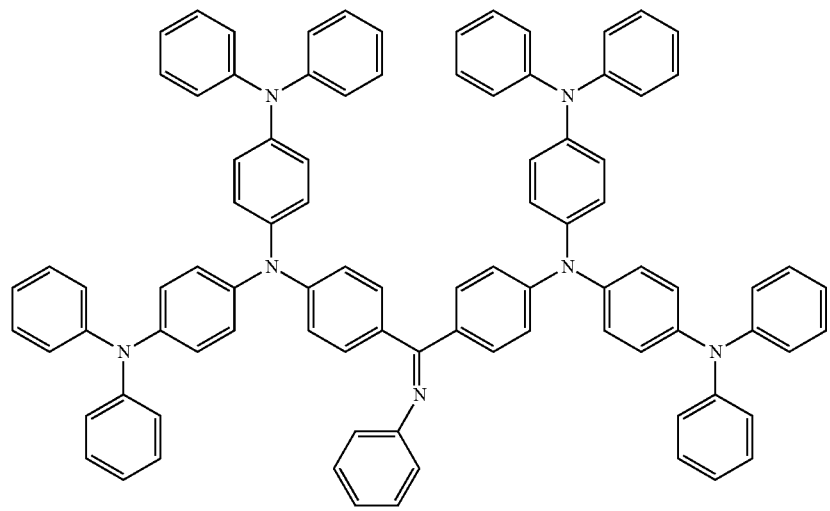

-continued
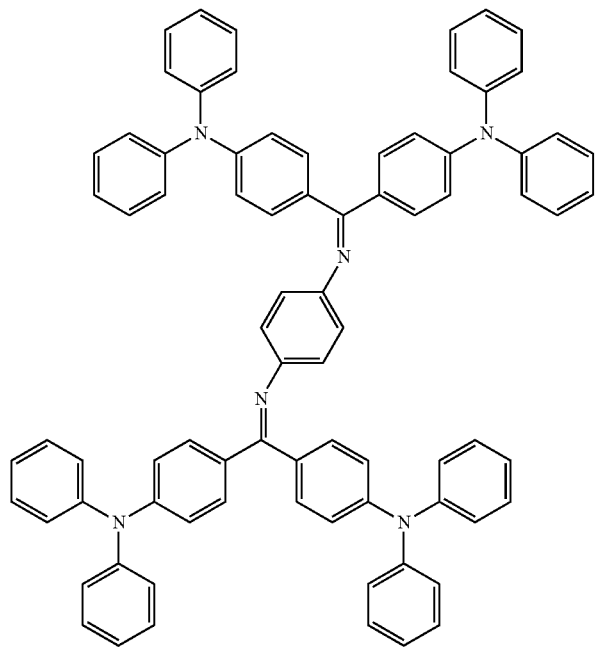
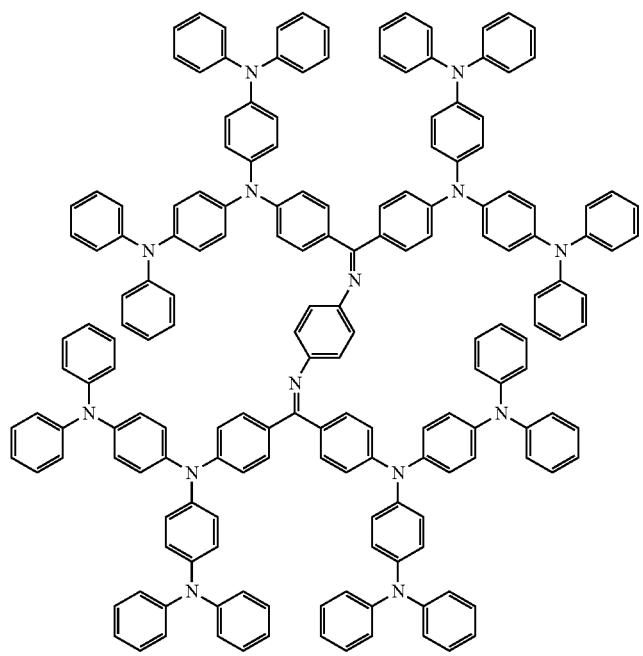

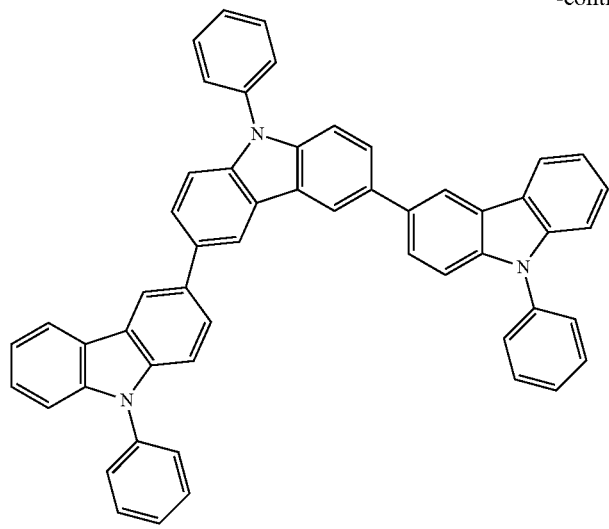
Preferred examples of a compound that may be used as the electron barrier material are shown below.
[chem 26]
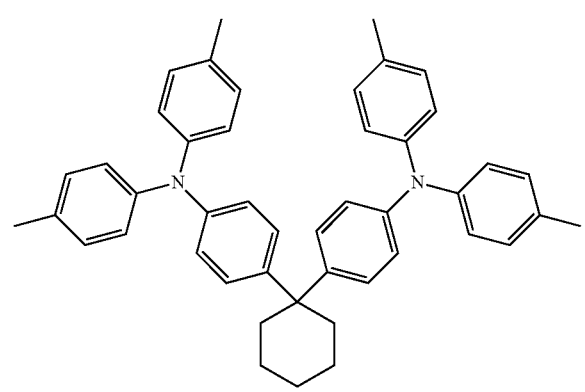
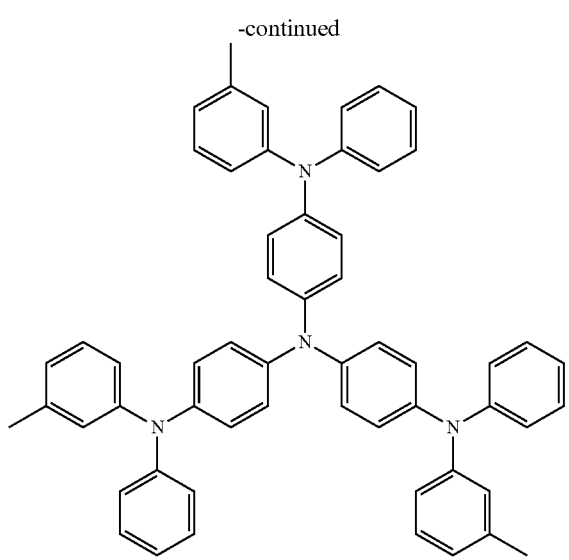
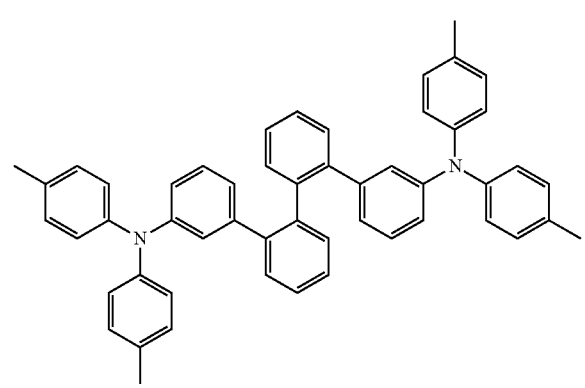
Preferred examples of a compound that may be used as the hole barrier material are shown below.

[chem 27]
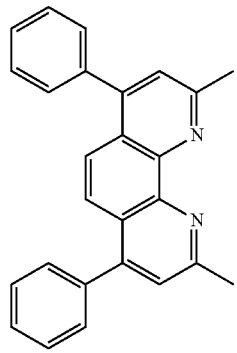
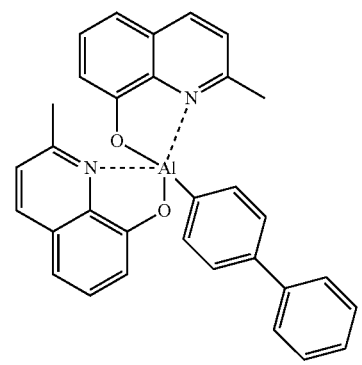
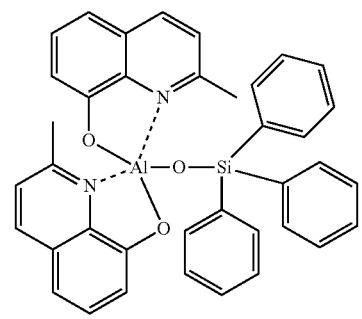
-continued
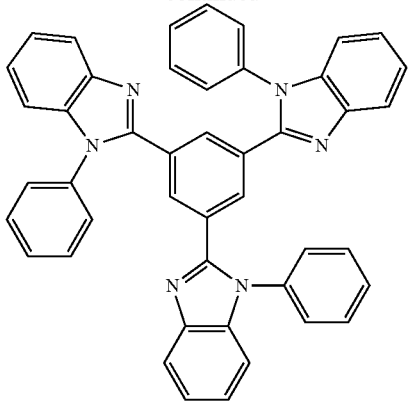
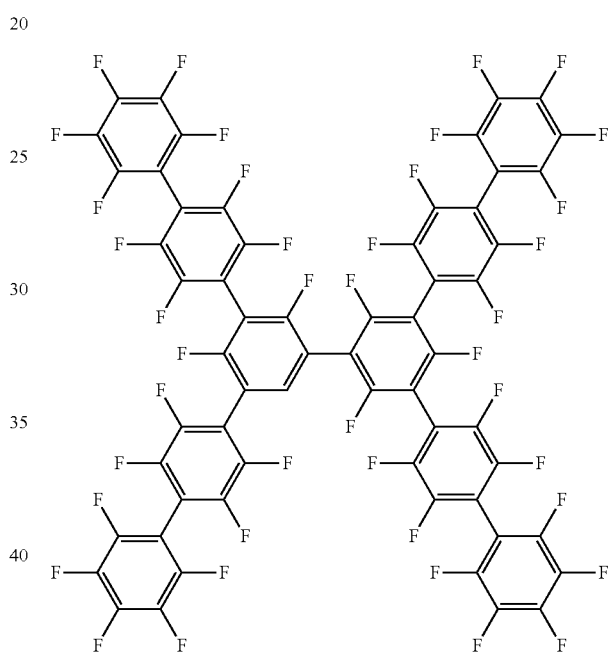
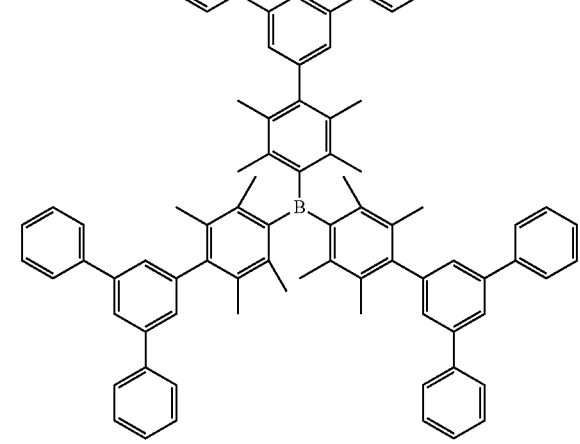

57
-continued
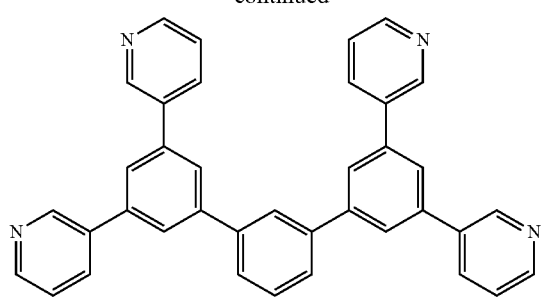
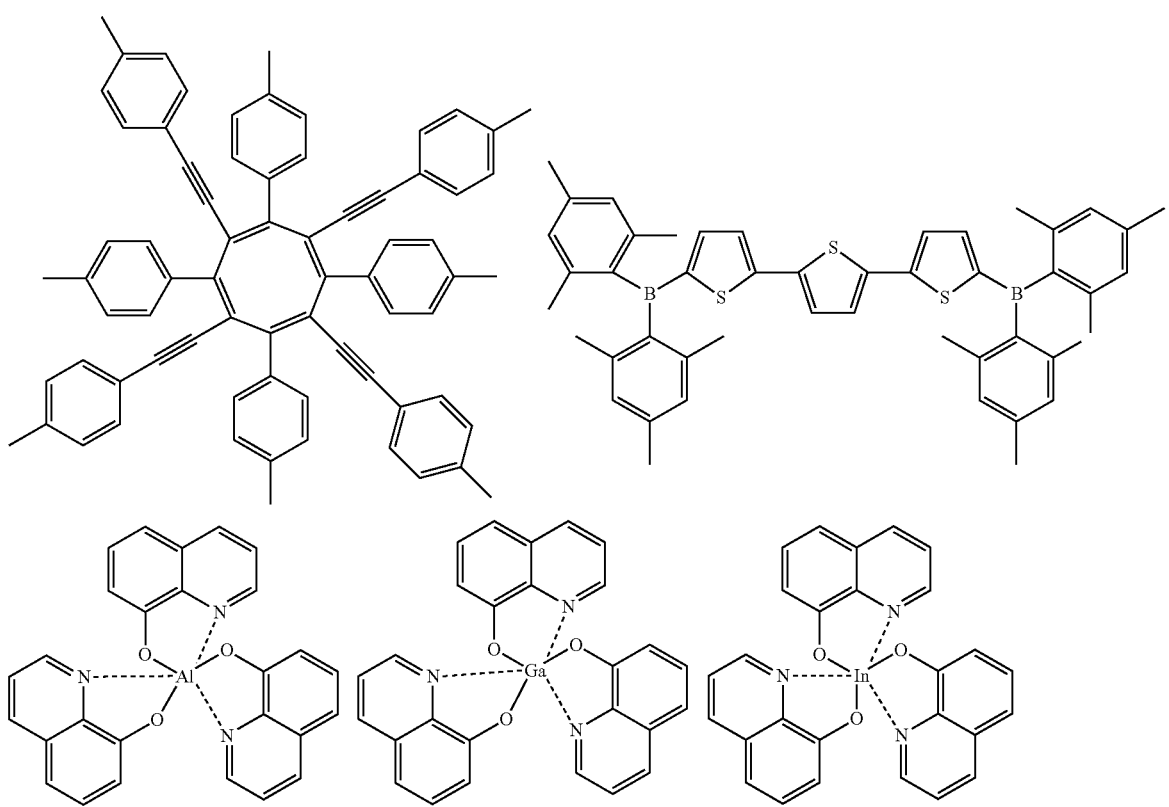
58
-continued
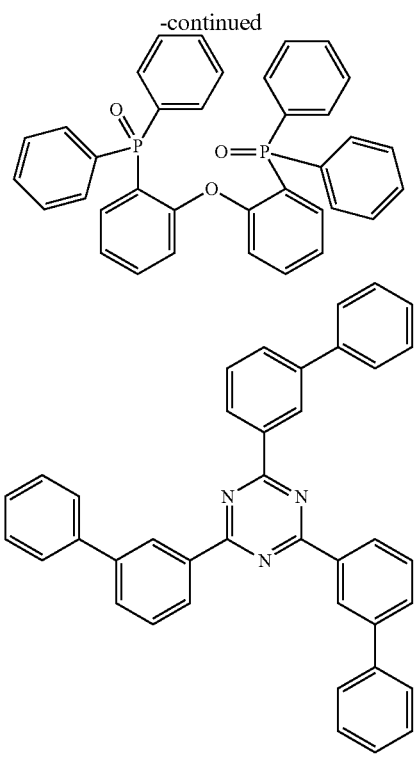
Preferred examples of a compound that may be used as the electron transporting material are shown below.
[chem 28]

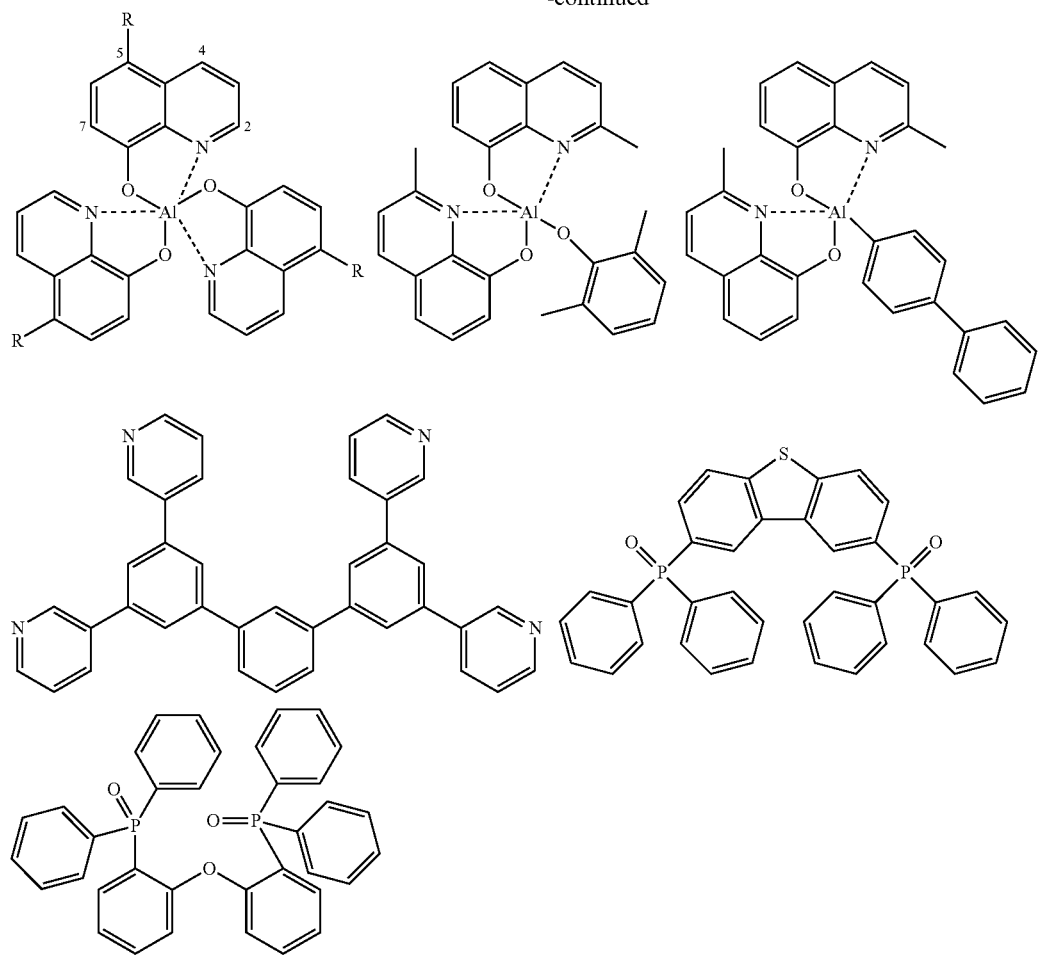
[chem 29]
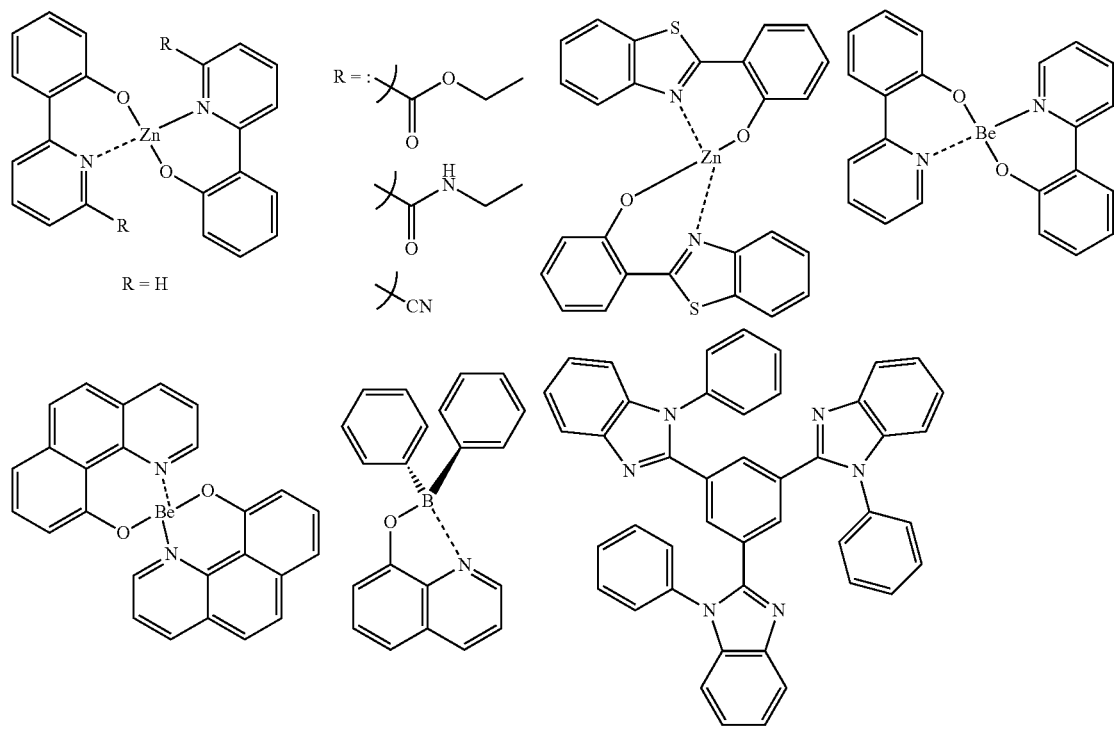

-continued
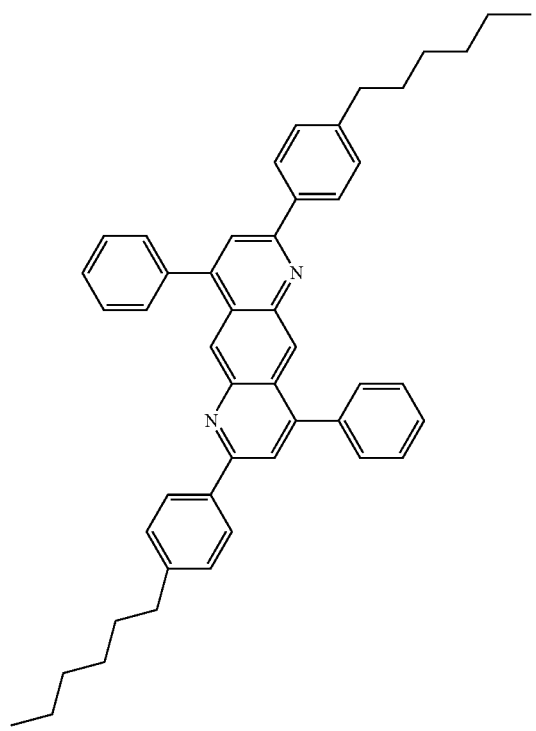
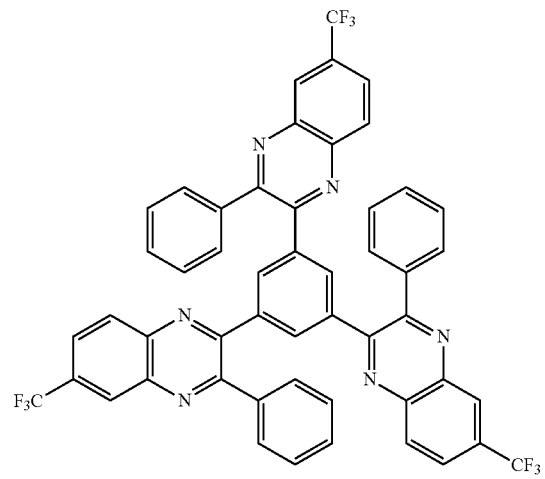
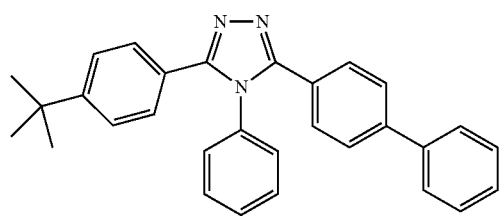
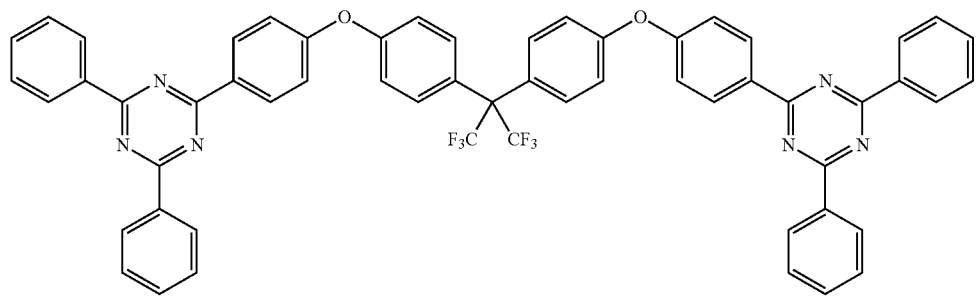
[chem 30]
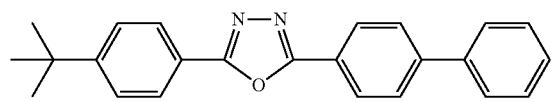

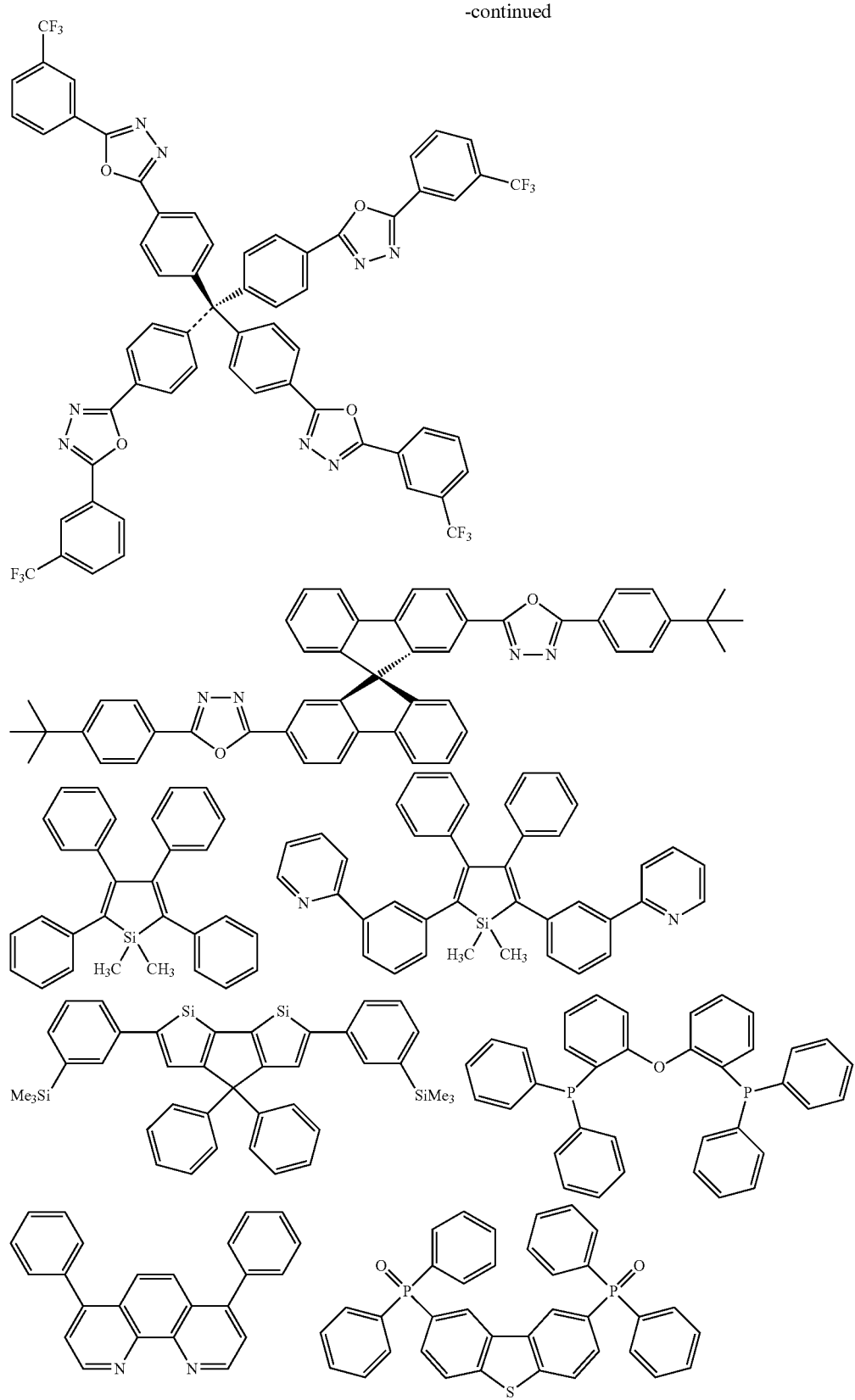
Preferred examples of a compound that may be used as the electron injection material are shown below.

[chem 31]

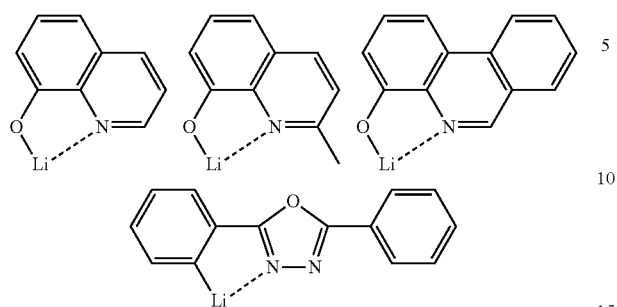

Preferred examples of a compound as a material that may be added are shown below. For example, the compound may be added as a stabilizing material.

[chem 32]

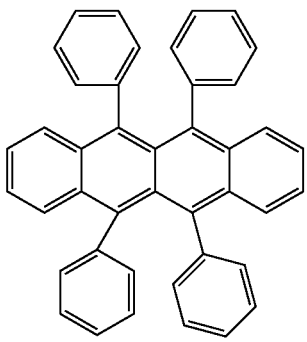

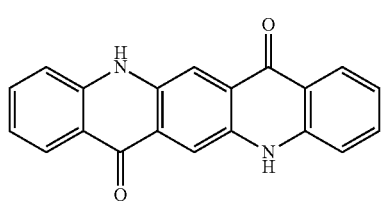

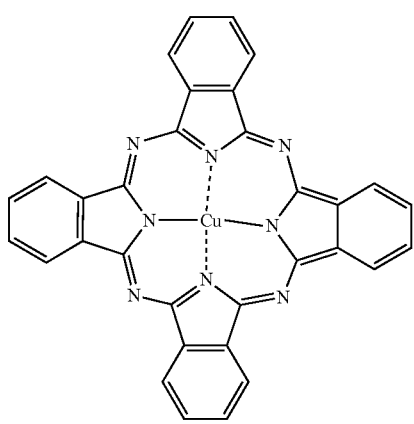

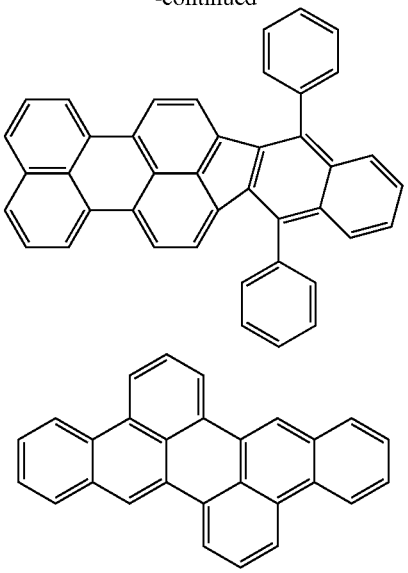

The organic electroluminescent device thus produced by the aforementioned method emits light on application of an electric field between the anode and the cathode of the device. In this case, when the light emission is caused by the excited single energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the compound represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using Source Meter (2400 Series, produced by Keithley Instruments Inc.), Semiconductor Parameter Analyzer (E5273A, produced by Agilent Technologies, Inc.), Optical Power Meter (1930C, produced by Newport Corporation), Optic Spectrometer (USB2000, produced by Ocean Optics, Inc.), Spectral Radient Meter (SR-3, produced by Topcon Corporation) and Streak Camera (Model C4334, produced by Hamamatsu Photonics K.K.).

Synthesis Example 1

Synthesis of Compound 1

[chem 33]

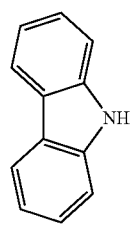

Intermediate 1 benzylchloride
KOH
───────────→
THF (dry)
reflux

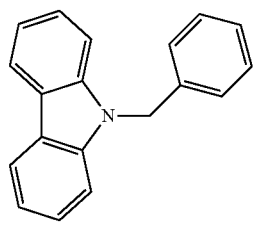

Intermediate 2

KI, KIO$_3$
H$_2$SO$_4$
───────────→
ethanol
55° C.

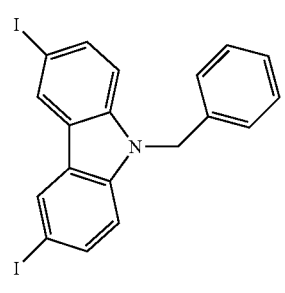

Intermediate 3 diphenylamine
Pd$_2$(dba)$_3$·CHCl$_3$
Sodium tert-butoxide
(t-Bu$_3$)PBF$_4$
───────────→
toluene (dry)
100° C.

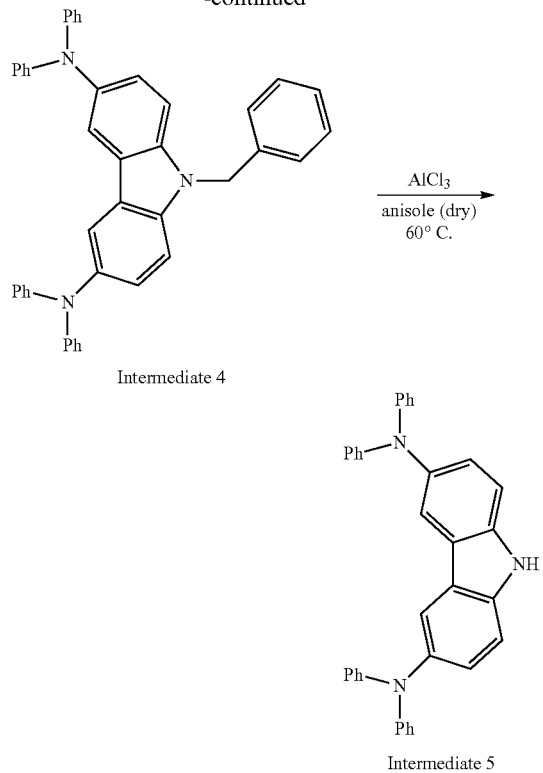

Intermediate 4

AlCl$_3$
───────────→
anisole (dry)
60° C.

Intermediate 5

A solution of carbazole (intermediate 1) (25.7 g 150 mmol, produced by Nacalai Tesque, Inc.), benzyl chloride (58.4 g, 454.5 mmol, produced by Wako Pure Chemical Industries, Ltd.) and potassium hydroxide (41.1 g, 714.3 mmol, produced by Nacalai Tesque, Inc.) in tetrahydrofuran (250 mL, produced by Kanto Chemical Co., Inc.) was refluxed in an argon atmosphere for 34 hours. Subsequently, after cooling at room temperature, water (250 mL) and dichloromethane (200 mL) were added to the reaction solution, and the mixture was separated. The organic layer was dried over anhydrous magnesium sulfate, from which the solvent was distilled off with an evaporator, and the product was recrystallized from hexane to provide an intermediate 2 in the form of white crystals (30.67 g, yield: 770). A solution of the intermediate 2 (5.1 g, 19.8 mmol), potassium periodate (3.6 g, 16.9 mmol, produced by Nacalai Tesque, Inc.), potassium iodide (4.4 g, 32.4 mmol, produced by Nacalai Tesque, Inc.) and sulfuric acid (3.1 g, 31.3 mmol, produced by Nacalai Tesque, Inc.) in ethanol (700 mL, produced by Wako Pure Chemical Industries, Ltd.) was heated to 55° C. in an argon atmosphere under shield of light for 13 hours. Subsequently, after cooling at room temperature, ethanol was distilled off with an evaporator, dichloromethane (300 mL) and water (200 mL) were added to the residue, and the mixture was separated. The organic layer was dried over anhydrous magnesium sulfate, from which the solvent was distilled off with an evaporator, and the product was recrystallized from a mixed solvent of ethyl acetate and hexane to provide an intermediate 3 in the form of white crystals (9.65 g, yield: 95%).

A solution of the intermediate 3 (4.3 g, 8.5 mmol), diphenylamine (3.2 g, 18.7 mmol, produced by Nacalai Tesque, Inc.), tri-tert-butylphosphine tetrafluoroborate (0.40 g, 0.22 mmol, produced by Sigma-Aldrich Corporation), sodium tert-butoxide (2.8 g, 29.2 mmol, produced by Tokyo Chemical Industry Co., Ltd.) and tris(dibenzylideneacetone) (chloroform) palladium(0) (0.056 g, 0.054 mmol) in toluene (200 mL, produced by Kanto Chemical Co., Inc.) was heated to 80° C. in an argon atmosphere for 1 hour. Subsequently, after cooling at room temperature, toluene (250 mL) and water (200 mL) were added to the reaction solution, and the mixture was separated. The organic layer was dried over anhydrous magnesium sulfate, from which the solvent was distilled off with an evaporator, and the product was recrystallized from a mixed solvent of ethyl acetate and hexane to provide an intermediate 4 in the form of blackish green solid (4.24 g, yield: 840).

A solution of intermediate 4 (3.0 g, 5.1 mmol) in anisole (16 mL, produced by Sigma-Aldrich Corporation) was added dropwise to a suspension liquid of anhydrous aluminum(III) chloride (5.0 g, 37.8 mmol, produced by Wako Pure Chemical Industries, Ltd.) in anisole (4.7 mL, produced by Sigma-Aldrich Corporation) under cooling with ice, and then the mixture was heated to 60° C. for 21 hours. Subsequently, after cooling at room temperature, dichloromethane (100 mL) and water (50 mL) were added to the reaction solution, and the mixture was separated. The organic layer was washed with a 5% sodium hydrogen carbonate aqueous solution (50 mL) and a saturated sodium chloride aqueous solution (50 mL). The organic layer was dried over anhydrous magnesium sulfate, from which the solvent was distilled off with an evaporator. The residue was purified by silica gel column chromatography (dichloromethane/hexane: 40%/60%) to provide an intermediate 5 in the form of blackish green solid (2.23 g, yield: 76%).

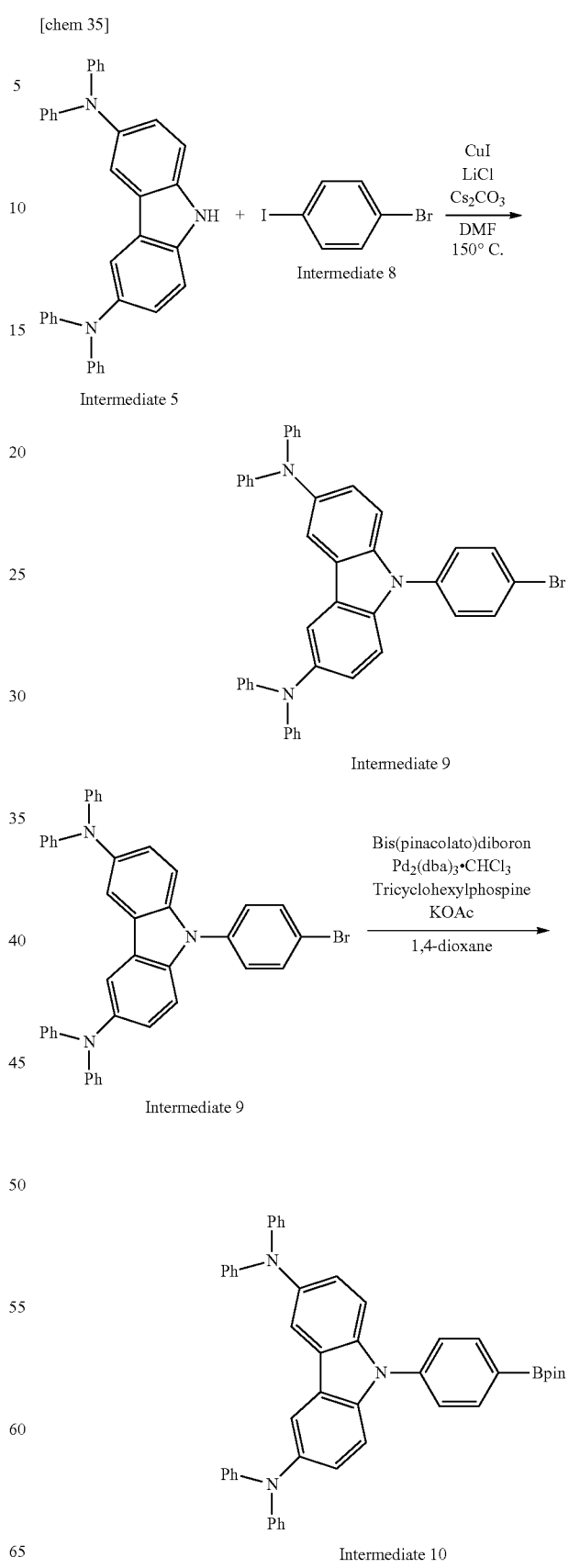

Tetrahydrofuran (15 mL) was added to magnesium (4.1 g, 172.8 mmol, produced by Wako Pure Chemical Industries, Ltd.), to which dibromoethane (0.29 g, 0.0015 mmol, produced by Wako Pure Chemical Industries, Ltd.) was added under stirring. Bromobenzene (26.2 g, 166.8 mmol, produced by Nacalai Tesque, Inc.) was added dropwise thereto at room temperature, and the mixture was refluxed under an argon atmosphere for 3 hours. After cooling at room temperature, the solution was added dropwise to a solution of cyanuric chloride (intermediate 6) (8.2 g, 44.3 mmol, produced by Tokyo Chemical Industry Co., Ltd.) in tetrahydrofuran (50 mL) under cooling with ice, and then the mixture was heated to 35° C. in an argon atmosphere for 18 hours. After cooling at room temperature, dichloromethane (100 mL) and water (40 mL) were added to the reaction solution, and the mixture was separated. The organic layer was dried over anhydrous sodium sulfate, from which the solvent was distilled off with an evaporator. A part of the residue (1.35 g) was purified by silica gel column chromatography (dichloromethane/hexane: 20%/80%) to provide an intermediate 7 in the form of white solid (1.128 g).

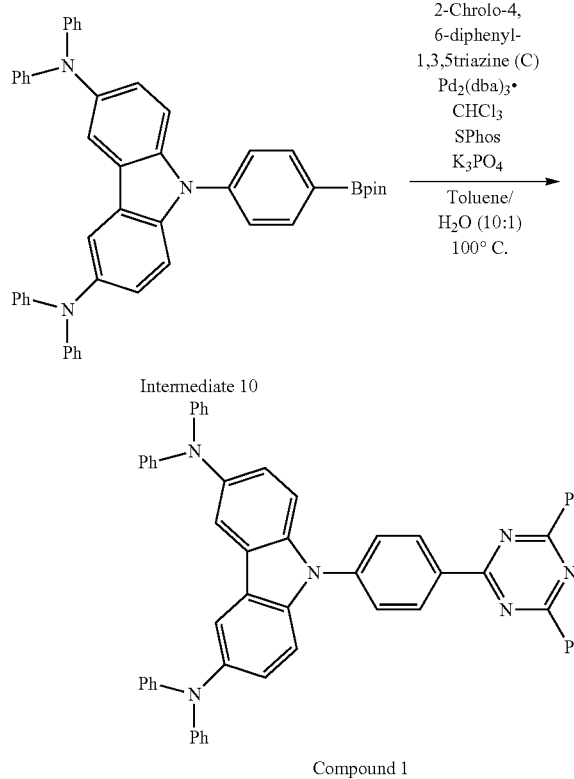

Intermediate 10

Compound 1

A suspension liquid of the intermediate 5 (2.01 g, 4.0 mmol), p-bromoiodobenzene (intermediate 8) (1.37 g, 4.8 mmol, produced by Wako Pure Chemical Industries, Ltd.), lithium chloride (0.15 g, 7.2 mmol, produced by Wako Pure Chemical Industries, Ltd.) cesium carbonate (1.68 g, 5.1 mmol, produced by Tokyo Chemical Industry Co., Ltd.) and copper iodide (0.11 g, 0.58 mmol, produced by Kanto Chemical Co., Ltd.) in dimethylformamide (35 mL, produced by Wako Pure Chemical Industries, Ltd.) was heated to 150° C. under an argon atmosphere for 38 hours. Subsequently, after cooling at room temperature, a saturated ammonium chloride aqueous solution (30 mL) and dichloromethane (100 mL) were added to the reaction solution, and the mixture was separated. The organic layer was dried over magnesium sulfate, from which the solvent was distilled off with an evaporator. The residue was purified by silica gel column chromatography (dichloromethane/hexane: 20%/80%) to provide an intermediate 9 in the form of white crystals (0.1.9 g, yield: 71%).

A solution of tricyclohexylphosphine (0.053 g, 0.19 mmol, produced by Strem Chemicals, Inc.) and tris(dibenzylideneacetone) (chloroform) palladium(0) (0.043 g, 0.041 mmol) in 1.4-dioxane (15 mL, produced by Wako Pure Chemical Industries, Ltd.) was stirred at room temperature for 30 minutes, to which the intermediate 9 (1.64 g, 2.5 mmol), bis(pinacolato)diboron (0.70 g, 2.8 mmol, produced by Wako Pure Chemical Industries, Ltd.) and potassium acetate (0.53 g, 11.0 mmol, produced by Wako Pure Chemical Industries, Ltd.) were added, and the mixture was heated to 80° C. under an argon atmosphere for 18 hours. Subsequently, after cooling to room temperature, water (5 mL) and toluene (20 mL) were added to the reaction solution, and the mixture was separated. The organic layer was washed with a saturated sodium chloride aqueous solution (10 mL), and then dried over anhydrous magnesium sulfate. The solvent was distilled off with an evaporator to provide a mixture containing an intermediate 10 (1.6 g).

The mixture containing the intermediate 10 (1.6 g), 2-chloro-4,6-diphenyl-1,3,5-triazine (0.0787 g, 2.9 mmol), potassium phosphate (1.0 g, 4.7 mmol), tris(dibenzylideneacetone) (chloroform) palladium(0) (0.014 g, 0.014 mmol) and 2-dicyclohexylphosphino-2',6'-dimethoxybiphenyl (0.027 g, 0.067 mmol) were dissolved in a mixed solvent of toluene (5 mL) and water (0.5 mL), and the solution was heated to 100° C. for 2 hours. After cooling to room temperature, the reaction solution was diluted with dichloromethane, and passed through a silica gel column. The solvent was distilled off from the solution with an evaporator, and the residue was purified by silica gel column chromatography (dichloromethane/hexane: 20%/80%) and recrystallized twice from a mixed solvent of dichloromethane and hexane to provide the compound 1 in the form of yellow crystals (0.98 g). The crystals were further purified by sublimation to provide the compound 1 in the form of yellow solid (0.70 g).

melting point: 265° C.

$^1$H-NMR (300 MHz acetone D6): δ 9.143 (d, J=8.7 Hz, 2H), 8.931 (dd, J$_1$=8.0 Hz, J$_2$=1.4 Hz, 4H), 8.003 (d, J=8.7, 2H), 7.944 (d, J=1.8 Hz, 2H), 7.733-7.650 (m, 6H), 7.628 (s, 2H), 7.311 (d, J=2.4 Hz, 2H), 7.278-7.212 (m, 10H), 7.072-6.930 (m, 10H)

Synthesis Example 2

Synthesis of Compound 2

[chem 36]

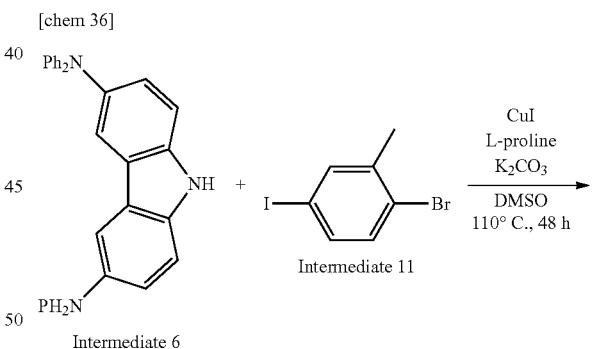

Intermediate 6

Intermediate 11

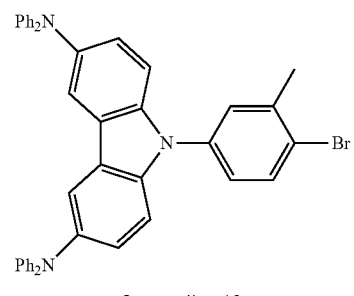

Intermediate 12

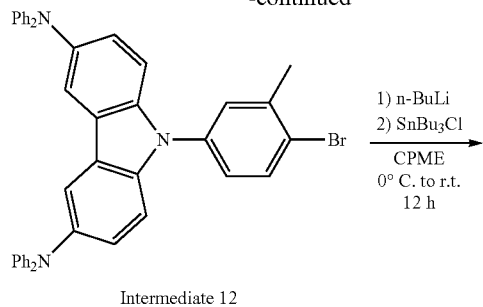

Intermediate 12

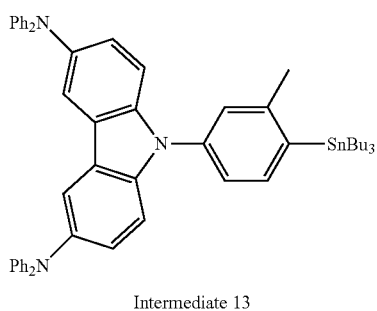

Intermediate 13

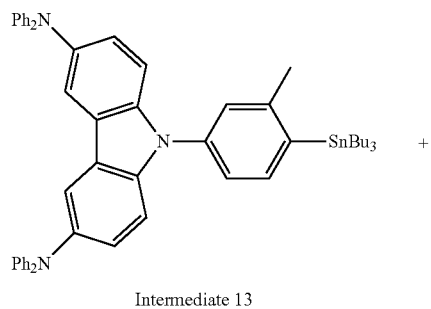

Intermediate 13

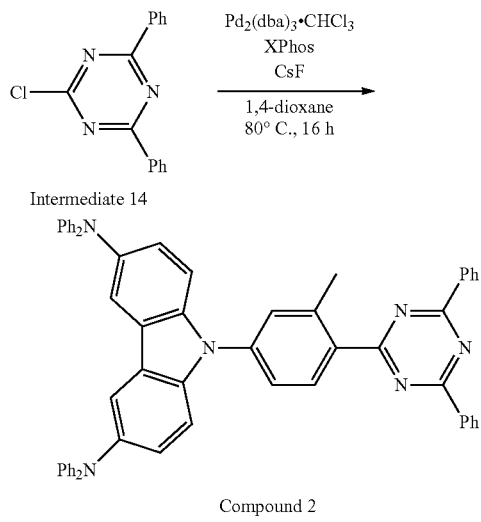

Compound 2

Under an argon atmosphere, a suspension liquid of the intermediate 6 (1.20 g, 2.40 mmol), 1-bromo-4-iodo-2-methylbenzene (intermediate 11) (852 mg, 2.88 mmol), L-proline (110 mg, 0.96 mmol, produced by Wako Pure Chemical Industries, Ltd.), potassium carbonate (1.68 g, 4.80 mmol, produced by Wako Pure Chemical Industries, Ltd.) and copper iodide (91.4 mg, 0.48 mmol, produced by Wako Pure Chemical Industries, Ltd.) in dimethylformamide (2.4 mL, produced by Wako Pure Chemical Industries, Ltd.) was heated to 110° C. for 48 hours. Subsequently, after cooling to room temperature, a saturated ammonium chloride aqueous solution (30 mL) and dichloromethane (100 mL) were added to the reaction solution, and the mixture was, separated. The organic layer was dried over magnesium sulfate, from which the solvent was distilled off with an evaporator. The residue was purified by silica gel column chromatography (dichloromethane/hexane: 20%/80%) to provide an intermediate 12 in the form of pale yellow crystals (1.43 g, yield: 89%).

$^1$H-NMR (600 MHz, CDCl$_3$): δ 7.75-7.73 (m, 3H), 7.45 (d, J=2.4 Hz, 1H), 7.31-7.27 (m, 3H), 7.23-7.18 (m, 10H), 7.06 (d, J=7.8 Hz, 8H), 6.93 (t, J=7.5 Hz, 4H), 2.50 (s, 3H)

Under an argon atmosphere, the intermediate 12 (1.20 g, 1.79 mmol) was dissolved in cyclopentyl methyl ether (17 mL, produced by Wako Pure Chemical Industries, Ltd.), and the solution was cooled to 0° C. A hexane solution of n-butyllithium (1.6 M, 1.23 mL, 1.97 mmol, produced by Wako Pure Chemical Industries, Ltd.) was added dropwise to the solution, and the mixture was stirred at 0° C. for 1.5 hours. Tributyltin chloride (699 mg, 2.15 mmol, produced by Sigma-Aldrich Corporation) was added dropwise to the solution, and the mixture was stirred at room temperature for 10 hours. Water (30 mL) and toluene (30 mL) were added to the reaction solution, and the mixture was separated. The organic layer was washed with a saturated sodium chloride aqueous solution (20 mL), and then dried over anhydrous magnesium sulfate. The solvent was distilled off with an evaporator to provide a mixture containing an intermediate 13 (1.4 g). The mixture was used in the subsequent reaction without purification.

Under an argon atmosphere, the mixture containing the intermediate 13 (1.4 g), the intermediate 14 (574 mg, 2.15 mmol), cesium fluoride (599 mg, 3.94 mmol, produced by Wako Pure Chemical Industries, Ltd.), tris(dibenzylideneacetone) (chloroform) palladium(0) (27.9 mg, 0.027 mmol) and 2-dichlorohexylphosphino-2',4',6'-triisopropylbiphenyl (52.4 mg, 0.11 mmol, produced by Sigma-Aldrich Corporation) were dissolved in 1,4-dioxane (1.8 mL, produced by Wako Pure Chemical Industries, Ltd.), and the solution was heated to 80° C. for 16 hours. After cooling to room temperature, the reaction solution was diluted with dichloromethane, and passed through a silica gel column. The solvent was distilled off from the solution with an evaporator, and the residue was purified by silica gel column chromatography (dichloromethane/hexane: 20%/80%) and recrystallized from a mixed solvent of dichloromethane and hexane to provide the compound 2 in the form of yellow crystals (0.90 g, yield: 61%).

$^1$H-NMR (600 MHz, CDCl$_3$): δ 8.78 (d, J=6.6 Hz, 4H), 8.60 (d, J=8.4 Hz, 1H), 7.79 (d, J=6.6 Hz, 2H), 7.67-7.56 (m, 8H), 7.27-7.24 (m, 4H), 7.24-7.18 (m, 8H), 7.09 (d, J=8.4 Hz, 8H), 6.95 (t, J=7.5 Hz, 4H), 2.98 (s, 3H)

Synthesis Example 3

Synthesis of Compound 3

[chem 37]

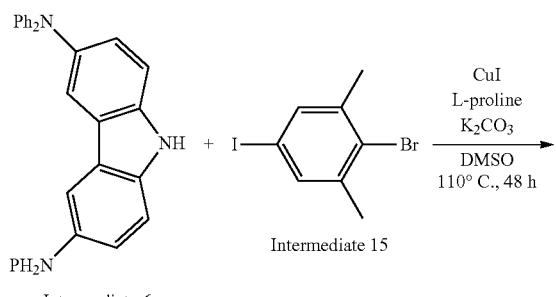

Intermediate 6 + Intermediate 15 → (CuI, L-proline, K$_2$CO$_3$, DMSO, 110° C., 48 h)

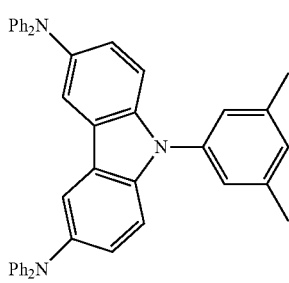

Intermediate 16

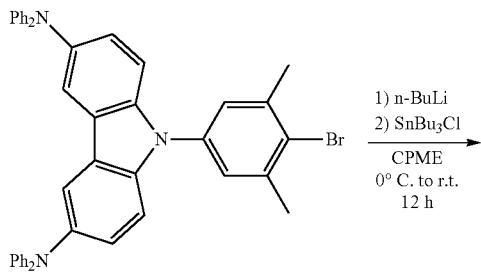

Intermediate 16 → (1) n-BuLi; 2) SnBu$_3$Cl; CPME, 0° C. to r.t., 12 h)

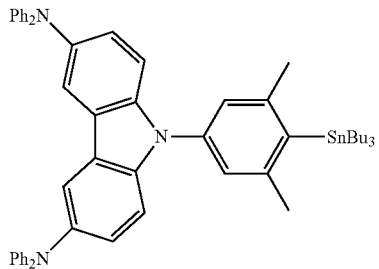

Intermediate 17

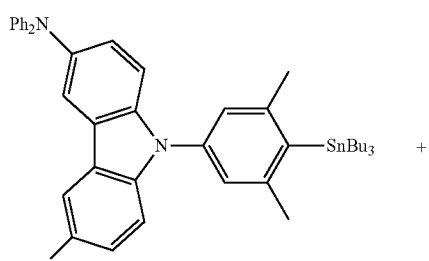

Intermediate 17 +

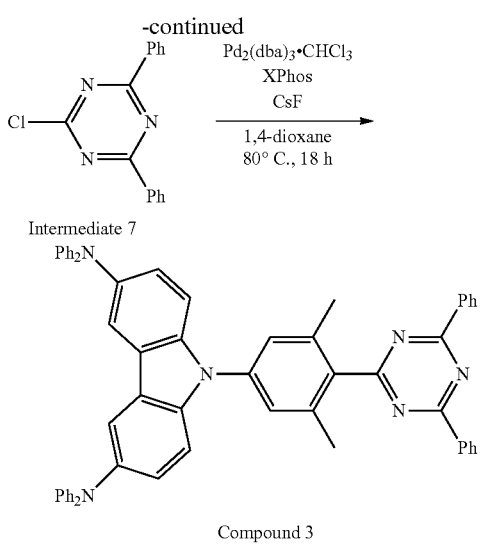

Intermediate 7

→ (Pd$_2$(dba)$_3$·CHCl$_3$, XPhos, CsF, 1,4-dioxane, 80° C., 18 h)

Compound 3

Under an argon atmosphere, a suspension liquid of the intermediate 6 (1.20 g, 2.40 mmol), 2-bromo-5-iodo-1,3-dimethylbenzene (intermediate 15) (893 mg, 2.88 mmol), L-proline (110 mg, 0.96 mmol, produced by Wako Pure Chemical Industries, Ltd.), potassium carbonate (1.68 g, 4.80 mmol, produced by Wako Pure Chemical Industries, Ltd.) and copper iodide (91.4 mg, 0.48 mmol, produced by Wako Pure Chemical Industries, Ltd.) in dimethylformamide (2.4 mL, produced by Wako Pure Chemical Industries, Ltd.) was heated to 110° C. for 48 hours. Subsequently, after cooling to room temperature, a saturated ammonium chloride aqueous solution (30 mL) and dichloromethane (100 mL) were added to the reaction solution, and the mixture was separated. The organic layer was dried over magnesium sulfate, from which the solvent was distilled off with an evaporator. The residue was purified by silica gel column chromatography (dichloromethane/hexane: 20%/80%) to provide an intermediate 16 in the form of pale yellow crystals (1.49 g, yield: 91%).

$^1$H-NMR (600 MHz, CDCl$_3$): δ 7.75 (s, 2H), 7.31-7.27 (m, 4H), 7.23-7.16 (m, 10H), 7.06 (d, J=7.8 Hz, 8H), 6.93 (t, J=7.2 Hz, 4H), 2.52 (s, 6H)

Under an argon atmosphere, the intermediate 16 (1.22 g, 1.79 mmol) was dissolved in cyclopentyl methyl ether (17 mL, produced by Wako Pure Chemical Industries, Ltd.), and the solution was cooled to 0° C. A hexane solution of n-butyllithium (1.6 M, 1.23 mL, 1.97 mmol, produced by Wako Pure Chemical Industries, Ltd.) was added dropwise to the solution, and the mixture was stirred at 0° C. for 1.5 hours. Tributyltin chloride (699 mg, 2.15 mmol, produced by Sigma-Aldrich Corporation) was added dropwise to the solution, and the mixture was stirred at room temperature for 10 hours. Water (30 mL) and toluene (30 mL) were added to the reaction solution, and the mixture was separated. The organic layer was washed with a saturated sodium chloride aqueous solution (20 mL), and then dried over anhydrous magnesium sulfate. The solvent was distilled off with an evaporator to provide a mixture containing an intermediate 17 (1.4 g). The mixture was used in the subsequent reaction without purification.

Under an argon atmosphere, the mixture containing the intermediate 17 (1.4 g), the intermediate 7 (574 mg, 2.15 mmol), cesium fluoride (599 mg, 3.94 mmol, produced by Wako Pure Chemical Industries, Ltd.), tris(dibenzylideneacetone) (chloroform) palladium(0) (27.9 mg, 0.027 mmol)

and 2-dichlorohexylphosphino-2',4',6'-triisopropylbiphenyl (52.4 mg, 0.11 mmol, produced by Sigma-Aldrich Corporation) were dissolved in 1,4-dioxane (1.8 mL, produced by Wako Pure Chemical Industries, Ltd.), and the solution was heated to 80° C. for 16 hours. After cooling to room temperature, the reaction solution was diluted with dichloromethane, and passed through a silica gel column. The solvent was distilled off from the solution with an evaporator, and the residue was purified by silica gel column chromatography (dichloromethane/hexane: 20%/80%) and recrystallized from a mixed solvent of dichloromethane and hexane to provide the compound 3 in the form of yellow crystals (0.87 g, yield: 580).

$^1$H-NMR (600 MHz, CDCl$_3$): δ 8.75 (d, J=7.8 Hz, 4H), 7.79 (d, J=1.8 Hz, 2H), 7.64 (t, J=7.2 Hz, 2H), 7.59 (t, J=7.5 Hz, 4H), 7.48 (d, J=8.4 Hz, 2H), 7.43 (s, 2H), 7.28-7.24 (m, 2H), 7.22 (t, J=8.1 Hz, 8H), 7.09 (d, J=8.4 Hz, 8H), 6.94 (t, J=7.5 Hz, 4H), 2.44 (s, 6H)

Synthesis Example 4

Synthesis of Compound 4

[chem 38]

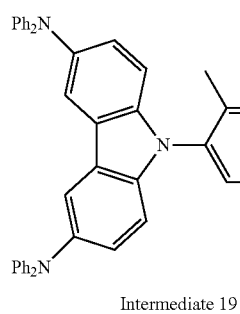

Intermediate 6

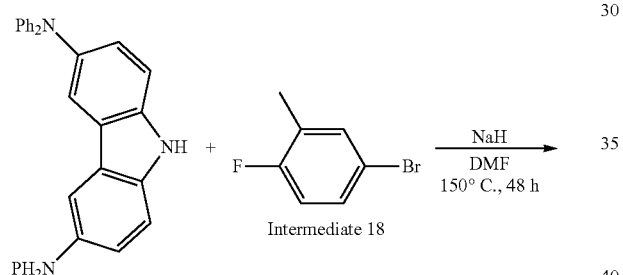

Intermediate 19

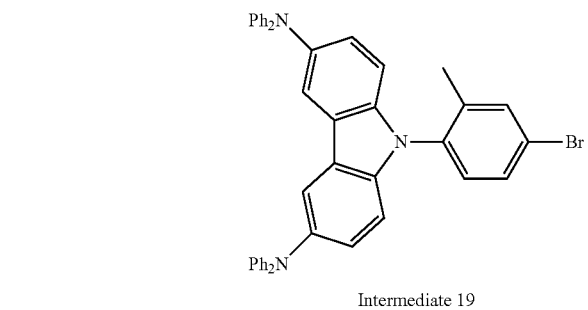

Intermediate 19

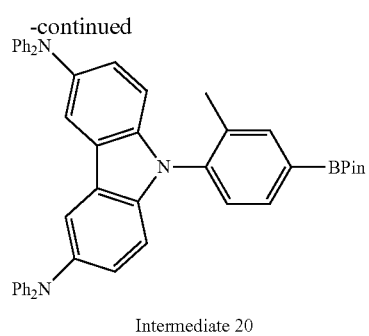

Intermediate 20

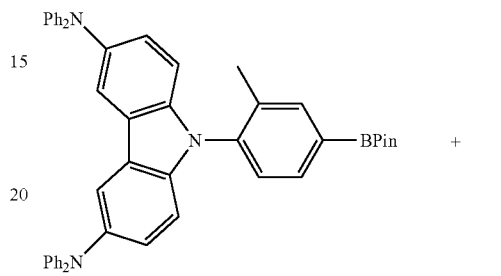

Intermediate 20

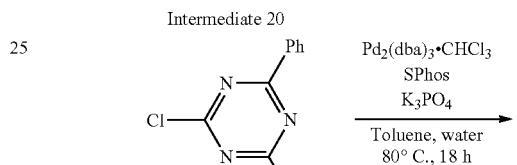

Intermediate 7

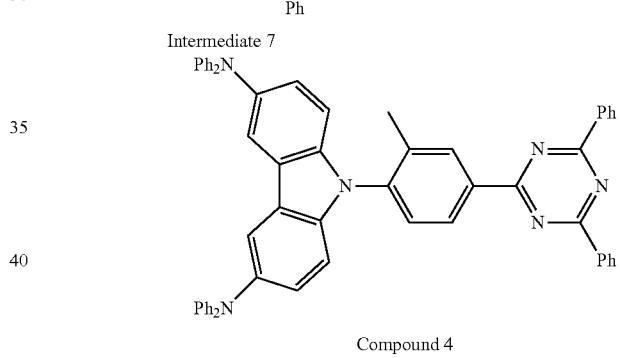

Compound 4

Under an argon atmosphere at 0° C., the intermediate 6 (1.20 g, 2.40 mmol) was added to a suspension liquid of NaH (containing 40% of a mineral oil, 63.3 mg, 2.64 mmol, produced by Wako Pure Chemical Industries, Ltd.) in dimethylformamide (2.4 mL, produced by Wako Pure Chemical Industries, Ltd.), and the mixture was stirred for 30 minutes. 4-Bromo-1-fluoro-2-methylbenzene (intermediate 18) (2.25 g, 12.0 mmol) was added to the solution, and the solution was heated to 150° C. for 48 hours. Subsequently, after cooling to room temperature, a saturated ammonium chloride aqueous solution (30 mL) and dichloromethane (100 mL) were added to the reaction solution, and the mixture was separated. The organic layer was dried over magnesium sulfate, from which the solvent was distilled off with an evaporator. The residue was purified by silica gel column chromatography (dichloromethane/hexane: 20%/80%) to provide an intermediate 19 in the form of pale yellow crystals (1.49 g, yield: 93%).

$^1$H-NMR (600 MHz, CDCl$_3$): δ 7.77 (s, 2H), 7.66-7.61 (m, 1H), 7.54-7.49 (m 1H), 7.28-7.14 (m, 13H), 7.07 (d, J=7.8 Hz, 8H), 6.93 (t, J=7.5 Hz, 4H), 2.07 (s, 3H)

Under an argon atmosphere, a solution of tricyclohexylphosphine (30.8 mg, 0.11 mmol, produced by Strem Chemicals, Inc.) and tris(dibenzylideneacetone) (chloroform) palladium(0) (27.9 mg, 0.027 mmol) in 1.4-dioxane (10 mL, produced by Wako Pure Chemical Industries, Ltd.) was stirred at room temperature for 30 minutes, to which the intermediate 19 (1.20 g, 1.79 mmol), bis(pinacolato)diboron (546 mg, 2.15 mmol, produced by Tokyo Chemical Industry Co., Ltd.) and potassium acetate (351 mg, 3.58 mmol, produced by Wako Pure Chemical Industries, Ltd.) were added, and the mixture was heated to 80° C. for 18 hours. Subsequently, after cooling to room temperature, water (5 mL) and toluene (20 mL) were added to the reaction solution, and the mixture was separated. The organic layer was washed twice with a saturated sodium chloride aqueous solution (10 mL), and then dried over anhydrous sodium sulfate. The solvent was distilled off with an evaporator to provide a mixture containing an intermediate 20 (1.5 g). The mixture was used in the subsequent reaction without purification.

Under an argon atmosphere, the mixture containing the intermediate 20 (1.5 g), the intermediate 7 (574 mg, 2.15 mmol), potassium phosphate (758 mg, 3.58 mmol, produced by Wako Pure Chemical Industries, Ltd.), tris(dibenzylideneacetone) (chloroform) palladium(0) (27.9 mg, 0.027 mmol) and 2-dichlorohexylphosphino-2',6'-dimethoxybiphenyl (45.2 mg, 0.11 mmol, produced by Wako Pure Chemical Industries, Ltd.) were dissolved in a mixed solvent of toluene (1.0 mL) and water (0.1 mL), and the solution was heated to 100° C. for 16 hours. After cooling to room temperature, the reaction solution was diluted with dichloromethane, and passed through a silica gel column. The solvent was distilled off from the solution with an evaporator, and the residue was purified by silica gel column chromatography (dichloromethane/hexane: 20%/80%) and recrystallized from a mixed solvent of dichloromethane and hexane to provide the compound 4 in the form of yellow crystals (0.84 g, yield: 57%).

$^1$H-NMR (600 MHz, CDCl$_3$): δ 8.88 (s, 1H), 8.85-8.76 (m, 5H), 7.81 (s, 2H), 7.67-7.58 (m, 8H), 7.24-7.6.94 (m, 23H), 2.29 (s, 3H)

Synthesis Example 5

Synthesis of Compound 5

[chem 39]

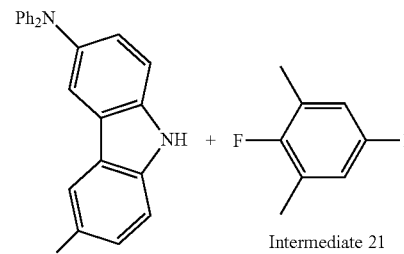

Intermediate 6

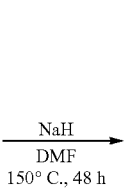

Intermediate 21

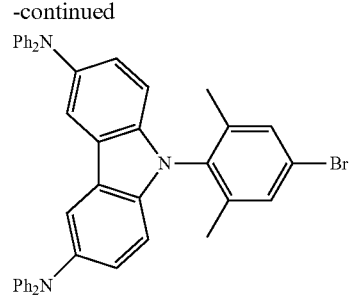

Intermediate 22

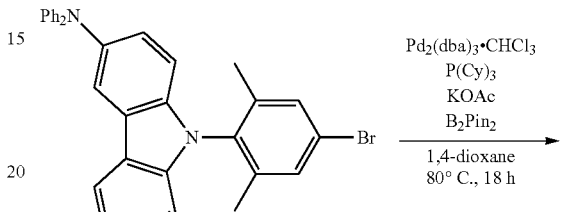

Intermediate 22

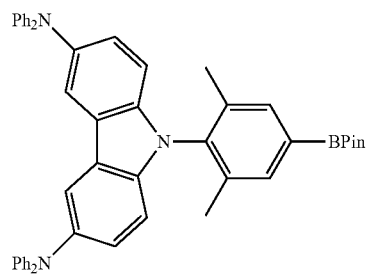

Intermediate 23

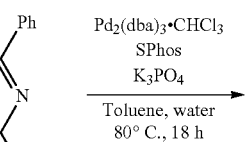

Intermediate 23

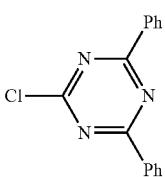

Intermediate 7

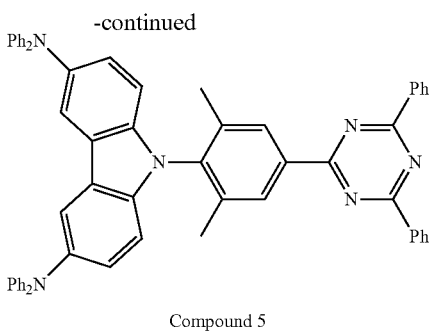

Compound 5

Under an argon atmosphere at 0° C., the intermediate 6 (1.20 g, 2.40 mmol) was added to a suspension liquid of NaH (containing 40% of a mineral oil, 63.3 mg, 2.64 mmol, produced by. Wako Pure Chemical Industries, Ltd.) in dimethylformamide (2.4 mL, produced by Wako Pure Chemical Industries, Ltd.), and the mixture was stirred for 30 minutes. 5-Bromo-2-fluoro-1,3-dimethylbenzene (intermediate 21) (4.85 g, 24.0 mmol) was added to the solution, and the solution was heated to 150° C. for 48 hours. Subsequently, after cooling to room temperature, a saturated ammonium chloride aqueous solution (30 mL) and dichloromethane (100 mL) were added to the reaction solution, and the mixture was separated. The organic layer was dried over magnesium sulfate, from which the solvent was distilled off with an evaporator. The residue was purified by silica gel column chromatography (dichloromethane/hexane: 20%/80%) to provide an intermediate 22 in the form of pale yellow crystals (1.44 g, yield: 88%).

$^1$H-NMR (600 MHz, CDCl$_3$): δ 7.78 (s, 2H), 7.44 (s, 2H), 7.24-7.22 (m 8H), 7.07 (d, J=7.8 Hz, 8H), 6.93 (t, J=7.2 Hz, 4H), 6.82 (d, J=9.0 Hz, 2H), 1.93 (s, 6H)

Under an argon atmosphere, a solution of tricyclohexylphosphine (30.8 mg, 0.11 mmol, produced by Strem Chemicals, Inc.) and tris(dibenzylideneacetone) (chloroform) palladium(0) (27.9 mg, 0.027 mmol) in 1.4-dioxane (10 mL, produced by Wako Pure Chemical Industries, Ltd.) was stirred at room temperature for 30 minutes, to which the intermediate 22 (1.20 g, 1.79 mmol), bis(pinacolato)diboron (546 mg, 2.15 mmol, produced by Tokyo Chemical Industry Co., Ltd.) and potassium acetate (351 mg, 3.58 mmol, produced by Wako Pure Chemical Industries, Ltd.) were added, and the mixture was heated to 80° C. for 18 hours. Subsequently, after cooling to room temperature, water (5 mL) and toluene (20 mL) were added to the reaction solution, and the mixture was separated. The organic layer was washed twice with a saturated sodium chloride aqueous solution (10 mL), and then dried over anhydrous sodium sulfate. The solvent was distilled off with an evaporator to provide a mixture containing an intermediate 23 (1.5 g). The mixture was used in the subsequent reaction without purification.

Under an argon atmosphere, the mixture containing the intermediate 23 (1.5 g), the intermediate 7 (574 mg, 2.15 mmol), potassium phosphate (758 mg, 3.58 mmol, produced by Wako Pure Chemical Industries, Ltd.), tris(dibenzylideneacetone) (chloroform) palladium(0) (27.9 mg, 0.027 mmol) and 2-dichlorohexylphosphino-2',6'-dimethoxybiphenyl (45.2 mg, 0.11 mmol, produced by Wako Pure Chemical Industries, Ltd.) were dissolved in a mixed solvent of toluene (1.0 mL) and water (0.1 mL), and the solution was heated to 100° C. for 16 hours. After cooling to room temperature, the reaction solution was diluted with dichloromethane, and passed through a silica gel column. The solvent was distilled off from the solution with an evaporator, and the residue was purified by silica gel column chromatography (dichloromethane/hexane: 20%/80%) and recrystallized from a mixed solvent of dichloromethane and hexane to provide the compound 5 in the form of yellow crystals (0.88 g, yield: 60%).

$^1$H-NMR (600 MHz, CDCl$_3$): δ 8.82 (d, J=6.6 Hz, 4H), 8.66 (s, 2H), 7.82 (s, 2H), 7.67-7.58 (m, 8H), 7.22 (t, J=8.1 Hz, 8H), 7.10 (d, J=7.8 Hz, 8H), 6.97-6.85 (m, 6H), 2.14 (s, 6H)

Example 1

Production and Evaluation of Organic Photoluminescent Device (Solution)

Figure 2:
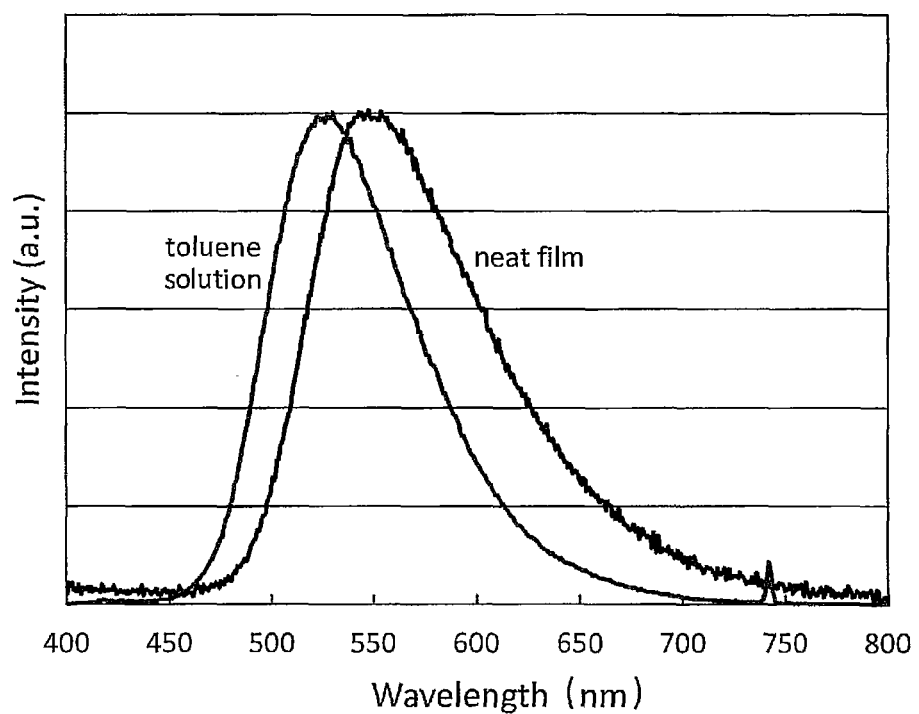
FIG. 2 is the light emission spectra of the solution of the compound 1 in Example 1 and the organic photoluminescent device of the compound 1 in Example 2.
Figure 3:
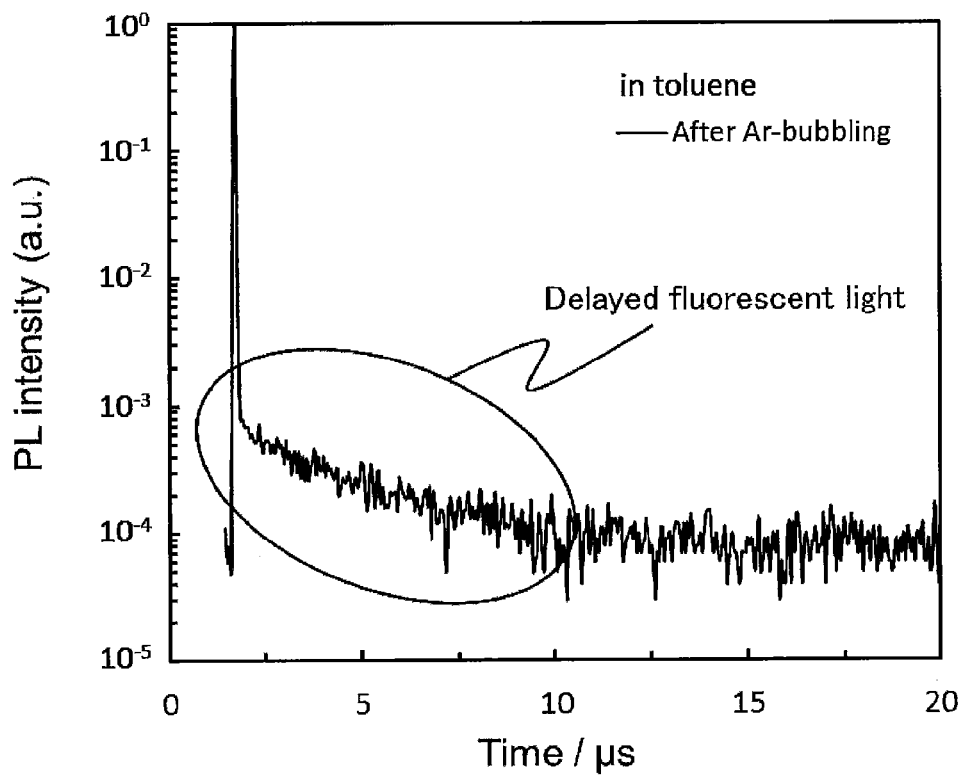
FIG. 3 is the transient decay curve of the solution of the compound 1 in Example 1.

In a glove box under an Ar atmosphere, a toluene solution of the compound 1 (concentration: 10$^{-5}$ mol/L) was prepared and measured for the light emission spectrum with excitation light having a wavelength of 370 nm. The result is shown in FIG. 2. The solution was measured for the transient decay curve of a light emission wavelength of 550 nm at 300 K under Ar bubbling. The result is shown in FIG. 3 (τ1=14.3 ns, τ2=3.3 μs). The transient decay curve shows the measurement result of the light emission lifetime obtained by measuring the process where the light emission intensity is deactivated on irradiating the compound with excitation light. In ordinary one-component light emission (fluorescent light or phosphorescent light), the light emission intensity is decays monoexponentially. This means that the light emission intensity decays linearly on a graph with the semilogarithm as the ordinate. In a transient decay curve of the compound 1, while a linear component (fluorescent light) was observed in the initial stage of observation, a component that deviated from the linearity appeared thereafter. The later component is light emission of the delayed component, and the signal thereof added to the initial component appears as a long tail curve on the longer time side. Thus, the measurement of the light emission lifetime revealed that the compound 1 was a light emitting material that contained a delayed component in addition to a fluorescent component. The photoluminescence quantum efficiency was 26% under O$_2$ bubbling, 48% without bubbling, and 65% under N$_2$ bubbling.

Figure 4:
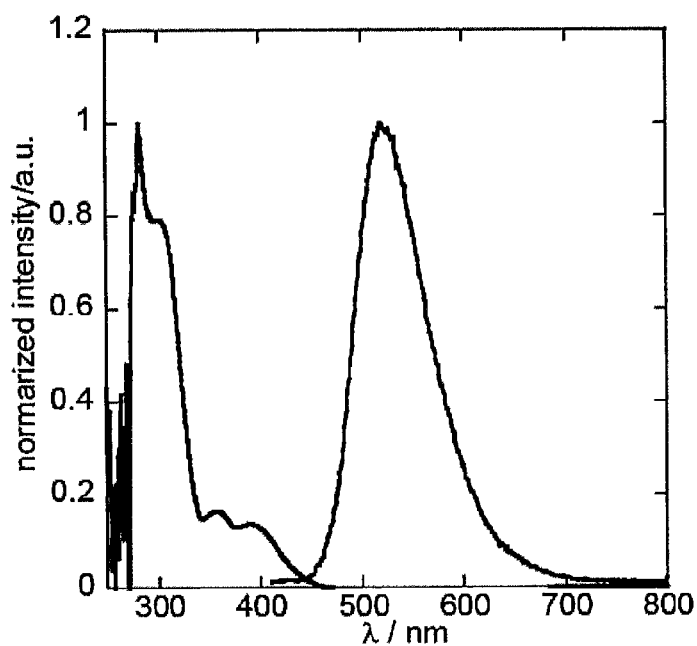
FIG. 4 is the absorption and emission spectra of the solution of the compound 2 in Example 1.
Figure 5:
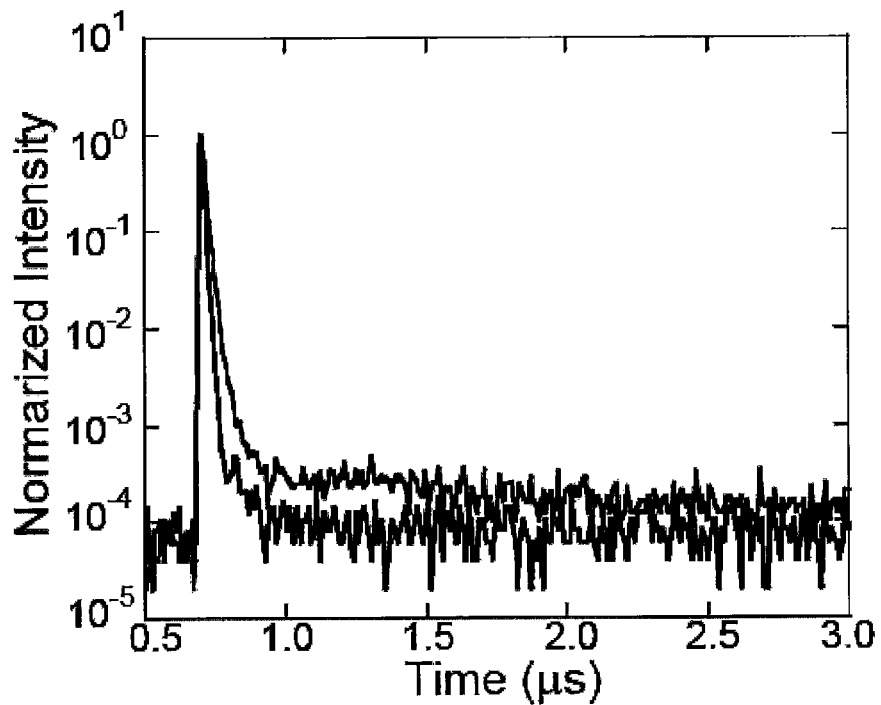
FIG. 5 is the transient decay curves of the solution of the compound 2 in Example 1.

A toluene solution of the compound 2 (concentration: 10$^{-5}$ mol/L) was prepared and measured for the absorption and emission spectra. The results are shown in FIG. 4. The solution was measured for the transient decay curves at the peak light emission wavelength under conditions with Ar bubbling and without Ar bubbling. The results are shown in FIG. 5. Delayed fluorescent light was observed in the measurement under the condition with Ar bubbling. The photoluminescence quantum efficiency was 47% without Ar bubbling and 84% under Ar bubbling.

Figure 6:
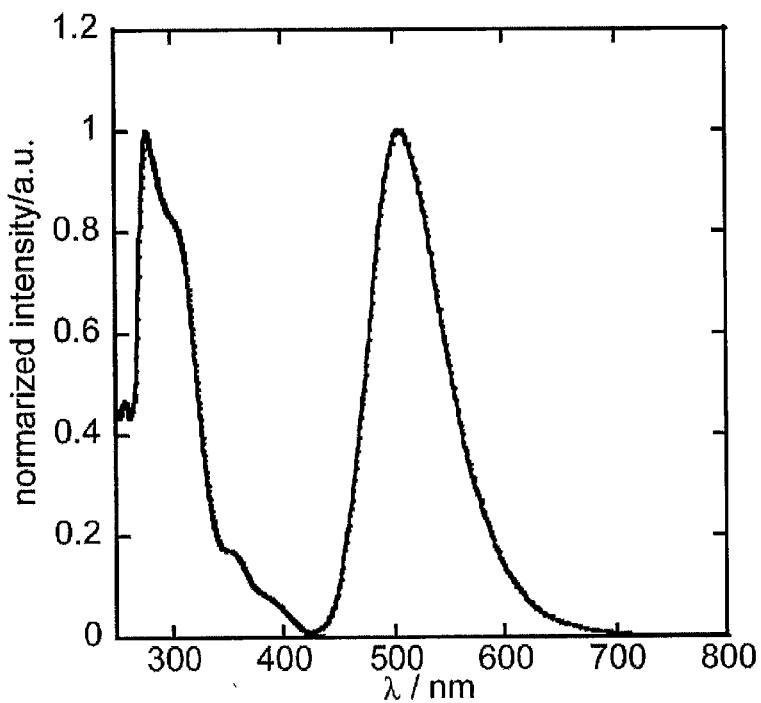
FIG. 6 is the absorption and emission spectra of the solution of the compound 3 in Example 1.
Figure 7:
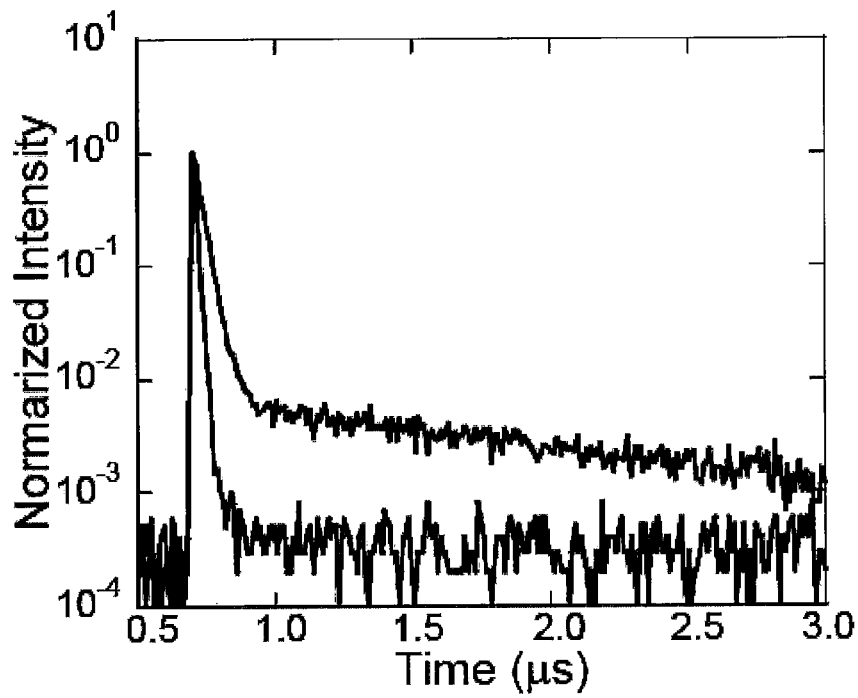
FIG. 7 is the transient decay curve of the solution of the compound 3 in Example 1.

A toluene solution of the compound 3 (concentration: 10$^{-5}$ mol/L) was prepared and measured for the absorption and emission spectra. The results are shown in FIG. 6. The solution was measured for the transient decay curves at the peak light emission wavelength under conditions with Ar bubbling and without Ar bubbling. The results are shown in FIG. 7. Delayed fluorescent light was observed in the measurement under the condition with Ar bubbling. The photoluminescence quantum efficiency was 11% without Ar bubbling and 42% under Ar bubbling.

Figure 8:
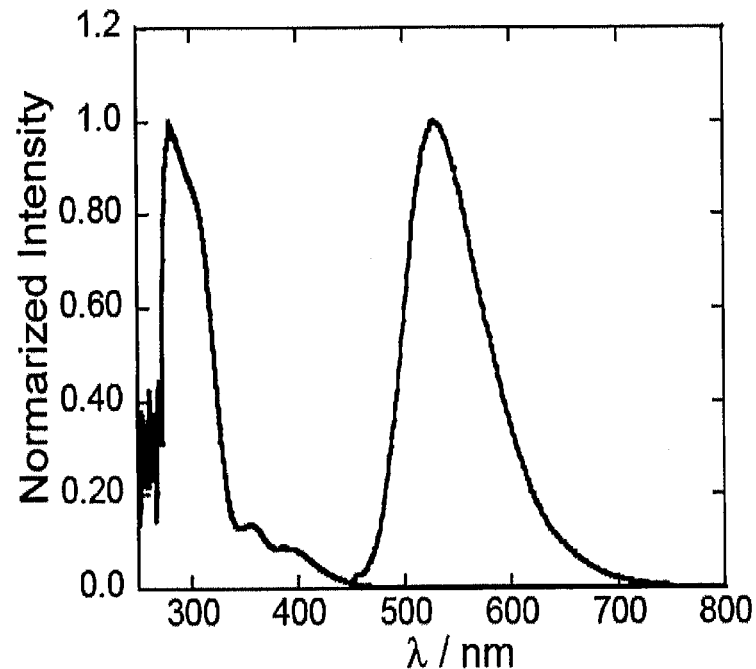
FIG. 8 is the absorption and emission spectra of the solution of the compound 4 in Example 1.
Figure 9:
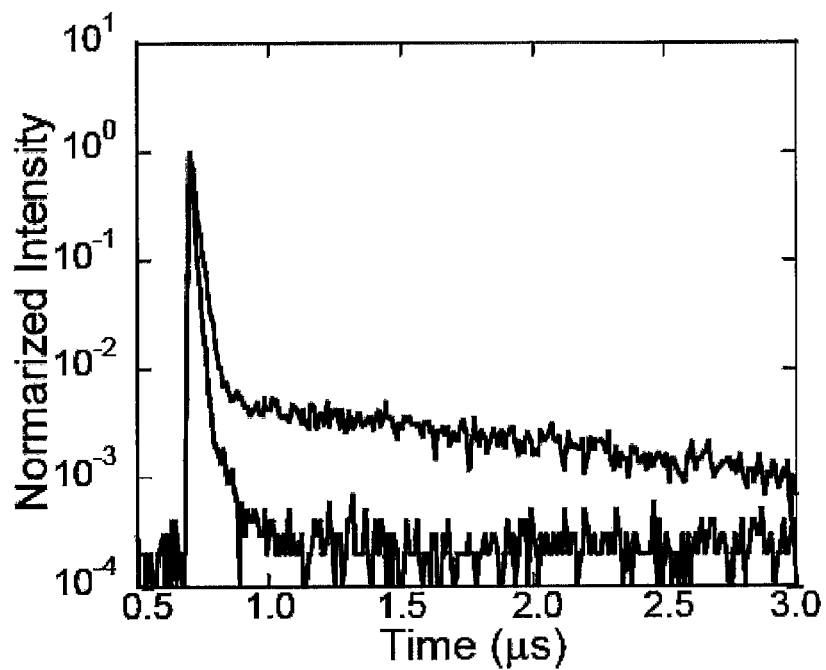
FIG. 9 is the transient decay curve of the solution of the compound 4 in Example 1.

A toluene solution of the compound 4 (concentration: 10$^{-5}$ mol/L) was prepared and measured for the absorption and emission spectra. The results are shown in FIG. 8. The solution was measured for the transient decay curves at the peak light emission wavelength under conditions with Ar bubbling and without Ar bubbling. The results are shown in FIG. 9. Delayed fluorescent light was observed in the measurement under the condition with Ar bubbling. The photoluminescence quantum efficiency was 31% without Ar bubbling and 60% under Ar bubbling.

Figure 10:
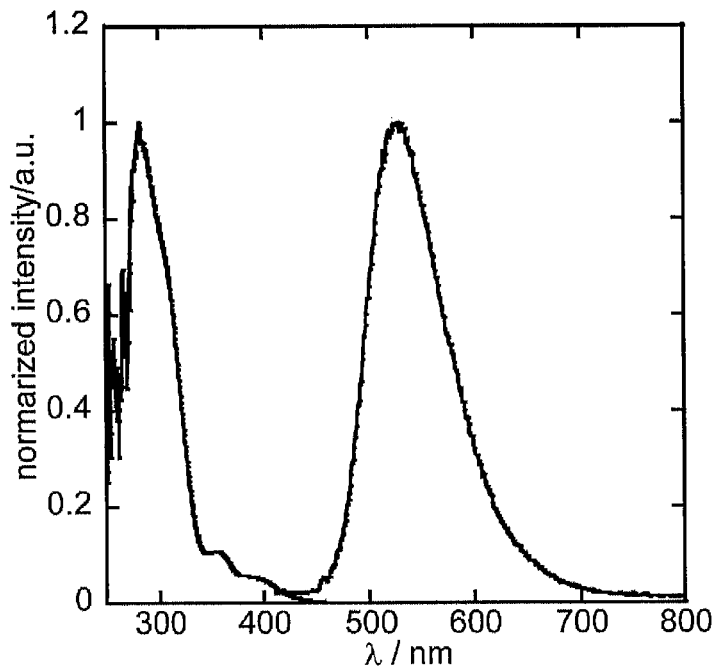
FIG. 10 is the absorption and emission spectra of the solution of the compound 5 in Example 1.
Figure 11:
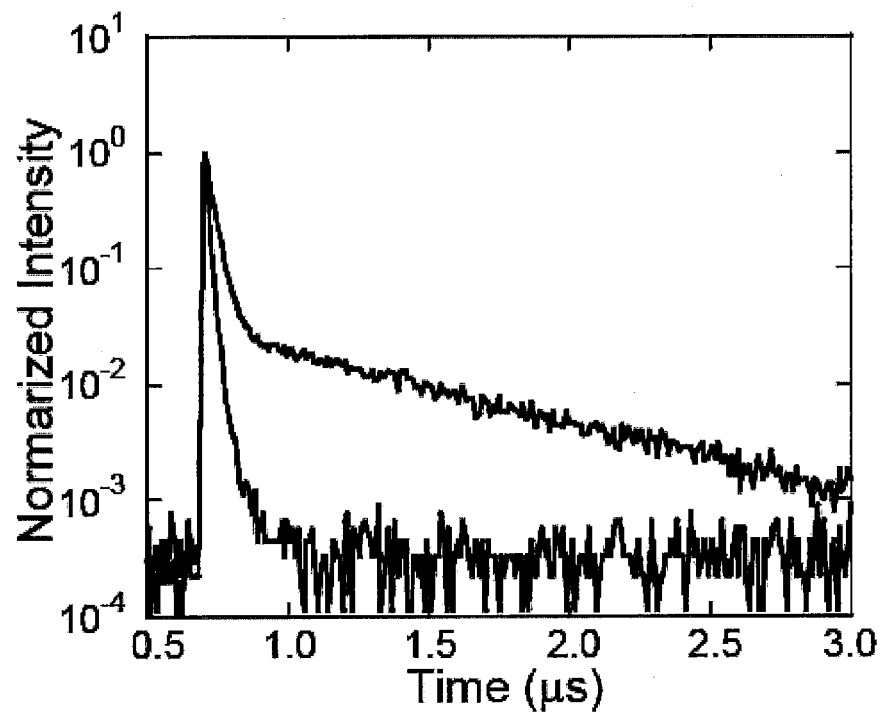
FIG. 11 is the transient decay curve of the solution of the compound 5 in Example 1.

A toluene solution of the compound 5 (concentration: $10^{-5}$ mol/L) was prepared and measured for the absorption and emission spectra. The results are shown in FIG. 10. The solution was measured for the transient decay curves at the peak light emission wavelength under conditions with Ar bubbling and without Ar bubbling. The results are shown in FIG. 11. Delayed fluorescent light was observed in the measurement under the condition with Ar bubbling. The photoluminescence quantum efficiency was 15% without Ar bubbling and 53% under Ar bubbling.

Comparative Example 1

Figure 12:
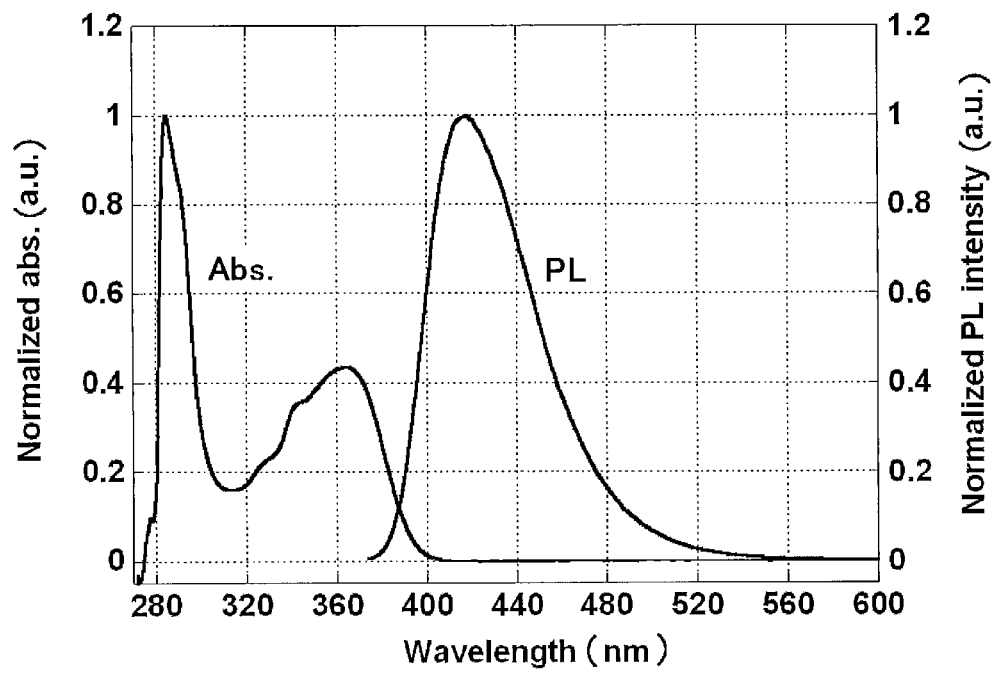
FIG. 12 is the absorption and emission spectra of the solution of the compound A in Comparative Example 1.
Figure 13:
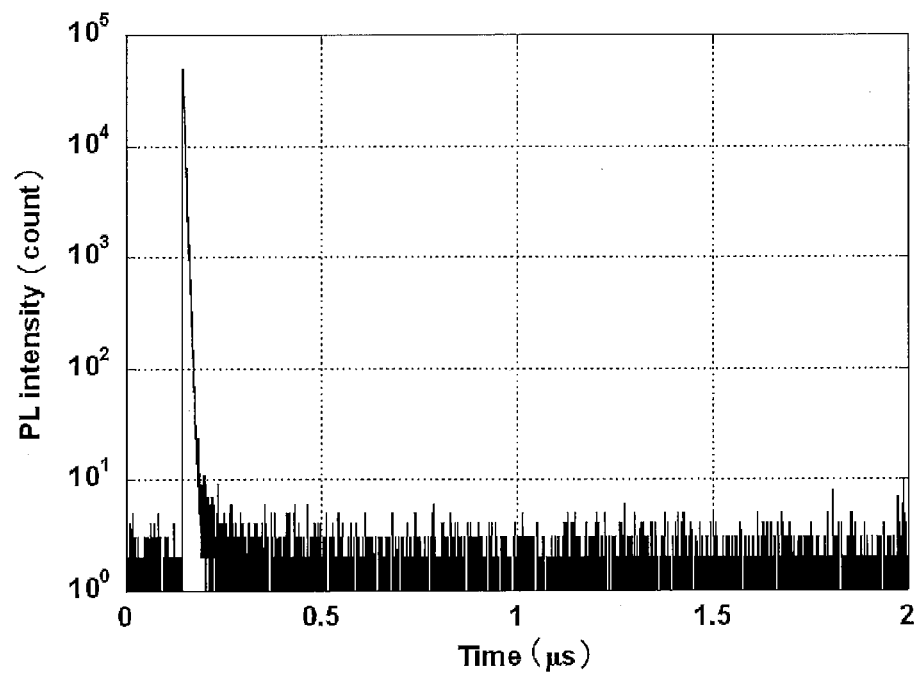
FIG. 13 is the transient decay curve of the solution of the compound A in Comparative Example 1.

A toluene solution was prepared and measured in the same manner as in Example 1 except that the following compound A was used instead of the compound 1. The absorption and emission spectra thereof are shown in FIG. 12. The transient decay curve thereof measured under the same conditions as in Example 1 is shown in FIG. 13. No delayed fluorescent light was observed.

[chem 40]

Compound A

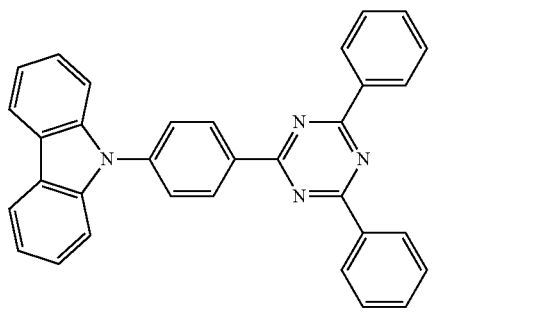

Example 2

Production and Evaluation of Organic Photoluminescent Device
(Thin Film)

A thin film of the compound 1 having a thickness of 50 nm was formed on a quartz substrate by a vacuum vapor deposition method under a condition of a vacuum degree of $10^{-4}$ Pa or less, thereby providing an organic photoluminescent device. The organic photoluminescent device thus produced was measured for the light emission spectrum with excitation light having a wavelength of 330 nm. The result is shown in FIG. 2.

Figure 14:
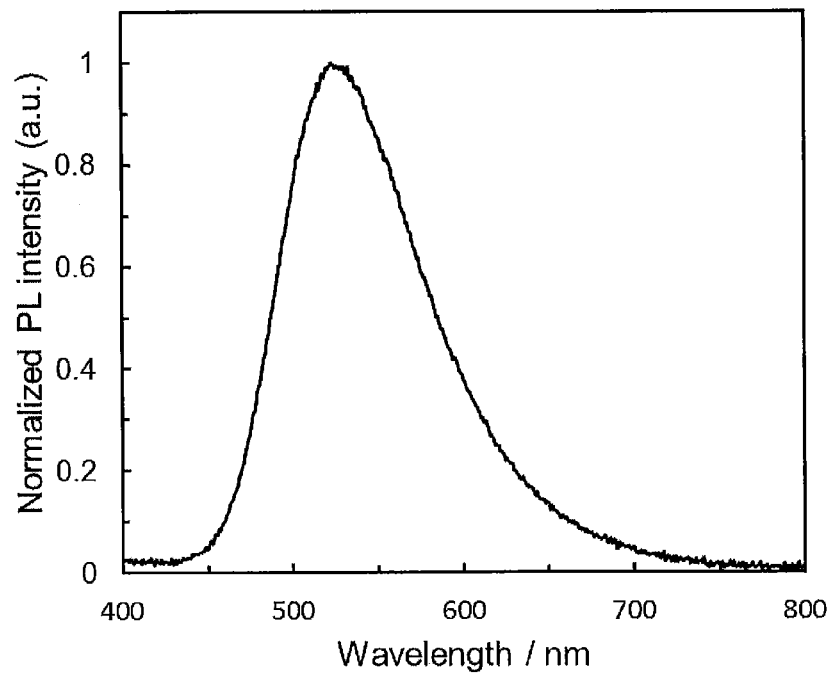
FIG. 14 is the light emission spectrum of the organic photoluminescent device of the compound 1 in Example 2.

The compound 1 and CBP were vapor-deposited from separate vapor deposition sources on a quartz substrate by a vacuum vapor deposition method under a condition of a vacuum degree of $10^{-4}$ Pa or less, so as to form a thin film having a thickness of 100 nm having a concentration of the compound 1 of 6.0% by weight, thereby providing an organic photoluminescent device. The organic photoluminescent device thus produced was measured for the light emission spectrum with excitation light having a wavelength of 330 nm. The result is shown in FIG. 14.

Example 3

Production and Evaluation of Organic Electroluminescent Device

Thin films were laminated on a glass substrate having formed thereon an anode formed of indium tin oxide (ITO) having a thickness of 50 nm, by a vacuum vapor deposition method at a vacuum degree of $10^{-4}$ Pa or less. Firstly, α-NPD was formed to a thickness of 100 nm on ITO, and thereon the compound 1 and CBP were co-deposited from separate vapor deposition sources to form a layer having a thickness of 40 nm, which was designated as a light emitting layer. At this time, the concentration of the compound 1 was 6.0% by weight. BAlq was then formed to a thickness of 30 nm, then 8-hydroxyquinolinatolithium (Liq) was vacuum vapor-deposited to a thickness of 1 nm, and then aluminum (Al) was vapor-deposited to a thickness of 80 nm to form a cathode, thereby producing an organic electroluminescent device 1.

An organic electroluminescent device 2 was produced in the same manner as above except that TAPC was used instead of α-NPD.

An organic electroluminescent device 3 was produced in the same manner as above except that TAPC was used instead of α-NPD, and BmPyPhB was used instead of BAlq.

Figure 15:
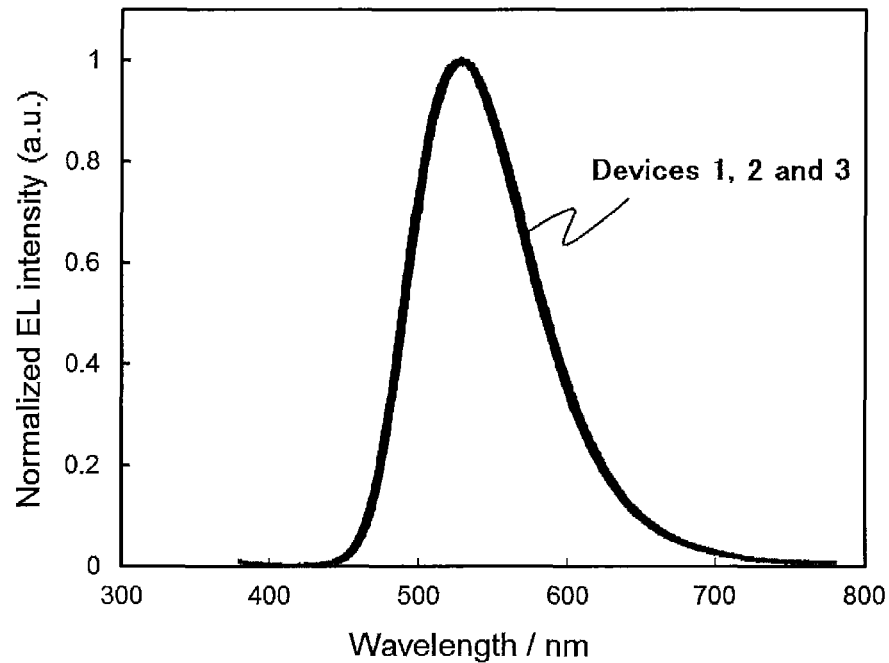
FIG. 15 is the light emission spectrum of the organic electroluminescent device of the compound 1 in Example 3.
Figure 16:
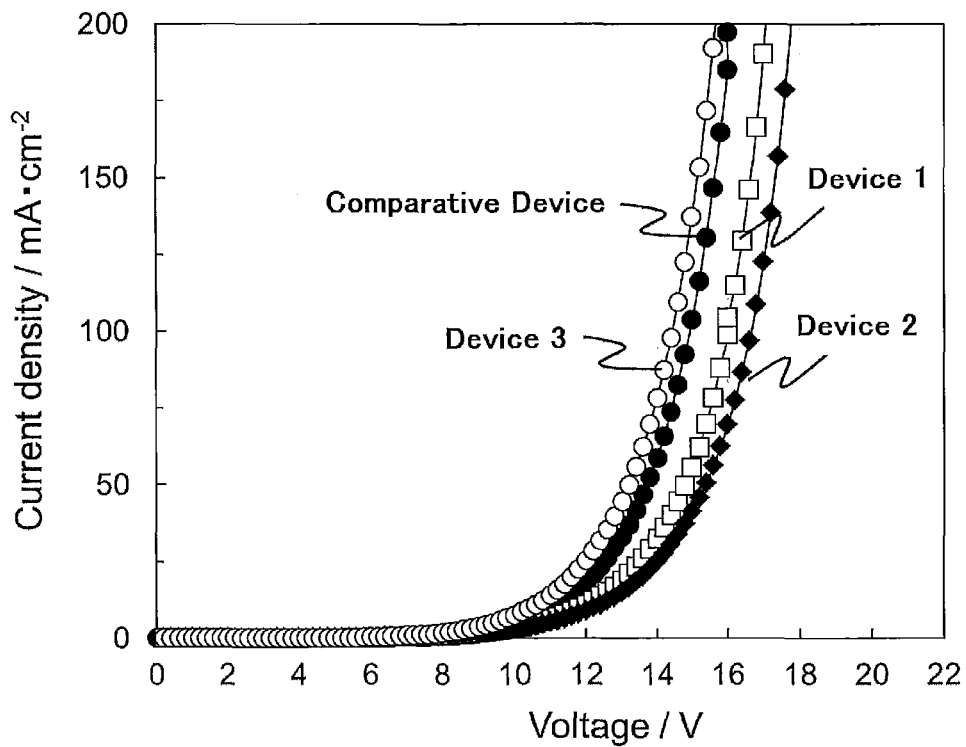
FIG. 16 is a graph showing the electric current density-voltage characteristics of the organic electroluminescent devices of the compound 1 in Example 3 and Ir(ppy)$_3$ in Comparative Example 2.
Figure 17:
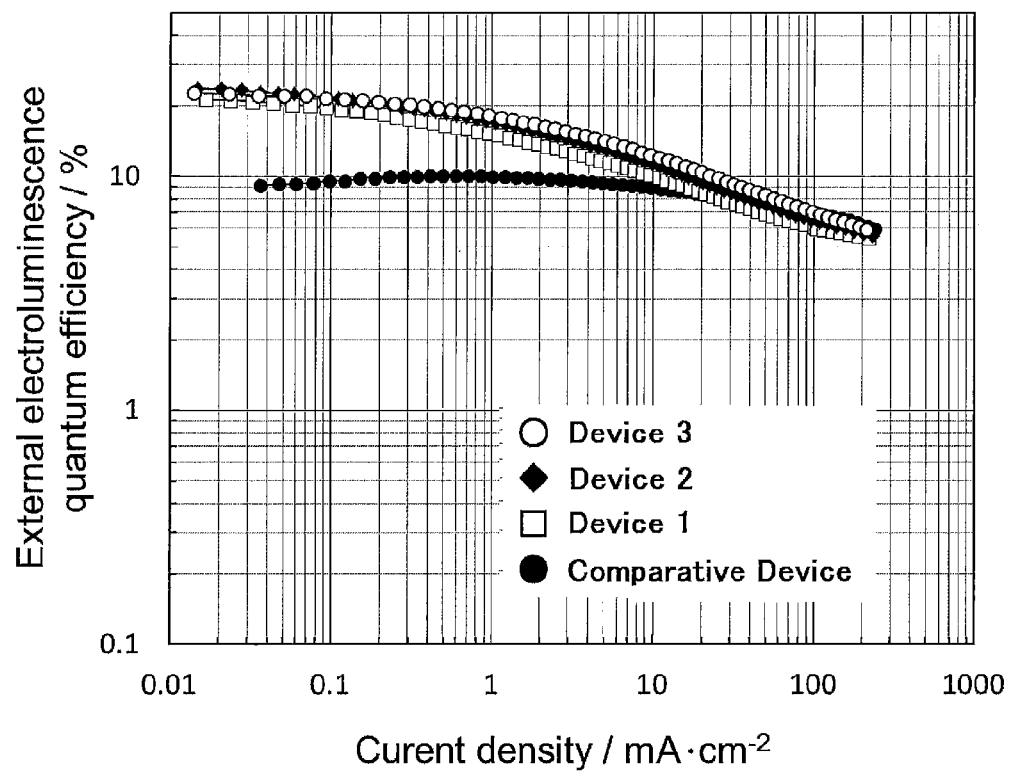
FIG. 17 is a graph showing the electric current density-external quantum efficiency characteristics of the organic electroluminescent devices of the compound 1 in Example 3 and Ir(ppy)$_3$ in Comparative Example 2.

The light emission spectra of the organic electroluminescent devices thus produced are shown in FIG. 15. The light emission spectra of the organic electroluminescent devices 1 to 3 overlapped each other. The electric current density-voltage characteristics thereof are shown in FIG. 16, and the electric current density-external quantum efficiency characteristics thereof are shown in FIG. 17.

An organic electroluminescent device 4 was produced in the same manner as in the device 1 except that TAPC was used instead of α-NPD, and the concentration of the compound 1 was changed from 6.0% by weight to 9.0% by weight. The device 4 achieved an external quantum efficiency of 29.6%.

All the devices 1 to 4 achieved a high external quantum efficiency. If an ideally balanced organic electroluminescent device is produced with a fluorescent material having a light emission quantum efficiency of 100%, the external quantum efficiency of fluorescent light emission of the device may be from 5 to 7.5% assuming that the light extraction efficiency is from 20 to 30%. It has been ordinarily considered that the value is the theoretical limit value of an external quantum efficiency of an organic electroluminescent device using a fluorescent material. The organic electroluminescent devices 1 to 4 of the invention are considerably excellent in such a point that a high external quantum efficiency that exceeds the theoretical limit value is achieved.

Comparative Example 2

Production and Evaluation of Organic Electroluminescent Device

An organic electroluminescent device for comparison (comparative device) was produced in the same manner as in the production of the device 1 in Example 3 except that Ir(ppy)$_3$ was used instead of the compound 1. The electric current density-voltage characteristics of the comparative device thus produced are shown in FIG. 16, and the electric current density-external quantum efficiency characteristics thereof are shown in FIG. 17. As apparent from the figures, it was confirmed that the devices 1 to 4 had a significantly larger external quantum efficiency than the comparative device. It was also confirmed that for the electric current efficiency, the devices 1 to 4 had a significantly larger external quantum efficiency than the comparative device.

[chem 41]

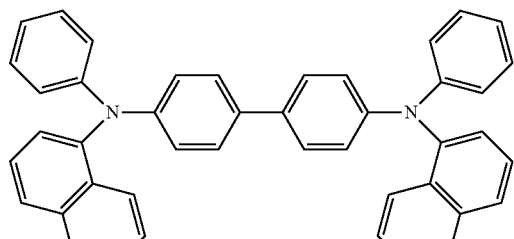

α-NPD

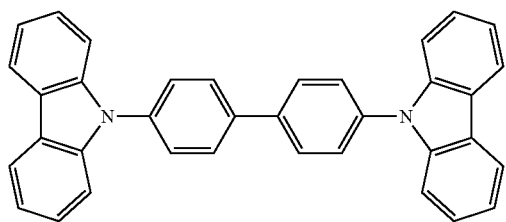

CBP

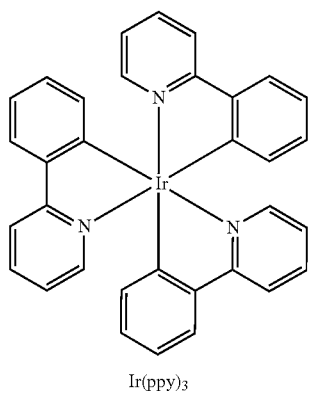

Ir(ppy)₃

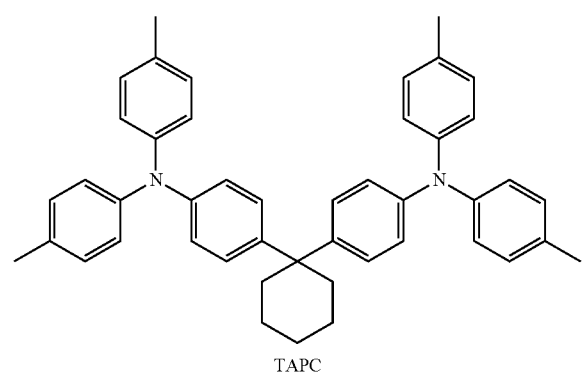

TAPC

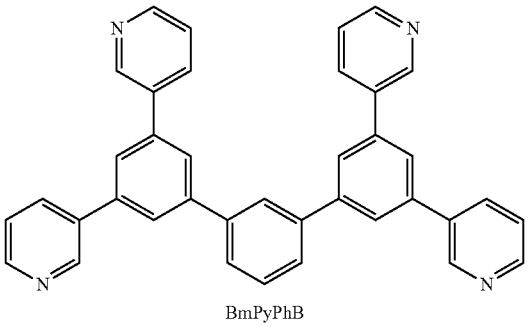

BmPyPhB

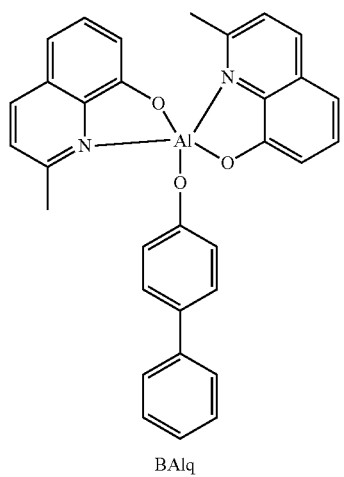

BAlq

INDUSTRIAL APPLICABILITY

The compound of the invention is useful as a light emitting material. Accordingly, the compound of the invention may be effectively used as a light emitting material of an organic light emitting device, such as an organic electroluminescent device. The compound of the invention includes a compound that emits delayed fluorescent light, and thus may be capable of providing an organic light emitting device having a high light emission efficiency. Thus, the invention has high industrial applicability.

REFERENCE SIGNS LIST

1 substrate
2 anode
3 hole injection layer
4 hole transporting layer
5 light emitting layer
6 electron transporting layer
7 cathode

The invention claimed is:

1. A compound represented by the following formula (2):

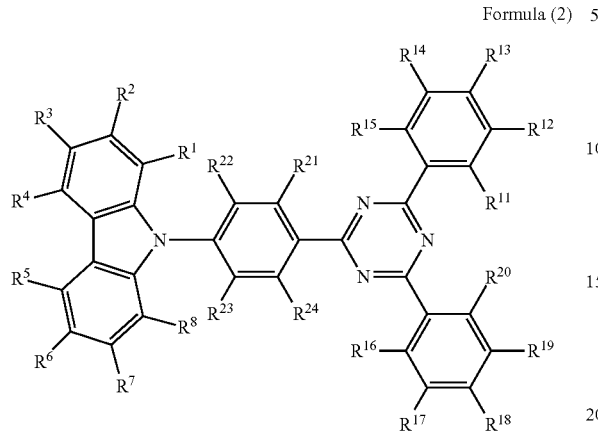

Formula (2)

wherein in the formula (2), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, and $R^{23}$ and $R^{24}$ each may be bonded to each other to form a cyclic structure, provided that at least one combination of $R^{21}$ and $R^{22}$, and $R^{23}$ and $R^{24}$ is bonded to each other to form a cyclic structure.

2. The compound according to claim 1, wherein in the formula (2), at least one of $R^1$ to $R^4$ represents a substituted or unsubstituted diarylamino group, and at least one of $R^5$ to $R^8$ represents a substituted or unsubstituted diarylamino group.

3. The compound according to claim 2, wherein $R^3$ and $R^6$ in the formula (2) each represent a substituted or unsubstituted diarylamino group.

4. A light emitting material containing the compound according to claim 1.

5. A delayed fluorescent emitter having a structure represented by the following formula (2):

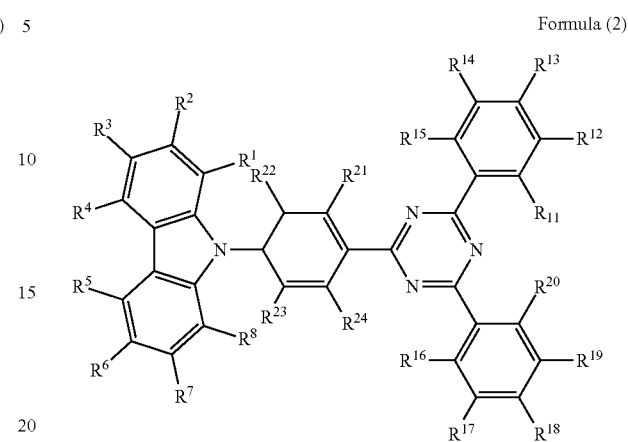

Formula (2)

wherein in the formula (2), $R^1$ to $R^8$ and $R^{11}$ to $R^{24}$ each independently represent a hydrogen atom or a substituent, provided that at least one of $R^1$ to $R^8$ represents a substituted or unsubstituted diarylamino group, and $R^1$ and $R^2$, $R^2$ and $R^3$, $R^3$ and $R^4$, $R^5$ and $R^6$, $R^6$ and $R^7$, $R^7$ and $R^8$, $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, and $R^{23}$ and $R^{24}$ each may be bonded to each other to form a cyclic structure, provided that at least one combination of $R^{21}$ and $R^{22}$, and $R^{23}$ and $R^{24}$ is bonded to each other to form a cyclic structure.

6. An organic light emitting device containing a substrate having thereon a light emitting layer containing the light emitting material according to claim 4.

7. The organic light emitting device according to claim 6, wherein the organic light emitting device emits delayed fluorescent light.

8. The organic light emitting device according to claim 6, wherein the organic light emitting device is an organic electroluminescent device.

* * * * *